US009980963B2

(12) United States Patent
Raymon et al.

(10) Patent No.: US 9,980,963 B2
(45) Date of Patent: *May 29, 2018

(54) TREATMENT OF CANCER WITH DIHYDROPYRAZINO-PYRAZINES

(71) Applicant: Signal Pharmaceuticals, LLC, San Diego, CA (US)

(72) Inventors: Heather Raymon, San Diego, CA (US); Shuichan Xu, San Diego, CA (US); Antonia Lopez-Girona, San Diego, CA (US); Toshiya Tsuji, San Diego, CA (US); Kristen Mae Hege, Burlingame, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/299,589

(22) Filed: Oct. 21, 2016

(65) Prior Publication Data

US 2017/0065583 A1 Mar. 9, 2017

Related U.S. Application Data

(63) Continuation of application No. 14/254,015, filed on Apr. 16, 2014, now Pat. No. 9,505,764.

(60) Provisional application No. 61/815,492, filed on Apr. 24, 2013, provisional application No. 61/813,031, filed on Apr. 17, 2013.

(51) Int. Cl.
*A61K 31/50* (2006.01)
*A61K 31/495* (2006.01)
*A61K 31/4985* (2006.01)
*C07D 487/04* (2006.01)
*C12Q 1/68* (2018.01)

(52) U.S. Cl.
CPC ........ *A61K 31/4985* (2013.01); *C07D 487/04* (2013.01); *C12Q 1/6886* (2013.01)

(58) Field of Classification Search
CPC . A61K 31/4985; C07D 487/04; C12Q 1/6886
USPC ......................................................... 514/249
See application file for complete search history.

(56) References Cited

U.S. PATENT DOCUMENTS

| | | |
|---|---|---|
| 3,507,866 A | 4/1970 | Jones et al. |
| 3,567,725 A | 3/1971 | Grabowski et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,031,105 A | 2/2000 | Wright |
| 6,093,728 A | 7/2000 | McMahon et al. |
| 6,372,740 B1 | 4/2002 | Murata et al. |
| 6,566,367 B2 | 5/2003 | Bakthavatchalam et al. |
| 6,791,006 B2 | 9/2004 | Nezu et al. |
| 6,800,436 B1 | 10/2004 | Jenne et al. |
| 6,825,184 B2 | 11/2004 | Cirillo et al. |
| 6,855,723 B2 | 2/2005 | McMahon et al. |
| 7,199,119 B2 | 4/2007 | Burkitt et al. |
| 7,247,621 B2 | 7/2007 | Hong et al. |
| 7,429,572 B2 | 9/2008 | Clark |
| 7,476,665 B2 | 1/2009 | Burgey |
| 7,608,622 B2 | 10/2009 | Liu et al. |
| 7,700,594 B2 | 4/2010 | Chen et al. |
| 7,767,687 B2 | 8/2010 | Oslob et al. |
| 7,902,187 B2 | 3/2011 | Neagu et al. |
| 7,919,490 B2 | 4/2011 | Neagu et al. |
| 7,968,556 B2 | 6/2011 | Mortensen et al. |
| 7,981,893 B2 | 7/2011 | Mortensen et al. |
| 8,110,578 B2 | 2/2012 | Perrin-Ninkovic et al. |
| 8,268,809 B2 | 9/2012 | Kalman et al. |
| 8,372,976 B2 | 2/2013 | Mortensen et al. |
| 8,383,634 B2 | 2/2013 | Mortensen et al. |
| 8,492,381 B2 | 7/2013 | Perrin-Ninkovic et al. |
| 8,507,492 B2 | 8/2013 | Perrin-Ninkovic et al. |
| 8,569,494 B2 | 10/2013 | Harris et al. |
| 8,642,660 B2 | 2/2014 | Goldfarb |
| 8,907,087 B2 | 12/2014 | Perrin-Ninkovic et al. |
| 9,155,736 B2 | 10/2015 | Xu et al. |
| 9,358,232 B2 | 6/2016 | Hege et al. |
| 9,359,364 B2 | 6/2016 | Menon et al. |
| 9,375,443 B2 | 6/2016 | Xu et al. |
| 9,403,829 B2 | 8/2016 | Connolly et al. |
| 9,416,134 B2 | 8/2016 | Eckert |

(Continued)

FOREIGN PATENT DOCUMENTS

| | | |
|---|---|---|
| CA | 2 458 699 | 3/2003 |
| DE | 262 026 | 11/1988 |

(Continued)

OTHER PUBLICATIONS

Barlin 1982, "Purine analogs as amplifiers of phleomycin. VII. Some 1H-inidazo[4,5-b]pyrazines and related compound," Australian Journal of Chemistry, vol. 35:2299-2306.
Beresnev et al., 2000, "Interaction of 5-methoxy-1,2,4-traizines with uras as a new route to 6-azapurines," Medeleev Commu., vol. 2:58-59.
Bergmann et al., 1963, "2-Phenylpurines, their chemical and enzumological reactivity," J. Chem Org. , pp. 3729-3735.
Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.
Booth et al., 1995, "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675.

(Continued)

*Primary Examiner* — My-Chau T. Tran
(74) *Attorney, Agent, or Firm* — Jones Day

(57) ABSTRACT

Provided herein are methods for treating or preventing chronic lymphocytic leukemia, comprising administering an effective amount of a Dihydropyrazino-Pyrazine Compound to a patient having chronic lymphocytic leukemia.

11 Claims, 18 Drawing Sheets

(56) References Cited

U.S. PATENT DOCUMENTS

Figure 1A:
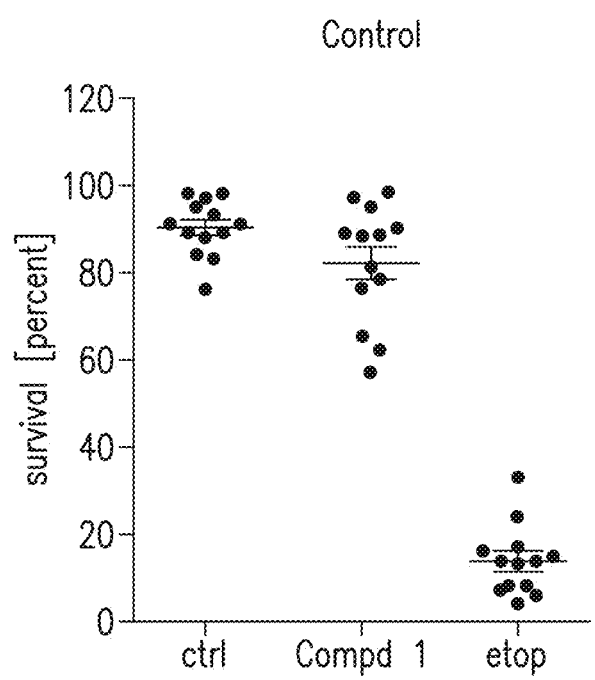

| | | | |
|---|---|---|---|
| 9,474,757 B2 | 10/2016 | Hege et al. | |
| 9,505,764 B2* | 11/2016 | Raymon | C07D 487/04 |
| 2004/0063658 A1 | 4/2004 | Roberts et al. | |
| 2006/0004014 A1 | 1/2006 | Hoffmann et al. | |
| 2006/0142269 A1 | 6/2006 | Dykes | |
| 2007/0036793 A1 | 2/2007 | Hardie et al. | |
| 2008/0194019 A1 | 8/2008 | Cantley et al. | |
| 2009/0181963 A1 | 7/2009 | Dehnhardt et al. | |
| 2009/0281075 A1 | 11/2009 | Roughton et al. | |
| 2010/0144738 A1 | 6/2010 | Bornmann et al. | |
| 2011/0257167 A1 | 10/2011 | Chopra et al. | |
| 2011/0318336 A1 | 12/2011 | Petricoin, III et al. | |
| 2012/0028972 A1 | 2/2012 | Wong et al. | |
| 2013/0102613 A1 | 4/2013 | Xu et al. | |
| 2013/0158023 A1 | 6/2013 | Ning et al. | |
| 2013/0245026 A1 | 9/2013 | Xu et al. | |
| 2013/0245027 A1 | 9/2013 | Xu et al. | |
| 2013/0245028 A1 | 9/2013 | Xu et al. | |
| 2013/0245029 A1 | 9/2013 | Xu et al. | |
| 2014/0314673 A1 | 10/2014 | Raymon et al. | |
| 2014/0314674 A1 | 10/2014 | Raymon et al. | |
| 2014/0314752 A1 | 10/2014 | Lopez-Girona et al. | |
| 2014/0314753 A1 | 10/2014 | Hege et al. | |
| 2014/0315848 A1 | 10/2014 | Raymon | |
| 2014/0315900 A1 | 10/2014 | Raymon et al. | |
| 2015/0299209 A1 | 10/2015 | Boerson et al. | |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 2003/032989 | 4/1903 |
| WO | WO 2004/042002 | 5/1904 |
| WO | WO 1999/16438 | 4/1999 |
| WO | WO 1999/28320 | 6/1999 |
| WO | WO 1999/28459 | 6/1999 |
| WO | WO 2000/73306 | 12/2000 |
| WO | WO 2002/048152 | 6/2002 |
| WO | WO 2002/076954 | 10/2002 |
| WO | WO 2003/072557 | 9/2003 |
| WO | WO 2003/093290 | 11/2003 |
| WO | WO 2004/048365 | 6/2004 |
| WO | WO 2004/065378 | 8/2004 |
| WO | WO 2004/076454 | 9/2004 |
| WO | WO 2004/078754 | 9/2004 |
| WO | WO 2004/085409 | 10/2004 |
| WO | WO 2004/096797 | 11/2004 |
| WO | WO 2005/002584 | 1/2005 |
| WO | WO 2005/003147 | 1/2005 |
| WO | WO 2005/021519 | 3/2005 |
| WO | WO 2005/120511 | 12/2005 |
| WO | WO 2006/001266 | 1/2006 |
| WO | WO 2006/018182 | 2/2006 |
| WO | WO 2006/030031 | 3/2006 |
| WO | WO 2006/036883 | 4/2006 |
| WO | WO 2006/045828 | 5/2006 |
| WO | WO 2006/046031 | 5/2006 |
| WO | WO 2006/050076 | 5/2006 |
| WO | WO 2006/065703 | 6/2006 |
| WO | WO 2006/087530 | 8/2006 |
| WO | WO 2006/090167 | 8/2006 |
| WO | WO 2006/090169 | 8/2006 |
| WO | WO 2006/091737 | 8/2006 |
| WO | WO 2006/108103 | 10/2006 |
| WO | WO 2007/044698 | 4/2007 |
| WO | WO 2007/044729 | 4/2007 |
| WO | WO 2007/044813 | 4/2007 |
| WO | WO 2007/047754 | 4/2007 |
| WO | WO 2007/060404 | 5/2007 |
| WO | WO 2007/066099 | 6/2007 |
| WO | WO 2007/066102 | 6/2007 |
| WO | WO 2007/080382 | 7/2007 |
| WO | WO 2007/125321 | 11/2007 |
| WO | WO 2007/129044 | 11/2007 |
| WO | WO 2007/129052 | 11/2007 |
| WO | WO 2007/129161 | 11/2007 |
| WO | WO 2007/135398 | 11/2007 |
| WO | WO 2008/016669 | 2/2008 |
| WO | WO 2008/023161 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032089 | 3/2008 |
| WO | WO 2008/032091 | 3/2008 |
| WO | WO 2008/051493 | 5/2008 |
| WO | WO 2008/064093 | 5/2008 |
| WO | WO 2008/115974 | 9/2008 |
| WO | WO 2008/140947 | 11/2008 |
| WO | WO 2009/007748 | 1/2009 |
| WO | WO 2009/007750 | 1/2009 |
| WO | WO 2009/007751 | 1/2009 |
| WO | WO 2009/052145 | 4/2009 |
| WO | WO 2009/102986 | 8/2009 |
| WO | WO 2010/006072 | 1/2010 |
| WO | WO 2010/062571 | 6/2010 |
| WO | WO 2010/068483 | 6/2010 |
| WO | WO 2011/031965 | 3/2011 |
| WO | WO 2011/053518 | 5/2011 |
| WO | WO 2011/079114 | 6/2011 |
| WO | WO 2011/097333 | 8/2011 |
| WO | WO 2012/016113 | 2/2012 |

OTHER PUBLICATIONS

Booth et al., 2001, "The Reactions of Diaminomaleonitrile with Isocyanates and Either Aldehydes or Ketones Revisited," J. Org Chem, vol. 66:8436-8441.

Booth, et al., 1994, "Synthesis of 4- and 5-Disubstituted 1-Benzylimidazoles, Important Precursors of Purine Analogs," J. of Heterocyclic of Chemistry, vol. 31(2):345-50.

Carretero et al. 2010, "Integrative Genomic and Proteomic Analyses Indentity Targets for Lkbl-Deficient Metastatic Lung Tumors," Cancer Cell, vol. 17(6): 547-559.

Chupakhin et al., 2001, "A simple one pot synthesis of condensed 1,2,4-triazines by using the tandem $A_N$-$S_N$ipso and $S_N^H$—$S_N$ipso reactions," J. of Heterocyclic Chemistry, vol. 38(4):901-907.

Cohen, 2005, *Protein Kinase Inhibitors for the Treatment of Disease: The Promise and the Problems*, Handbook of Experimental Pharmacology, Springer Berlin Heidelberg, 167:1-7.

Cohen, P. 2001, "The role of protein phosphorylation in human health and disease," Eur. J. Biochem, vol. 268:5001-5010.

Cohen, P. 2002, "Protein kinases—the major drug targets of the twenty-first century?" Nature Reviews/Drug Discovery, vol. 1:309-315.

Coish, et al., 2006, "Small molecule inhibitors of IKK kinase activity," Expert Opin. Ther. Patents, vol. 16(1):1-12.

Crofts et al., 1997 "Metabolism of 2-amino-1-methyl-6-phenylimidazo [4,5-b]pyridine (PhIP) by human cytochrome P4501B1," Carcinogenesis, vol. 18(9):1793-1798.

Dang et al., 1999, "Efficient synthesis of purines and purine nucelosides via an inverse electron demand diels-alder reaction," J. Am Chem Soc., vol. 121(24):5833-5834.

Database CAPLUS Online Chemical Abstracts Service, Columbus, Ohio, Database Accession No. 1951:49974 (XP-002472261) (1951).

Database CAPLUS Online Chemical Abstracts Service, Columbus, Ohio, Database Accession No. 1966:26849 (XP-002472263) (1965).

Database CAPLUS Online Chemical Abstracts Service, Columbus, Ohio, Database Accession No. 1978:433195 (XP-002472262) (1978).

(56) References Cited

OTHER PUBLICATIONS

Decker et al., 2009, "A pilot trial of the mTOR (mammalian target of rapamycin) inhibitor RAD001 in patients with advanced B-CLL," Annals of hematology 88.3 (2009): 221-227.
Dornow et al., 1957, "Synthese von2-Oxy-imiclazolo-(5',4':2,3)-pyridinen)," Arch Pharm. vol. 290, pp. 20-31 (w/English language abstract).
Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.
Fabbro et al., 2002, "Protein kinases as targets for anticancer agents: from inhibitors to useful drugs," Pharmacol Ther., 93(2-3):79-98.
Farhadi et al., 2006, "The role of protein kinase C isoforms in modulating injury and repair of the intestinal barrier," J. Pharm Exp. Ther., vol. 316(1):1-7.
Frandsen et al., 1992, "Reaction of the N2-acetoxy derivative of 2-amino-1-methyl-6-phenylimidazo[4,5,b] pyridine . . . ," Carcinogenesis, vol. 13(4):629-635.
Gao et al., 2010, "LKB1 inhibits lung cancer progression through lysyl oxidase and extracellular matrix remodeling," Proceedings of the National Academy of Sciences, vol. 107(44): 18892-18897.
Gao et al.: 2011, "LKB1 in lung cancerigenesis: a serine/threonine kinase as tumor suppressor," Protein & Cell, Gaodeng Jiaoyu Chubanshe, China, vol. 2(2): 99-107.
Georgakis and Younes, 2006, "From rapi nui to rapamycin: targeting PI3K/Akt/mTOR for cancer therapy," Expert Rev. Anticancer Ther., vol. 6(1):131-140.
Gini et al., 2013, "The mTOR Kinase Inhibitors, CC214-1 and CC214-2, Preferentially Block the Growth of EGFRvIII-Activated Glioblastomas," Clin Cancer Res 2013;19:5722-5732.
Grimmiger et al., 2010, "Targeting non-malignant disorders with tyrosine kinase inhibitors," Nat. Rev. Drug Disc., 9(12):956-970.
Hamad, 2001, "A new synthesis of 4-cyano-1,3-dihydro-2-oxo-2H-imidazole-5-(N-tosyl)carboxamide: Reactive precursor for thiopurine analogues," J of Heterocyclic Chemistry, vol. 38(4):939-944.
Hernan et al., "De novo germline mutation in the serine-threonine kinase STK11/LKB1 gene associated with Peutz-Jeghers syndrome," Clin Genet., 66(1):58-62.
Huang et al., 2010, "Genetic and epigenetic silencing of SCARA5 may contribute to human hepatocellular carcinoma by activating FAK signaling," Journal of Clinical Investigation, American Society for Clinical investigation, vol. 120(1): 223-241.
Inge et al., 2009, "Expression of LKB1 tumor suppressor in non-small cell lung cancer determines sensitivity to 2-deoxyglucose," Journal of Thoracic and Cardiovascular Surgery, vol. 137(3): 580-586.
Irie et al., 2005, "Toward the development of new medicinal leads with selectivity for protein kinase C isozymes," The Chemical Record, vol. 5:185-195.
Itoh et al., 2004, "A novel practical synthesis of C-2-arylpurines," Advanced Synthesis & Catalysis, vol. 346:1859-1867.
Ji et al., 2007, "LKB1 modulates lung cancer differentiation and metastasis," Nature, 448(7155):807-810.
Johnson et al., 2003, "Advances in the therapy of chronic lymphocytic leukemia," Current opinion in Hematology 10.4 (2003): 297-305.
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al., 2003, "Synthesis of 6-substituted 9-benzyl-8-hydroxypurines with potential interferon-indcuing activity," Chemical & Pharmaceutical Bulletin, vol. 51(5):608-611.
Killday et al., 2001, "Microxine, a new cdc2 kinase inhibitor from the Australian marine sponge *Microxina* species," J. of Natural Products, vol. 64(4):525-526.
Mahoney et al., 2009, "LKB1/KRAS mutant lung cancers constitute a genetic subset of NSCLC with increased sensitivity to MAPK and mTOR signalling inhibition," Br J Cancer, 100(2):370-375.

Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.
Nagashima et al., 2004, "Solution-Phase parallel synthesis of an N-Alkylated dihydropteridinone library from fluorous amino acids," J of Comb. Chemistry, vol. 6(6):942-949.
Park et al., 2000, "A novel mechanism of TRAF signaling revealed by structural and functional analyses of the TRADD-TRAF2 interaction," Cell, vol. 101:777-787.
Patani et al., 1998, "Bioisosterim: A rational approach in drug design," Chemical Reviews, vol. 96:3147-3176.
PCT Annex to Form PCT/ISA?206 Communication Relating to the Results of the Partial International Search issued in connection with PCT/US2012/049281,filed Aug. 2, 2012.
PCT International Search Report issued in connection with PCT/US2012/049281, filed Aug. 2, 2012.
PCT Written Opinion of the International Searching Authority issued in connection with PCT/US2012/049281, filed Aug. 2, 2012.
Pekarsky et al., 2010, "Molecular basis of CLL," Seminars in cancer biology, vol. 20, No. 6, pp. 370-376, Academic Press, Dec. 1, 2010.
Registry File Document for RN 863501-03-5, 863502-39-0 and others (Sep. 20, 2005).
Seela et al., 2004, "Product Class 17: Purines," Science of Synthesis, vol. 16, pp. 945-1108.
Shaw et al., 2004, "The LKB1 tumor suppressor negativiely regulates mTOR signaling," Cancer Cell, vol. 6(1): 91-99.
Shaw et al., 2009, "LKB1 and AMP-activated protein kinase control of mTOR signalling and growth," Acta. Physiol (Oxf.) 196(1):65-80.
Shoji et al. 2012, "Genotype-dependent efficacy of a dual PI3K/mTOR inhibitor, NVP-BEZ235, and an mTOR inhibitor, RAD001, in endometrial carcinomas." *PloS one* 7.5, 2012, e37431.
Singh et al., 1994, "Novel cAMP PDE III Inhibitors: Imidazo[4,5-b]pyridin-2(3H)-ones and Thiazolo [4,5-b]pyridin-2(3h)-ones and Their Analogs," J. Med. Chem, vol. 37(2):248-54.
Skowronska et al., 2012, "ATM germline heterozygosity does not play a role in chronic lymphocytic leukemia initiation but influences rapid disease progression through loss of the remaining ATM allele," haematologica 97.1 (2012): 142-146.
Sridhar et al., 2000, "Protein kinases as therapeutic targets," Pharm. Res., 17(11):1345-1353.
Wallace 2008, "Palladium-catalyzed synthesis of quinoxaline derivatives," Tetrahedron, vol. 64:9675-9684.
Wei et al., 2009, "Chemopreventive efficacy of rapamycin on Peutz-Jeghers syndrome in a mouse model," Cancer Lett., 277(2):149-154.
Westover et al., 1981, "Synthesis and antiviral activity of certain 9-β-D-Riofuranoaylpurine-6-carboxamides," J.Med. Chem., vol. 24(8):941-46.
Wingo et al., 2009, "Somatic LKB1 mutations promote cervical cancer progression," PloS One, 4(4):1-8.
Yoneda et al., 1976, "A transformationof 7-azapteridines into 6-azapurines (Imidazo [4,5-e]- as -triazines)," Heterocycles, vol. 4(9):1503-1508.
Yoneda et al., 1978, "Synthesis of imadazo[4,5-e]-as-triazine (6-Azapurine) Deriviatives," Chem & Pharm Bulletin, vol. 26(10):3154-3160.
Yuan et al., 2009, "Targeting tumorigenesis: development and use of mTOR inhibitors in cancer therapy," Journal of Hematology & Oncology, Biomed Central Ltd., London UK, vol. 2(1): 45.
Zaki et al., 2007, "The synthesis of imidazol[4,5-d]pyridines from a substituted imidazole and acyl or sulfonyl acetonitrile," Tetrahedron, vol. 63(18):3745-3753.
Zhong et al., 2006, "LKB1 mutation in large cell carcinoma of the lung," Cancer Lung, vol. 53(3):285-294.
Herling et al., 2008 "High TCL1 expression and intact T-cell receptor signaling define a hyperproliferative subset of T-cell prolymphocytic leukemia," Blood 111.1 (2008): 328-337.

\* cited by examiner

TREATMENT OF CANCER WITH DIHYDROPYRAZINO-PYRAZINES

This application is a continuation of U.S. Non-Provisional application Ser. No. 14/254,015, filed Apr. 16, 2014, currently allowed, which claims the benefit of U.S. Provisional Application No. 61/813,031, filed Apr. 17, 2013 and U.S. Provisional Application No. 61/815,492, filed Apr. 24, 2013, the entire contents of which are incorporated herein by reference.

1. FIELD

Provided herein are methods for treating or preventing chronic lymphocytic leukemia, comprising administering an effective amount of a Dihydropyrazino-Pyrazine Compound to a patient having chronic lymphocytic leukemia (CLL), or T-cell prolymphocytic leukemia (T-PLL).

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001), *Protein Kinase Inhibitors for the Treatment of Disease: The Promise and the Problems*, Handbook of Experimental Pharmacology, Springer Berlin Heidelberg, 167 (2005).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17(11):1345-1353 (2000). Viral infections and the conditions related thereto have also been associated with the regulation of protein kinases. Park et al. Cell 101 (7): 777-787 (2000).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), which is also called FRAP, RAFTI or RAPTI), is a 2549-amino acid Ser/Thr protein kinase, that has been shown to be one of the most critical proteins in the mTOR/PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. While mTORC1 is sensitive to rapamycin analogs (such as temsirolimus or everolimus), mTORC2 is largely rapamycin-insensitive. Notably, rapamycin is not a TOR kinase inhibitor. Several mTOR inhibitors have been or are being evaluated in clinical trials for the treatment of cancer. Temsirolimus was approved for use in renal cell carcinoma in 2007 and sirolimus was approved in 1999 for the prophylaxis of renal transplant rejection. Everolimus was approved in 2009 for renal cell carcinoma patients that have progressed on vascular endothelial growth factor receptor inhibitors, in 2010 for subependymal giant cell astrocytoma (SEGA) associated with tuberous sclerosis (TS) in patients who require therapy but are not candidates for surgical resection, and in 2011 for progressive neuroendocrine tumors of pancreatic origin (PNET) in patients with unresectable, locally advanced or metastatic disease. There remains a need for additional TOR kinase inhibitors.

DNA-dependent protein kinase (DNA-PK) is a serine/threonine kinase involved in the repair of DNA double strand breaks (DSBs). DSBs are considered to be the most lethal DNA lesion and occur endogenously or in response to ionizing radiation and chemotherapeutics (for review see Jackson, S. P., Bartek, J. The DNA-damage response in human biology and disease. Nature Rev 2009; 461:1071-1078). If left unrepaired, DSBs will lead to cell cycle arrest and/or cell death (Hoeijmakers, J. H. J. Genome maintenance mechanisms for preventing cancer. Nature 2001; 411: 366-374; van Gent, D. C., Hoeijmakers, J. H., Kanaar, R. Chromosomal stability and the DNA double-stranded break connection. *Nat Rev Genet* 2001; 2: 196-206). In response to the insult, cells have developed complex mechanisms to repair such breaks and these mechanisms may form the basis of therapeutic resistance. There are two major pathways used to repair DSBs, non-homologous end joining (NHEJ) and homologous recombination (HR). NHEJ brings broken ends of the DNA together and rejoins them without reference to a second template (Collis, S. J., DeWeese, T. L., Jeggo P. A., Parker, A. R. The life and death of DNA-PK. Oncogene 2005; 24: 949-961). In contrast, HR is dependent on the proximity of the sister chromatid which provides a template to mediate faithful repair (Takata, M., Sasaki, M. S., Sonoda, E., Morrison, C., Hashimoto, M., Utsumi, H., et al. Homologous recombination and non-homologous end-joining pathways of DNA double-strand break repair have overlapping roles in the maintenance of chromosomal integrity in vertebrate cells. *EMBO J* 1998; 17: 5497-5508; Haber, J. E. Partners and pathways repairing a double-strand break. *Trends Genet* 2000; 16: 259-264). NHEJ repairs the majority of DSBs. In NHEJ, DSBs are recognized by the Ku protein that binds and then activates the catalytic subunit of DNA-PK. This leads to recruitment and activation of end-processing enzymes, polymerases and DNA ligase IV (Collis, S. J., DeWeese, T. L., Jeggo P. A., Parker, A. R. The life and death of DNA-PK. *Oncogene* 2005; 24: 949-961). NHEJ is primarily controlled by DNA-PK and thus inhibition of DNA-PK is an attractive approach to modulating the repair response to exogenously induced DSBs. Cells deficient in components of the NHEJ pathway are defective in DSB repair and highly sensitive to ionizing radiation and topoisomerase poisons (reviewed by Smith, G. C. M., Jackson, S. P. The DNA-dependent protein kinase. *Genes Dev* 1999; 13: 916-934; Jeggo, P. A., Caldecott, K., Pidsley, S., Banks, G. R. Sensitivity of Chinese hamster ovary mutants defective in DNA double strand break repair to topoisomerase II inhibitors. *Cancer Res* 1989; 49: 7057-7063). A DNA-PK inhibitor has been reported to have the same effect of sensitizing cancer cells to therapeutically induced DSBs (Smith, G. C. M., Jackson, S. P. The DNA-dependent protein kinase. *Genes Dev* 1999; 13: 916-934).

Citation or identification of any reference in Section 2 of this application is not to be construed as an admission that the reference is prior art to the present application.

3. SUMMARY

Provided herein are methods for treating or preventing chronic lymphocytic leukemia (CLL) or T-cell prolymphocytic leukemia (T-PLL), comprising administering an effective amount of a Dihydropyrazino-Pyrazine Compound to a patient having CLL or T-PLL.

In certain embodiments, provided herein are methods for achieving an International Workshop on Chronic Lymphocytic Leukemia (IWCLL) response definition of complete response (CR), complete response with incomplete marrow recovery (CRi), partial response (PR), or stable disease (SD) in a patient having CLL or T-PLL, comprising administering an effective amount of a Dihydropyrazino-Pyrazine Compound to said patient.

In certain embodiments, provided herein are methods for achieving a National Cancer Institute-sponsored Working Group on Chronic Lymphocytic Leukemia (NCI-WG CLL) response definition of complete response (CR), complete response with incomplete marrow recovery (CRi), partial response (PR) or stable disease (SD) in a patient having CLL or T-PLL, comprising administering an effective amount of a Dihydropyrazino-Pyrazine Compound to said patient.

In certain embodiments, provided herein are methods for treating CLL or T-PLL, comprising administering an effective amount of a Dihydropyrazino-Pyrazine Compound to a patient having CLL or T-PLL, wherein the treatment results in one or more of inhibition of disease progression, increased Time To Progression (TTP), increased Overall Survival (OS), increased Progression-free Survival (PFS), increased Event-free Survival, increased Disease-free Survival, increased Response Duration, increased Lymphoma-specific survival, and/or increased Time To Next Treatment.

In some embodiments, the Dihydropyrazino-Pyrazine Compound is a compound as described herein.

The present embodiments can be understood more fully by reference to the detailed description and examples, which are intended to exemplify non-limiting embodiments.

4. DETAILED DESCRIPTION

4.1 Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. Examples of unsaturared alkyl groups include, but are not limited to, vinyl, allyl, —CH=CH(CH$_3$), —CH=C (CH$_3$)$_2$, —C(CH$_3$)=CH$_2$, —C(CH$_3$)=CH(CH$_3$), —C(CH$_2$CH$_3$)=CH$_2$, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

An "alkenyl" group is a straight chain or branched non-cyclic hydrocarbon having from 2 to 10 carbon atoms, typically from 2 to 8 carbon atoms, and including at least one carbon-carbon double bond. Representative straight chain and branched (C$_2$-C$_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturared cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclylalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopentylmethyl, cyclopentylethyl, cyclohexylmethyl, cyclohexylethyl, and cyclohexylpropyl. Representative substituted cycloalkylalkyl groups may be mono-substituted or substituted more than once.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

A "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyrdine-3-yl methyl, (tetrahydro-2H-pyran-4-yl)methyl, (tetrahydro-2H-pyran-4-yl)ethyl, tetrahydrofuran-2-yl methyl, tetrahydrofuran-2-yl ethyl, and indol-2-yl propyl.

A "halogen" is chloro, iodo, bromo, or fluoro.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amine" group is a radical of the formula: —NH$_2$.

A "hydroxyl amine" group is a radical of the formula: —N(R$^{\#}$)OH or —NHOH, wherein R$^{\#}$ is a substituted or unsubstituted alkyl, cycloalkyl, cycloalkylalkyl, aryl, aralkyl, heterocyclyl or heterocyclylalkyl group as defined herein.

An "alkoxyamine" group is a radical of the formula: —N(R$^{\#}$)O-alkyl or —NHO-alkyl, wherein R$^{\#}$ is as defined above.

An "aralkoxyamine" group is a radical of the formula: —N(R#)O-aryl or —NHO-aryl, wherein R# is as defined above.

An "alkylamine" group is a radical of the formula: —NH-alkyl or —N(alkyl)$_2$, wherein each alkyl is independently as defined above.

An "aminocarbonyl" group is a radical of the formula: —C(=O)N(R#)$_2$, —C(=O)NH(R#) or —C(=O)NH$_2$, wherein each R# is as defined above.

An "acylamino" group is a radical of the formula: —NHC(=O)(R#) or —N(alkyl)C(=O)(R#), wherein each alkyl and R# are independently as defined above.

An "O(alkyl)aminocarbonyl" group is a radical of the formula: —O(alkyl)C(=O)N(R#)$_2$, —O(alkyl)C(=O)NH(R#) or —O(alkyl)C(=O)NH$_2$, wherein each R# is independently as defined above.

An "N-oxide" group is a radical of the formula: —N$^+$—O$^-$.

A "carboxy" group is a radical of the formula: —C(=O)OH.

A "ketone" group is a radical of the formula: —C(=O)(R#), wherein R# is as defined above.

An "aldehyde" group is a radical of the formula: —CH(=O).

An "ester" group is a radical of the formula: —C(=O)O(R#) or —OC(=O)(R#), wherein R# is as defined above.

A "urea" group is a radical of the formula: —N(alkyl)C(=O)N(R#)$_2$, —N(alkyl)C(=O)NH(R#), —N(alkyl)C(=O)NH$_2$, —NHC(=O)N(R#)$_2$, —NHC(=O)NH(R#), or —NHC(=O)NH$_2$#, wherein each alkyl and R# are independently as defined above.

An "imine" group is a radical of the formula: —N=C(R#)$_2$ or —C(R#)=N(R#), wherein each R# is independently as defined above.

An "imide" group is a radical of the formula: —C(=O)N(R#)C(=O)(R#) or —N((C=O)(R#))$_2$, wherein each R# is independently as defined above.

A "urethane" group is a radical of the formula: —OC(=O)N(R#)$_2$, —OC(=O)NH(R#), —N(R#)C(=O)O(R#), or —NHC(=O)O(R#), wherein each R# is independently as defined above.

An "amidine" group is a radical of the formula: —C(=N(R#))N(R#)$_2$, —C(=N(R#))NH(R#), —C(=N(R#))NH$_2$, —C(=NH)N(R#)$_2$, —C(=NH)NH(R#), —C(=NH)NH$_2$, —N=C(R#)N(R#)$_2$, —N=C(R#)NH(R#), —N=C(R#)NH$_2$, —N(R#)C(R#)=N(R#), —NHC(R#)=N(R#), —N(R#)C(R#)=NH, or —NHC(R#)=NH, wherein each R# is independently as defined above.

A "guanidine" group is a radical of the formula: —N(R#)C(=N(R#))N(R#)$_2$, —NHC(=N(R#))N(R#)$_2$, —N(R#)C(=NH)N(R#)$_2$, —N(R#)C(=N(R#))NH(R#), —N(R#)C(=N(R#))NH$_2$, —NHC(=NH)N(R#)$_2$, —NHC(=N(R#))NH(R#), —NHC(=N(R#))NH$_2$, —NHC(=NH)NH(R#), —NHC(=NH)NH$_2$, —N=C(N(R#)$_2$)$_2$, —N=C(NH(R#))$_2$, or —N=C(NH$_2$)$_2$, wherein each R# is independently as defined above.

A "enamine" group is a radical of the formula: —N(R#)C(R#)=C(R#)$_2$, —NHC(R#)=C(R#)$_2$, —C(N(R#)$_2$)=C(R#)$_2$, —C(NH(R#))=C(R#)$_2$, —C(NH$_2$)=C(R#)$_2$, —C(R#)=C(R#)(N(R#)$_2$), —C(R#)=C(R#)(NH(R#)) or —C(R#)=C(R#)(NH$_2$), wherein each R# is independently as defined above.

An "oxime" group is a radical of the formula: —C(=NO(R#))(R#), —C(=NOH)(R#), —CH(=NO(R#)), or —CH(=NOH), wherein each R# is independently as defined above.

A "hydrazide" group is a radical of the formula: —C(=O)N(R#)N(R#)$_2$, —C(=O)NHN(R#)$_2$, —C(=O)N(R#)NH(R#), —C(=O)N(R#)NH$_2$, —C(=O)NHNH(R#)$_2$, or —C(=O)NHNH$_2$, wherein each R# is independently as defined above.

A "hydrazine" group is a radical of the formula: —N(R#)N(R#)$_2$, —NHN(R#)$_2$, —N(R#)NH(R#), —N(R#)NH$_2$, —NHNH(R#)$_2$, or —NHNH$_2$, wherein each R# is independently as defined above.

A "hydrazone" group is a radical of the formula: —C(=N—N(R#)$_2$)(R#)$_2$, —C(=N—NH(R#))(R#)$_2$, —C(=N—NH$_2$)(R#)$_2$, —N(R#)(N=C(R#)$_2$), or —NH(N=C(R#)$_2$), wherein each R# is independently as defined above.

An "azide" group is a radical of the formula: —N$_3$.

An "isocyanate" group is a radical of the formula: —N=C=O.

An "isothiocyanate" group is a radical of the formula: —N=C=S.

A "cyanate" group is a radical of the formula: —OCN.

A "thiocyanate" group is a radical of the formula: —SCN.

A "thioether" group is a radical of the formula; —S(R#), wherein R# is as defined above.

A "thiocarbonyl" group is a radical of the formula: —C(=S)(R#), wherein R# is as defined above.

A "sulfinyl" group is a radical of the formula: —S(=O)(R#), wherein R# is as defined above.

A "sulfone" group is a radical of the formula: —S(=O)$_2$(R#), wherein R# is as defined above.

A "sulfonylamino" group is a radical of the formula: —NHSO$_2$(R#) or —N(alkyl)SO$_2$(R#), wherein each alkyl and R# are defined above.

A "sulfonamide" group is a radical of the formula: —S(=O)$_2$N(R#)$_2$, or —S(=O)$_2$NH(R#), or —S(=O)$_2$NH$_2$, wherein each R# is independently as defined above.

A "phosphonate" group is a radical of the formula: —P(=O)(O(R#))$_2$, —P(=O)(OH)$_2$, —OP(=O)(O(R#))(R#), or —OP(=O)(OH)(R#), wherein each R# is independently as defined above.

A "phosphine" group is a radical of the formula: —P(R#)$_2$, wherein each R# is independently as defined above.

When the groups described herein, with the exception of alkyl group are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Dihydropyrazino-Pyrazine Compound include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "clathrate" means a Dihydropyrazino-Pyrazine Compound, or a salt thereof, in the form of a crystal lattice that contains spaces (e.g., channels) that have a guest molecule (e.g., a solvent or water) trapped within or a crystal lattice wherein a Dihydropyrazino-Pyrazine Compound is a guest molecule.

As used herein and unless otherwise indicated, the term "solvate" means a Dihydropyrazino-Pyrazine Compound, or a salt thereof, that further includes a stoichiometric or non-stoichiometric amount of a solvent bound by non-covalent intermolecular forces. In one embodiment, the solvate is a hydrate.

As used herein and unless otherwise indicated, the term "hydrate" means a Dihydropyrazino-Pyrazine Compound, or a salt thereof, that further includes a stoichiometric or non-stoichiometric amount of water bound by non-covalent intermolecular forces.

As used herein and unless otherwise indicated, the term "prodrug" means a Dihydropyrazino-Pyrazine Compound derivative that can hydrolyze, oxidize, or otherwise react under biological conditions (in vitro or in vivo) to provide an active compound, particularly a Dihydropyrazino-Pyrazine Compound. Examples of prodrugs include, but are not limited to, derivatives and metabolites of a Dihydropyrazino-Pyrazine Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a Dihydropyrazino-Pyrazine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Dihydropyrazino-Pyrazine Compounds can have chiral centers and can occur as racemates, individual enantiomers or diastereomers, and mixtures thereof. All such isomeric forms are included within the embodiments disclosed herein, including mixtures thereof. The use of stereomerically pure forms of such Dihydropyrazino-Pyrazine Compounds, as well as the use of mixtures of those forms are encompassed by the embodiments disclosed herein. For example, mixtures comprising equal or unequal amounts of the enantiomers of a particular Dihydropyrazino-Pyrazine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Dihydropyrazino-Pyrazine Compounds can include E and Z isomers, or a mixture thereof, and cis and trans isomers or a mixture thereof. In certain embodiments, the Dihydropyrazino-Pyrazine Compounds are isolated as either the cis or trans isomer. In other embodiments, the Dihydropyrazino-Pyrazine Compounds are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

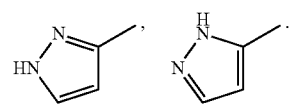

As readily understood by one skilled in the art, a wide variety of functional groups and other structures may exhibit tautomerism and all tautomers of the Dihydropyrazino-Pyrazine Compounds are within the scope of the present invention.

It should also be noted the Dihydropyrazino-Pyrazine Compounds can contain unnatural proportions of atomic isotopes at one or more of the atoms. For example, the compounds may be radiolabeled with radioactive isotopes, such as for example tritium ($^3$H), iodine-125 ($^{125}$I) sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Dihydropyrazino-Pyrazine Compounds as described herein, whether radioactive or not, are intended to be encompassed within the scope of the embodiments provided herein. In some embodiments, there are provided isotopologues of the Dihydropyrazino-Pyrazine Compounds, for example, the isotopologues are deuterium, carbon-13, or nitrogen-15 enriched Dihydropyrazino-Pyrazine Compounds.

It should be noted that if there is a discrepancy between a depicted structure and a name for that structure, the depicted structure is to be accorded more weight.

The B-cell disorders chronic lymphocytic leukemia/small lymphocytic lymphoma (CLL/SLL) represent two ends of a spectrum of the same disease process differing in the degree of blood/marrow involvement (CLL) versus lymph node involvement (SLL). Chronic lymphocytic leukemia is the most common leukemia in the U.S. and is typically characterized immunophenotypically as CD5+, CD23+, CD10−, CD19+, CD20 dim, sIg dim, and cyclin D1−(the latter point a distinguishing feature from mantle cell lymphoma).

T-cell-prolymphocytic leukemia (T-PLL) is a mature T-cell leukemia with aggressive behavior and predilection for blood, bone marrow, lymph nodes, liver, spleen, and skin involvement. T-PLL is a very rare leukemia, primarily affecting adults over the age of 30. It represents 2% of all small lymphocytic leukemias in adults. T-PLL has the immunophenotype of a mature (post-thymic) T-lymphocyte, and the neoplastic cells are typically positive for pan-T antigens CD2, CD3, and CD7 and negative for TdT and CD1a. The immunophenotype CD4+/CD8− is present in 60% of cases, the CD4+/CD8+ immunophenotype is present in 25%, and the CD4−/CD8+ immunophenotype is present in 15% of cases The term "ATM" as used herein, refers to Ataxia Telangiectasia Mutated (ATM), a serine/threonine protein kinase that is recruited and activated by DNA double-strand breaks. ATM phosphorylates several key proteins that initiate activation of the DNA damage checkpoint, leading to cell cycle arrest, DNA repair or apoptosis. Several of these targets, including p53, CHK2 and H2AX are tumor suppressors. The ATM gene codes for a 350 kDa protein consisting of 3056 amino acids.

The term, "deletion of 11q" or "del11 q22" as used herein, refers to deletion of all or part of the long arm of chromosome 11 containing the ATM gene within tumor cells.

"Treating" as used herein, means an alleviation, in whole or in part, of CLL or T-PLL, or a symptom thereof, or slowing, or halting of further progression or worsening of CLL or T-PLL or a symptom thereof. In some embodiments, the CLL is a CLL characterized by deletion of all or part of chromosome 11q, loss or mutation of the gene encoding ATM (including biallelic ATM mutations), loss of ATM expression or function, mutation of IgVH, wild type IgVH, wild type p53/ATM, mutation of p53, dysfunctional p53 or Zap-70 positivity. In other embodiments, the CLL is characterized as the small lymphocytic lymphoma (SLL) variant of CLL. In some embodiments, the CLL is characterized by deletion of all or part of chromosome 11q. In other embodiments, the CLL is characterized by deletion of chromosome 11q22. In others, the CLL is characterized by loss or mutation of the gene encoding ATM. In yet others, the CLL is characterized by loss of ATM expression or function. In some embodiments, the T-PLL is characterized by deletion of all or part of chromosome 11q, loss or mutation of the gene encoding ATM (including biallelic ATM mutations), loss of ATM expression or function, mutation of IgVH, wild type IgVH, wild type p53/ATM, mutation of p53, dysfunctional p53 or Zap-70 positivity. In some embodiments, the T-PLL is characterized by deletion of all or part of chromosome 11q. In other embodiments, the T-PLL is characterized by deletion of chromosome 11q22. In others, the T-PLL is characterized by loss or mutation of the gene encoding ATM. In yet others, the T-PLL is characterized by loss of ATM expression or function.

"Preventing" as used herein, means the prevention of the onset, recurrence or spread, in whole or in part, of CLL or T-PLL. In some embodiments, the CLL is a CLL characterized by deletion of all or part of chromosome 11q, loss or mutation of the gene encoding ATM (including biallelic ATM mutations), loss of ATM expression or function, mutation of IgVH, wild type IgVH, wild type p53/ATM, mutation of p53, dysfunctional p53 or Zap-70 positivity. In some embodiments, the CLL is characterized by deletion of all or part of chromosome 11q. In other embodiments, the CLL is characterized by deletion of chromosome 11q22. In others, the CLL is characterized by loss or mutation of the gene encoding ATM. In yet others, the CLL is characterized by loss of ATM expression or function. In some embodiments, the T-PLL is characterized by deletion of all or part of chromosome 11q, loss or mutation of the gene encoding ATM (including biallelic ATM mutations), loss of ATM expression or function, mutation of IgVH, wild type IgVH, wild type p53/ATM, mutation of p53, dysfunctional p53 or Zap-70 positivity. In some embodiments, the T-PLL is characterized by deletion of all or part of chromosome 11q. In other embodiments, the T-PLL is characterized by deletion of chromosome 11q22. In others, the T-PLL is characterized by loss or mutation of the gene encoding ATM. In yet others, the T-PLL is characterized by loss of ATM expression or function.

The term "effective amount" in connection with a Dihydropyrazino-Pyrazine Compound means an amount capable of alleviating, in whole or in part, symptoms associated with CLL or T-PLL, or slowing or halting further progression or worsening of those symptoms, or treating or preventing CLL or T-PLL. The effective amount of the Dihydropyrazino-Pyrazine Compound, for example in a pharmaceutical composition, may be at a level that will exercise the desired effect; for example, about 0.005 mg/kg of a subject's body weight to about 100 mg/kg of a patient's body weight in unit dosage for both oral and parenteral administration. As will be apparent to those skilled in the art, it is to be expected that the effective amount of a Dihydropyrazino-Pyrazine Compound disclosed herein may vary depending on the severity of the indication being treated. In some embodiments, the CLL is characterized by deletion of all or part of chromosome 11q. In other embodiments, the CLL is characterized by deletion of chromosome 11q22. In others, the CLL is characterized by loss or mutation of the gene encoding ATM (including biallelic ATM mutations). In yet others, the CLL is characterized by loss of ATM expression or function. In some embodiments, the T-PLL is characterized by deletion of all or part of chromosome 11q. In other embodiments, the T-PLL is characterized by deletion of chromosome 11q22. In others, the T-PLL is characterized by loss or mutation of the gene encoding ATM (including biallelic ATM mutations). In yet others, the T-PLL is characterized by loss of ATM expression or function.

The terms "patient" and "subject" as used herein include an animal, including, but not limited to, an animal such as a cow, monkey, horse, sheep, pig, chicken, turkey, quail, cat, dog, mouse, rat, rabbit or guinea pig, in one embodiment a mammal, in another embodiment a human. In one embodiment, a "patient" or "subject" is a human having CLL or T-PLL. In one embodiment, a patient is a human having histologically or cytologically-confirmed CLL or T-PLL, including subjects who have progressed on (or not been able to tolerate) standard anticancer therapy or for whom no standard anticancer therapy exists. In one embodiment, the patient is a human having CLL or T-PLL. In one embodiment, the patient is a human having CLL or T-PLL characterized by deletion of all or part of chromosome 11q. In other embodiments, the CLL or T-PLL is characterized by deletion of chromosome 11q22. In others, the CLL or T-PLL is characterized by loss or mutation of the gene encoding ATM (including biallelic ATM mutations). In yet others, the CLL or T-PLL is characterized by loss of ATM expression or function. In one embodiment, the patient is a human having CLL or T-PLL characterized by deletion of all or part of chromosome 11q, measured by fluorescence in situ hybridization (FISH) or gene sequencing. In another embodiment, the patient is a human having CLL or T-PLL characterized by loss of the gene encoding ATM measured by FISH. In another embodiment, the patient is a human having CLL or T-PLL characterized by mutation of the gene encoding ATM measured by gene sequencing. In another embodiment, the patient is a human having CLL or T-PLL characterized by loss of ATM expression measured by immunohistochemistry (IHC) or Western Blot. In another embodiment, the patient is a human having CLL or T-PLL characterized by ATM function loss due to mutation, measured by gene sequencing. In one embodiment, the patient is a human having CLL or T-PLL characterized by deletion of all or part of chromosome 11q, loss or mutation of the gene encoding ATM (including biallelic mutations), loss of ATM expression or function, mutation of IgVH, wild type IgVH, wild type p53/ATM, mutation of p53, dysfunctional p53 or Zap-70 positivity.

In certain embodiments, treatment of CLL or T-PLL may be assessed by the inhibition of phosphorylation of S6RP, 4E-BP1 and/or AKT in circulating blood cells and/or skin biopsies, before, during and/or after treatment with a Dihydropyrazino-Pyrazine Compound. In other embodiments, treatment of CLL or T-PLL may be assessed by the inhibition of DNA-PK activity in skin samples and/or tumor biopsies/aspirates, such as by assessment of the amount of pDNA-PK 52056 as a biomarker for DNA damage pathways, before, during, and/or after Dihydropyrazino-Pyrazine Compound treatment. In one embodiment, the skin sample is irradiated by UV light. In the extreme, complete inhibition, is referred to herein as prevention or chemoprevention. In this context, the term "prevention" includes either preventing the onset of clinically evident CLL or T-PLL altogether or preventing the onset of a preclinically evident stage of CLL or T-PLL altogether or preventing the onset of a preclinically evident stage of CLL or T-PLL.

In certain embodiments, the treatment of CLL or T-PLL may be assessed by the International Workshop Criteria (IWC) for malignant lymphoma (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
| --- | --- | --- | --- | --- |
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohisto-chemistry should be negative |
| PR | Regression of measurable disease and no new sites | ≥50% decrease in SPD of up to 6 largest dominant masses; no increase in size of other nodes (a) FDG-avid or PET positive prior to therapy; one or more PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET (b) Variably FDG-avid | | |

-continued

| Response | Definition | Nodal Masses | Spleen, liver | Bone Marrow |
|---|---|---|---|---|
| PD or relapsed disease | Any new lesion or increase by ≥50% of previously involved sites from nadir | or PET negative; no change in size of previous lesions on CT Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations:
CR, complete remission;
FDG, [$^{18}$F]fluorodeoxyglucose;
PET, positron emission tomography;
CT, computed tomography;
PR, partial remission;
SPD, sum of the product of the diameters;
SD, stable disease;
PD, progressive disease.

| End point | Patients | Definition | Measured from |
|---|---|---|---|
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission

In certain embodiments, the treatment of CLL or T-PLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
|---|---|---|---|
| Group A | | | |
| Lymphadenopathy† | None >1.5 cm | Decrease ≥50% | Increase ≥50% |
| Hepatomegaly | None | Decrease ≥50% | Increase ≥50% |
| Splenomegaly | None | Decrease ≥50% | Increase ≥50% |
| Blood lymphocytes | <4000/µL | Decrease ≥50% from baseline | Increase ≥50% over baseline |
| Marrow‡ | Normocellular, <30% lymphocytes, no B-lymphoid nodules. | 50% reduction in marrow infiltrate, or B-lymphoid nodules | |

| Parameter | CR | PR | PD |
|---|---|---|---|
| | Hypocellular marrow defines CRi (5.1.6). | | |
| Group B | | | |
| Platelet count | >100 000/μL | >100 000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils‡ | >1500/μL | >1500/μL or >50% improvement over baseline | |

Group A criteria define the tumor load; Group B criteria define the function of the hematopoietic system (or marrow). CR (complete remission): all of the criteria have to be met, and patients have to lack disease-related constitutional symptoms; PR (partial remission): at least two of the criteria of group A plus one of the criteria of group B have to be met; SD is absence of progressive disease (PD) and failure to achieve at least a PR; PD: at least one of the above criteria of group A or group B has to be met. Sum of the products of multiple lymph nodes (as evaluated by CT scans in clinical trials, or by physical examination in general practice). These parameters are irrelevant for some response categories.

In one embodiment, the end point for CLL or T-PLL is evidence of clinical benefit. Clinical benefit may reflect improvement in quality of life, or reduction in patient symptoms, transfusion requirements, frequent infections, or other parameters. Time to reappearance or progression of CLL- or T-PLL-related symptoms can also be used in this end point.

In certain embodiments, treatment of CLL or T-PLL may be assessed by the inhibition of phosphorylation of S6RP, 4E-BP1, AKT and/or DNA-PK in circulating blood and/or tumor cells, and/or skin biopsies or tumor biopsies/aspirates, before, during and/or after treatment with a TOR kinase inhibitor, for example, a Dihydropyrazino-Pyrazine Compound. For example, the inhibition of phosphorylation of S6RP, 4E-BP1, AKT and/or DNA-PK is assessed in B-cells, T-cells and/or monocytes.

In other embodiments, treatment of CLL or T-PLL may be assessed by the inhibition of DNA-PK activity in skin samples and/or tumor biopsies/aspirates, such as by assessment of the amount of pDNA-PK 52056 as a biomarker for DNA damage pathways, before, during, and/or after TOR kinase inhibitor treatment, for example, a Dihydropyrazino-Pyrazine Compound. In one embodiment, the skin sample is irradiated by UV light.

In the extreme, complete inhibition, is referred to herein as prevention or chemoprevention. In this context, the term "prevention" includes either preventing the onset of clinically evident CLL or T-PLL altogether or preventing the onset of a preclinically evident stage of CLL or T-PLL. Also intended to be encompassed by this definition is the prevention of transformation into malignant cells or to arrest or reverse the progression of premalignant cells to malignant cells. This includes prophylactic treatment of those at risk of developing CLL or T-PLL.

4.2 Brief Description of the Drawings

FIG. 1A provides the toxicity of Compound 1 and etoposide on CLL cells.

Figure 1B:
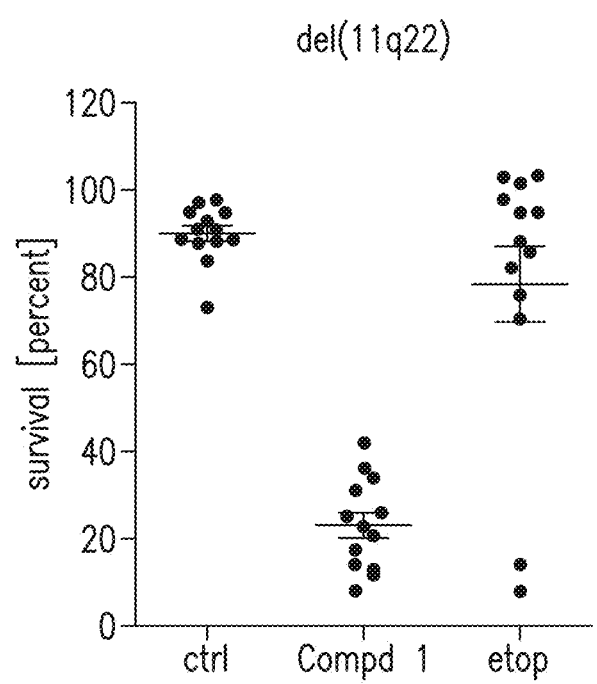

FIG. 1B provides the toxicity of Compound 1 and etoposide on ATM-deficient CLL cells.

Figure 2A:
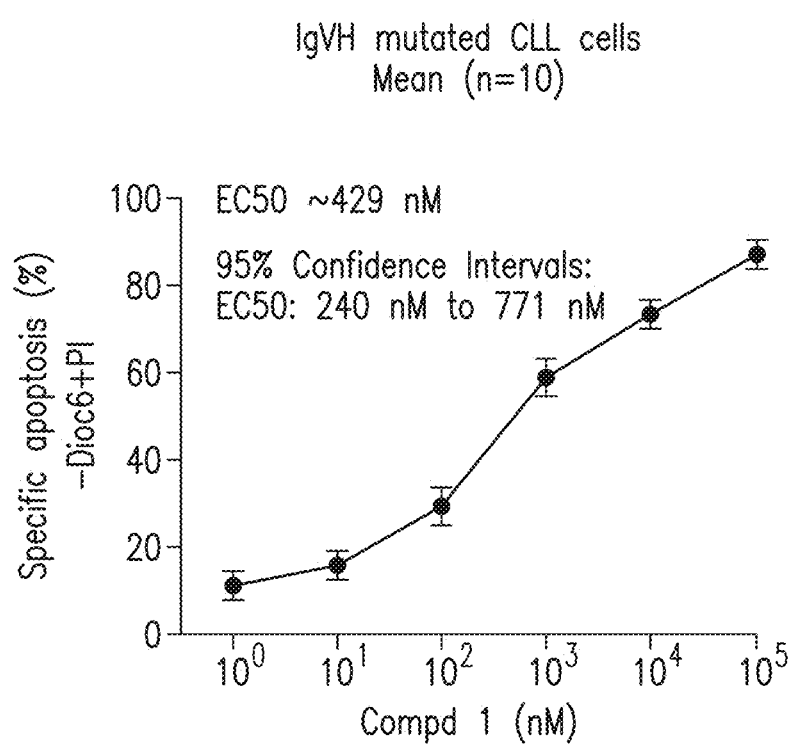

FIG. 2A provides the toxicity of Compound 1 as measured by the induction of apoptosis on IgVH-mutated CLL.

Figure 2B:
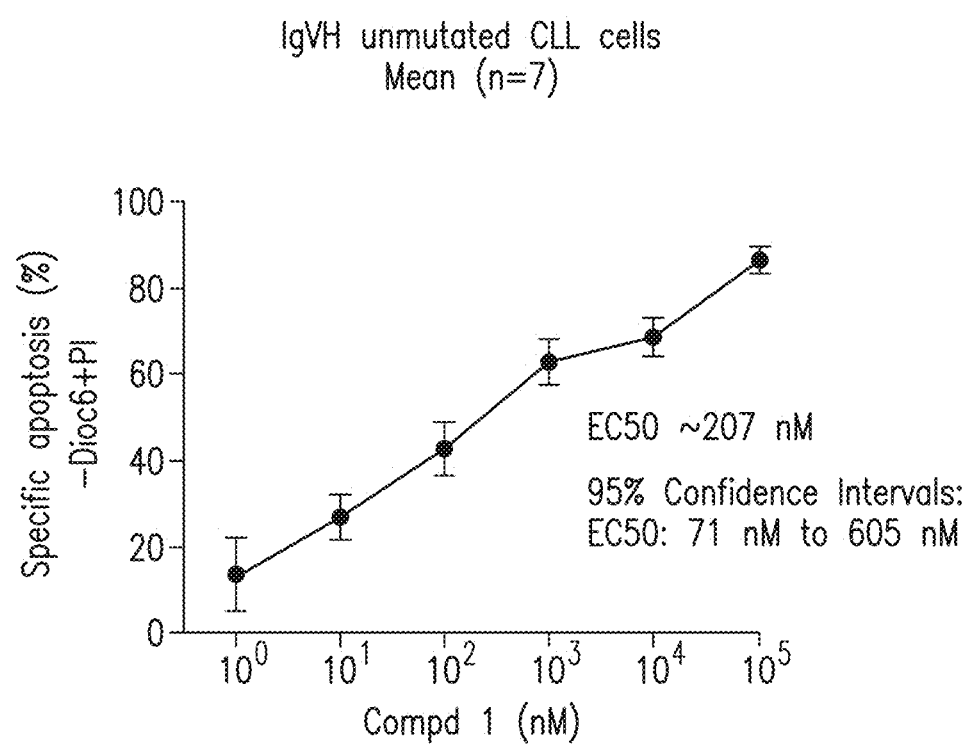

FIG. 2B provides the toxicity of Compound 1 as measured by the induction of apoptosis on IgVH-unmutated CLL.

Figure 2C:
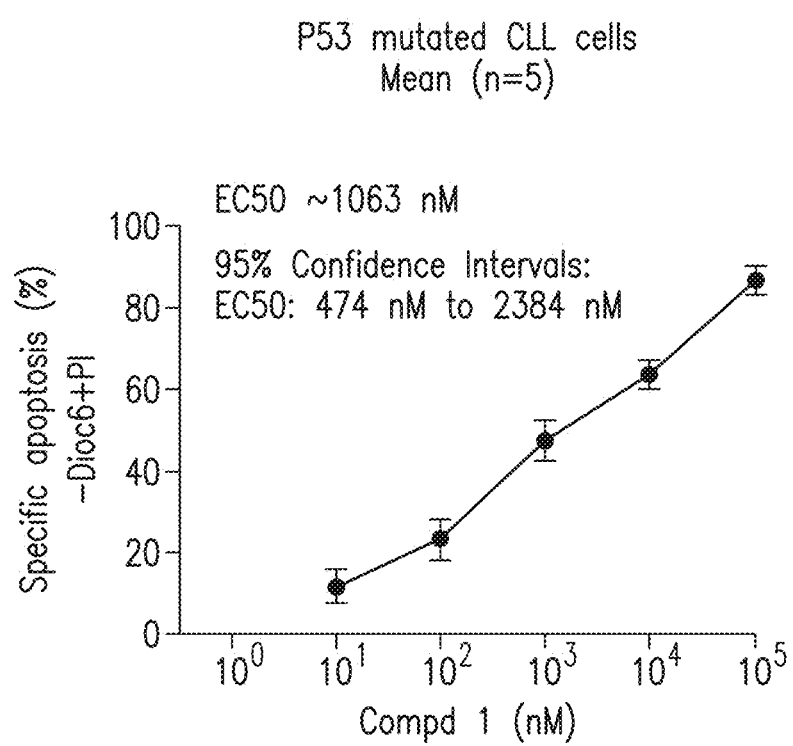

FIG. 2C provides the toxicity of Compound 1 as measured by the induction of apoptosis on p53 dysfunctional CLL.

Figure 2D:
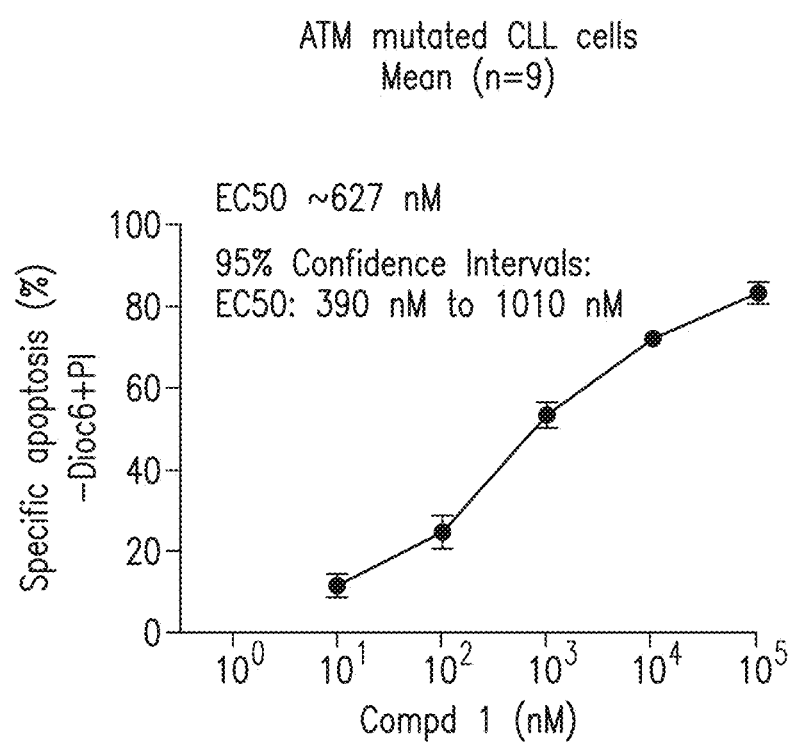

FIG. 2D provides the toxicity of Compound 1 as measured by the induction of apoptosis on ATM mutated CLL.

Figure 2E:
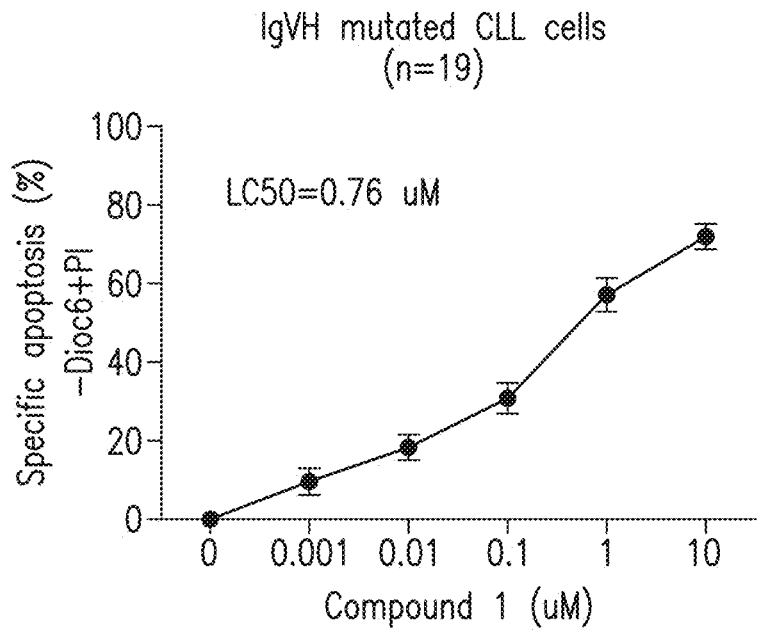

FIG. 2E provides the toxicity of Compound 1 as measured by the induction of apoptosis on IgVH-mutated CLL.

Figure 2F:
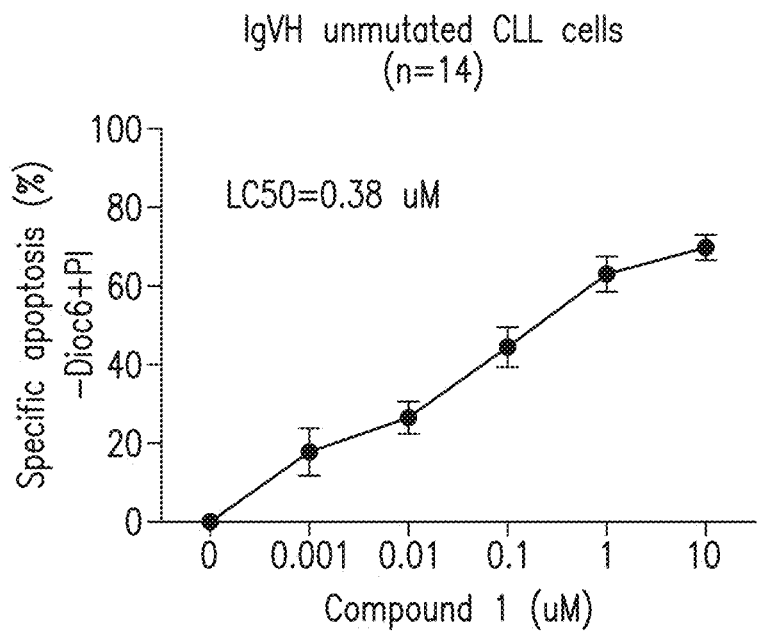

FIG. 2F provides the toxicity of Compound 1 as measured by the induction of apoptosis on IgVH-unmutated CLL.

Figure 2G:
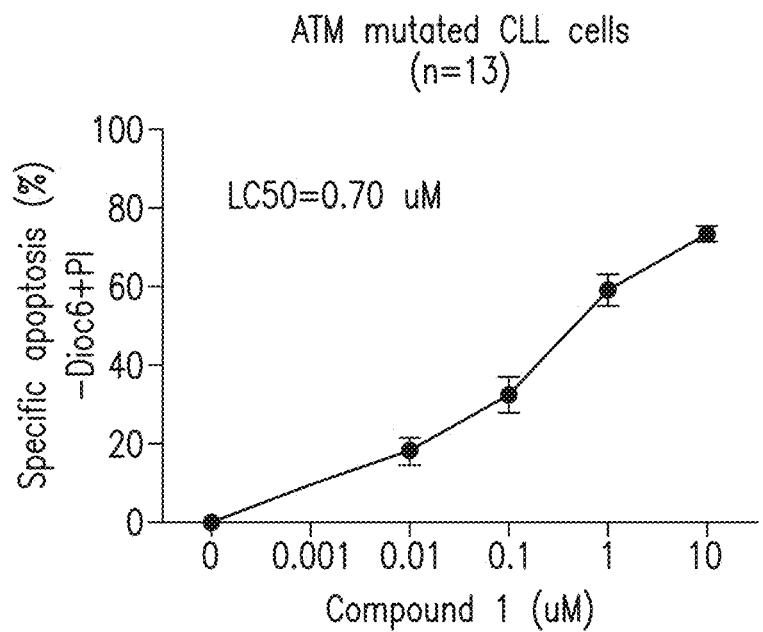

FIG. 2G provides the toxicity of Compound 1 as measured by the induction of apoptosis on ATM mutated CLL.

Figure 2H:
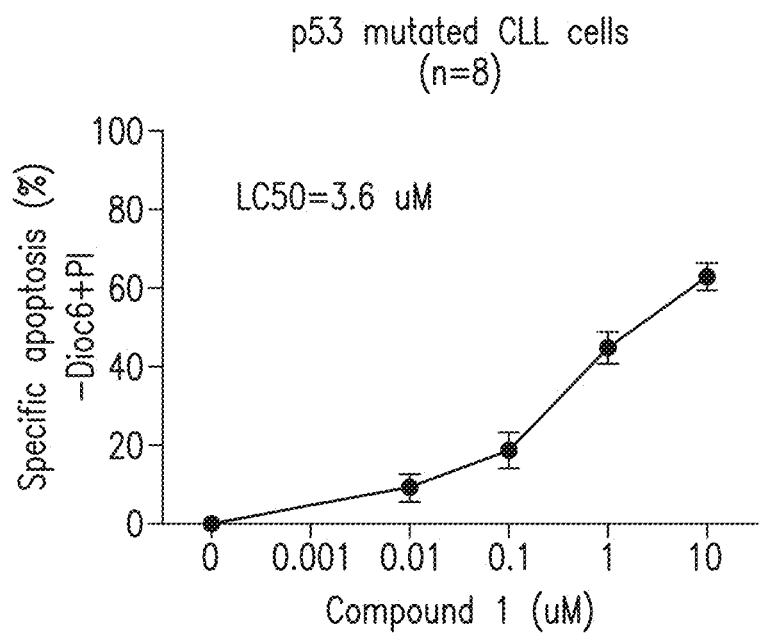

FIG. 2H provides the toxicity of Compound 1 as measured by the induction of apoptosis on p53 dysfunctional CLL.

Figure 3A:
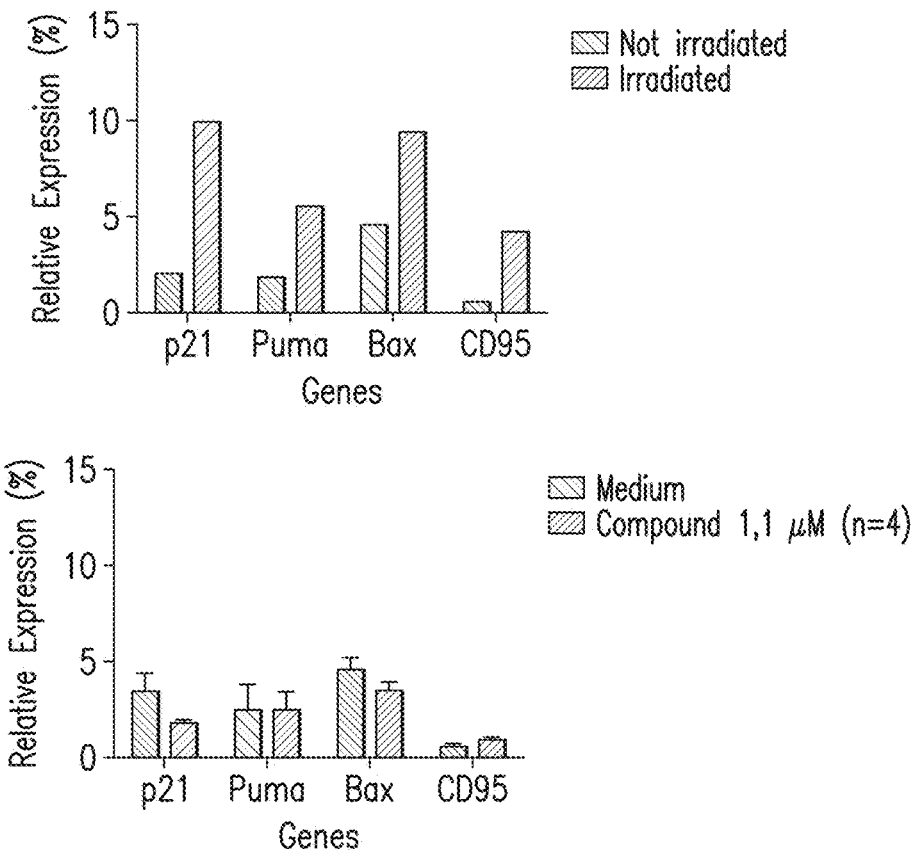
Figure 3B:
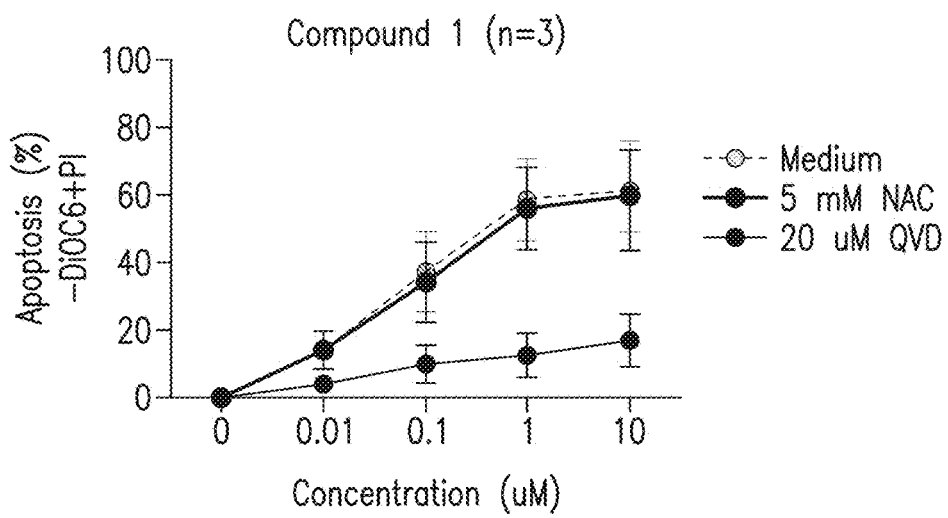

FIGS. 3A and 3B: Compound 1-induced cytotoxicity is p53 independent and caspase dependent. FIG. 3A) mRNA levels of pro-/anti-apoptotic mediators in CLL cells treated with or without 1 μM Compound 1 for 24 hours was measured by RT-MLPA (upper panel). As positive control, CLL cells were irradiated with 5Gy (lower panel). FIG. 3B) CLL cells were cultured with 20 μM QvD or 5 mM NAC and with increasing concentrations of Compound 1 for 48 hours. Apoptosis levels were measured by Flow using DiOC6/PI staining and specific apoptosis was calculated. Results are shown as mean±SEM.

Figure 4:
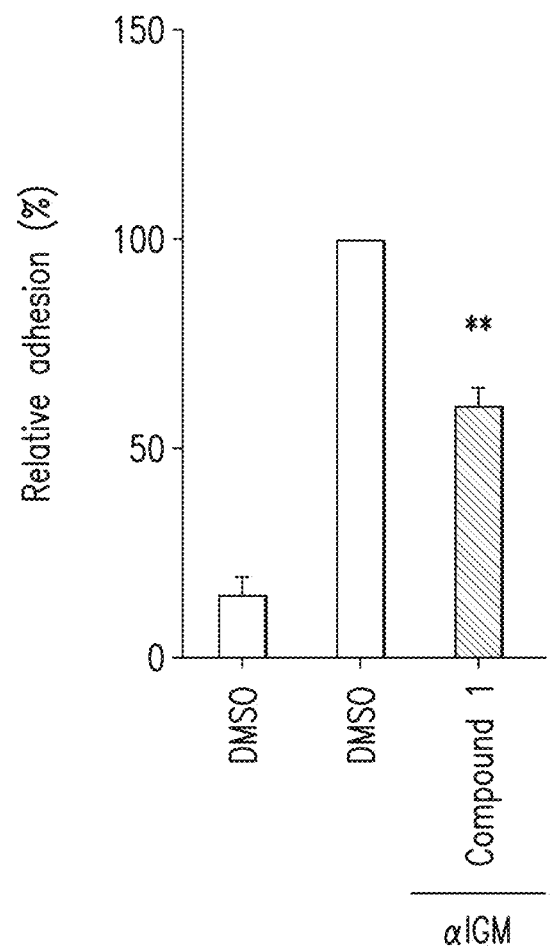

FIG. 4: CLL cells pretreated with 1 μM Compound 1 were stimulated with αIgM and allowed to adhere to fibronectin-coated surfaces (n=5). Graphs are presented as normalized mean±SEM (100%=stimulated cells without inhibitors). *0.01≤P<0.05; **0.001≤P<0.01 (paired one sample T test) (n=5).

Figure 5A:
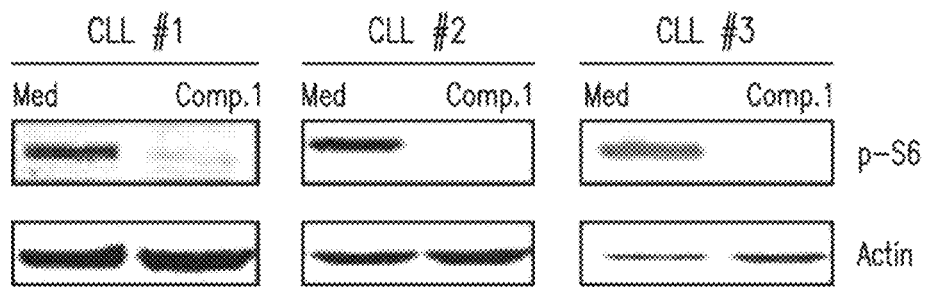
Figure 5B:
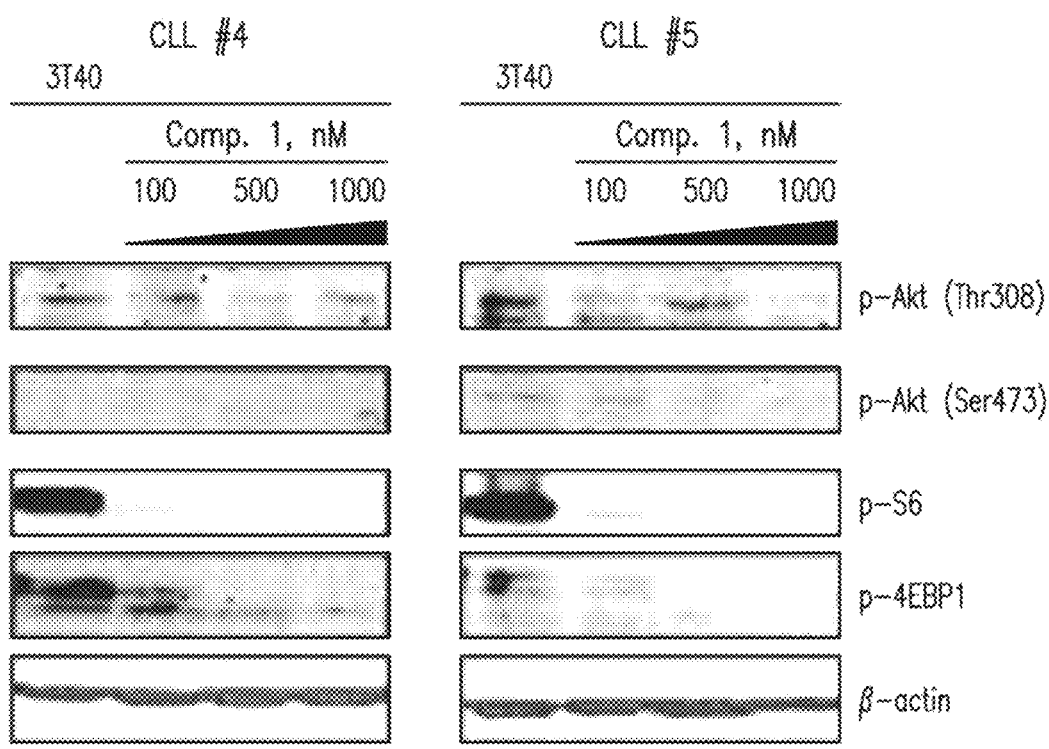

FIGS. 5A and 5B: Blocking of the mTOR pathway by Compound 1. FIG. 5A) CLL cells were cultured in the presence or absence of 1 μM Compound 1 for 2 hours. Protein lysates were probed for phospho-S6 and actin for loading control. Blots from three representative CLL samples are shown, of a total of five analyzed. FIG. 5B) CLL cells were cultured on 3T3 or CD40L-expressing 3T3 cells in the presence or absence of 100, 500 or 1000 nM Compound 1 for 72 hours. Blots were probed for p-Akt(Thr308), p-Akt (Ser473), p-S6, p-4EBP1 and actin for loading control. Blots from two representative CLL samples shown, of a total of four analyzed.

Figure 6A:
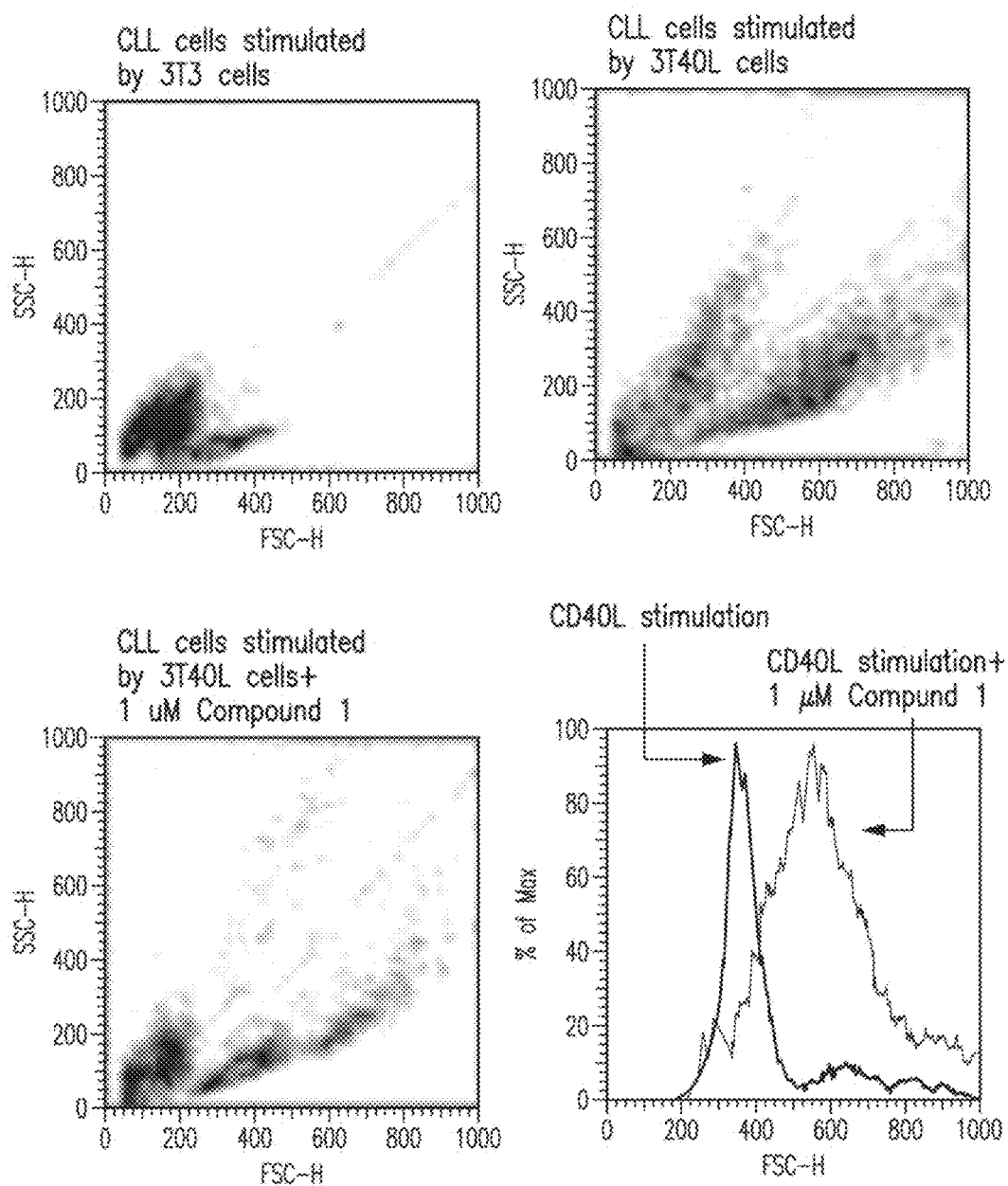
Figure 6B:
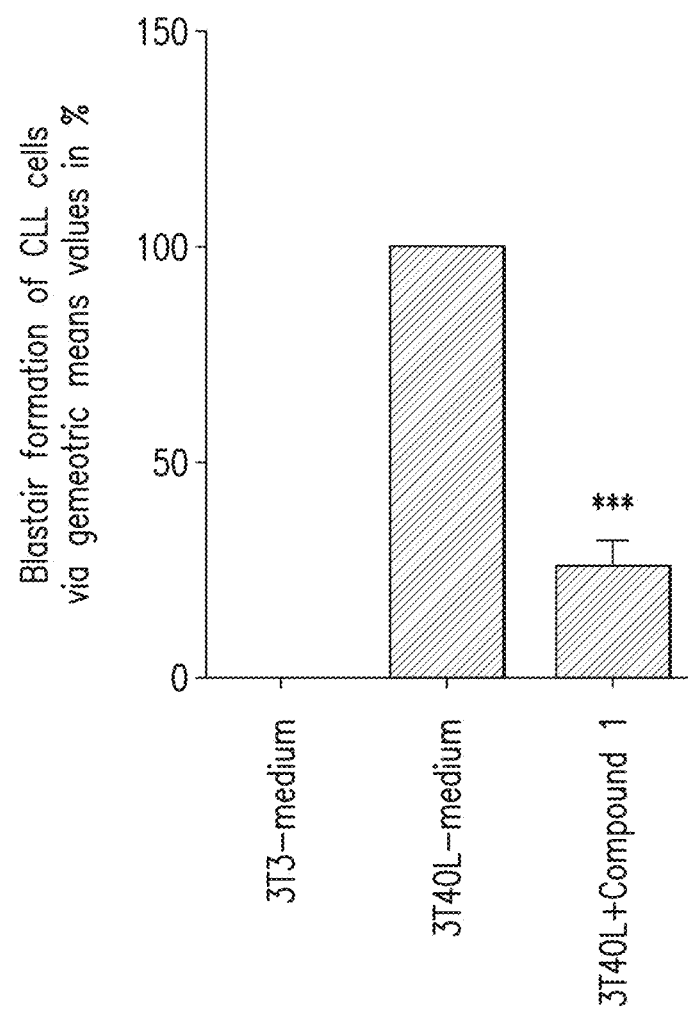
Figure 6C:
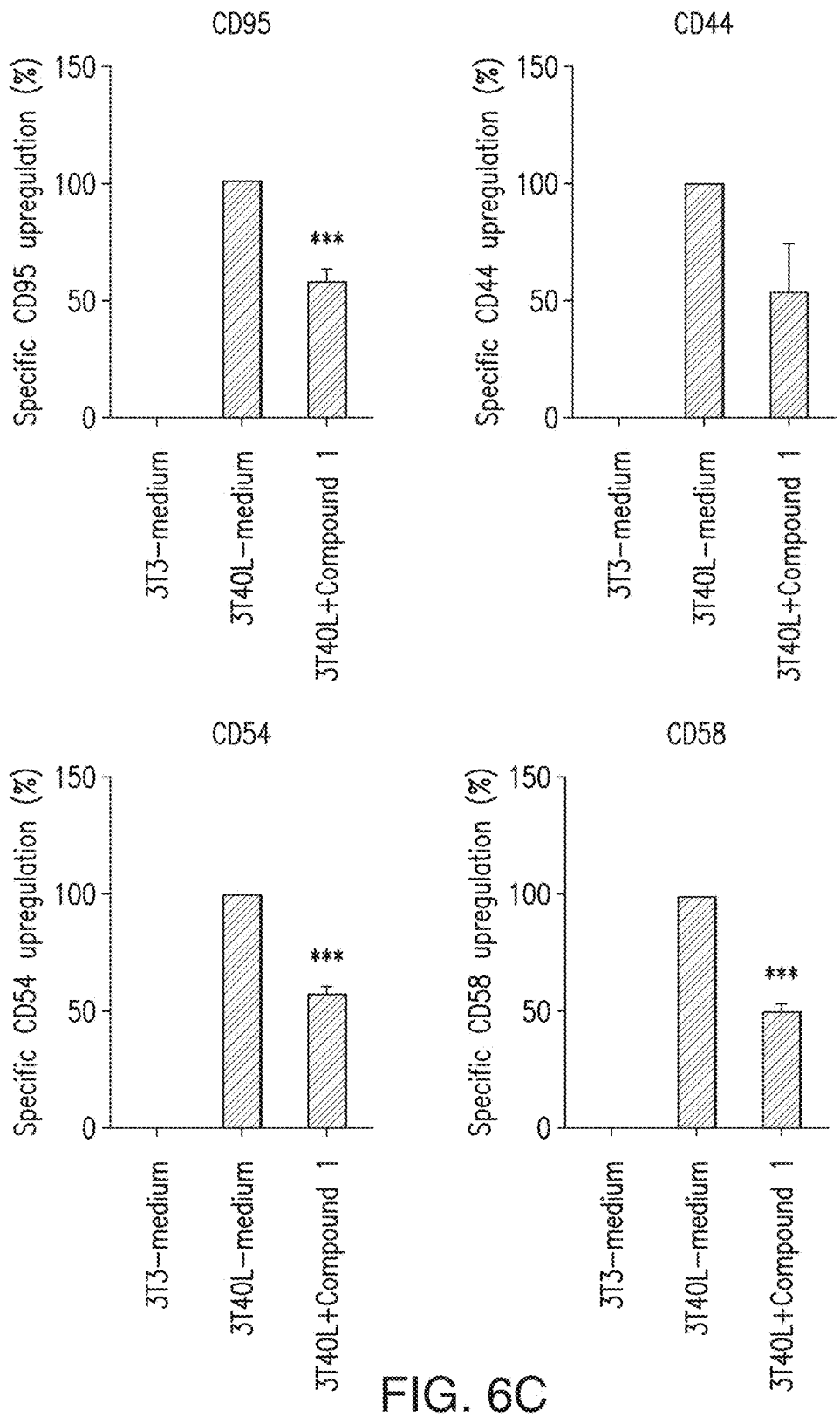

FIGS. 6A, 6B and 6C: Compound 1 blocks CD40-mediated activation of CLL cells. CLL cells were cultured on fibroblast expressing CD40L in the absence or presence of 1 μM of Compound 1 for 3 days. FIG. 6A and FIG. 6B) Blast cell formation was assessed by FACS analysis and results are shown as mean±SEM. *$0.01 \leq P<0.05$; $0.001 \leq P<0.01$; *$P<0.001$ (paired one sample T test) FIG. 6C) CLL cells were examined for surface expression of CD95 (Fas), CD44, CD54 (ICAM) and CD58 (LFA-3) by flow cytometry. Results are shown as mean±SEM (n=6).

Figure 7A:
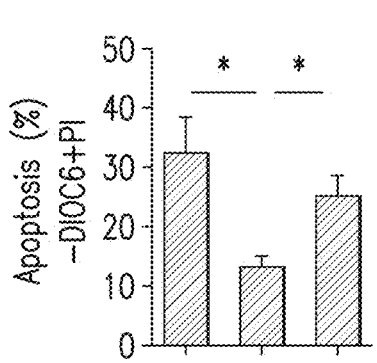
Figure 7B:
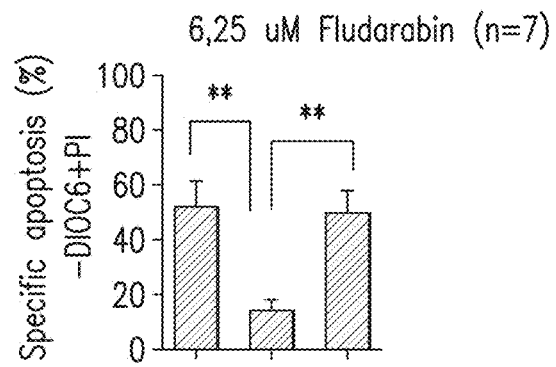
Figure 7C:
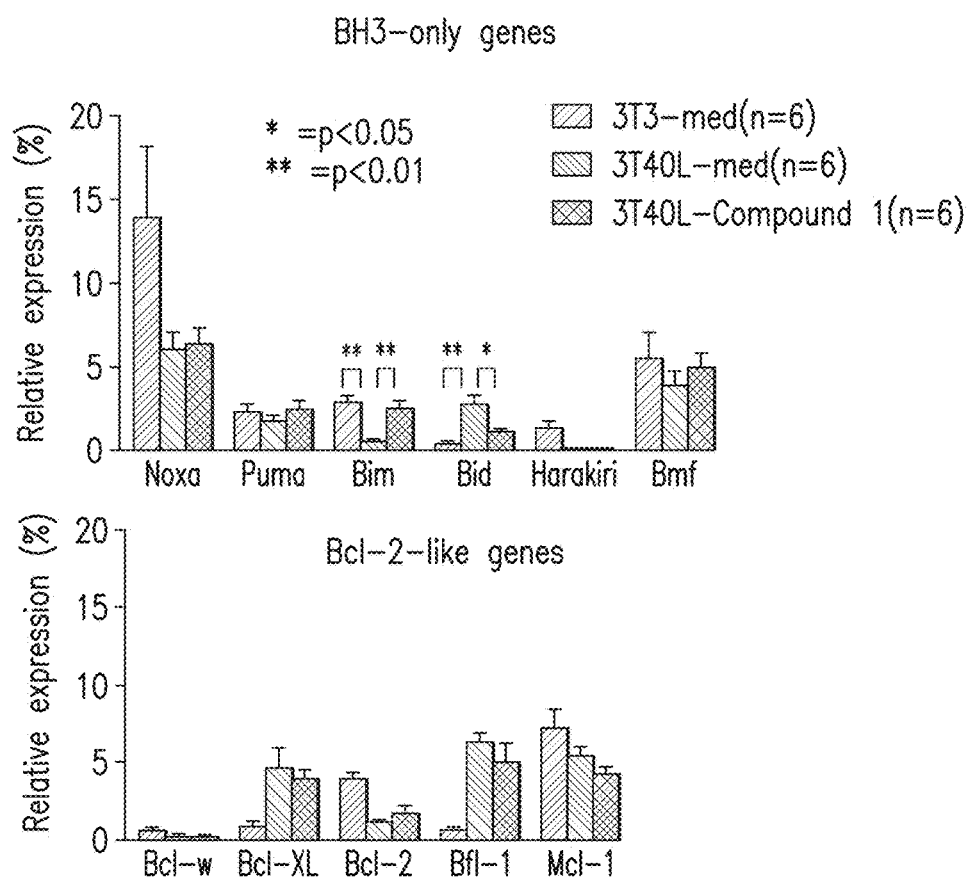
Figure 7D:
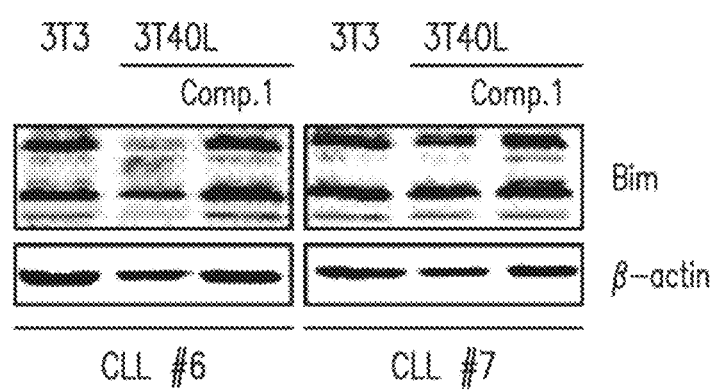

FIGS. 7A, 7B, 7C and 7D: CLL cells were cultured on fibroblast expressing CD40L and co-treated with 1 μM Compound 1 for 3 days. FIG. 7A) Apoptosis was assessed by DiOC6/PI staining and results are shown as mean±SEM (n=7). *$0.01 \leq P<0.05$; $0.001 \leq P<<0.01$; *$P<0.001$ (paired T test). FIG. 7B) After 3 days, fludarabine sensitivity assay was performed. Apoptosis was assessed by DiOC6/PI staining and specific apoptosis are shown as mean±SEM (n=7). *$0.01 \leq P<0.05$; $0.001 \leq P<0.01$ (paired T test) FIG. 7C) mRNA levels of pro-/anti-apoptotic mediators in CLL cells were measured by RT-MLPA (n=6). FIG. 7D**) Protein lysates were probed for Bim and actin for loading control. Blots from two representative CLL samples shown, of a total of four analyzed.

Figure 8A:
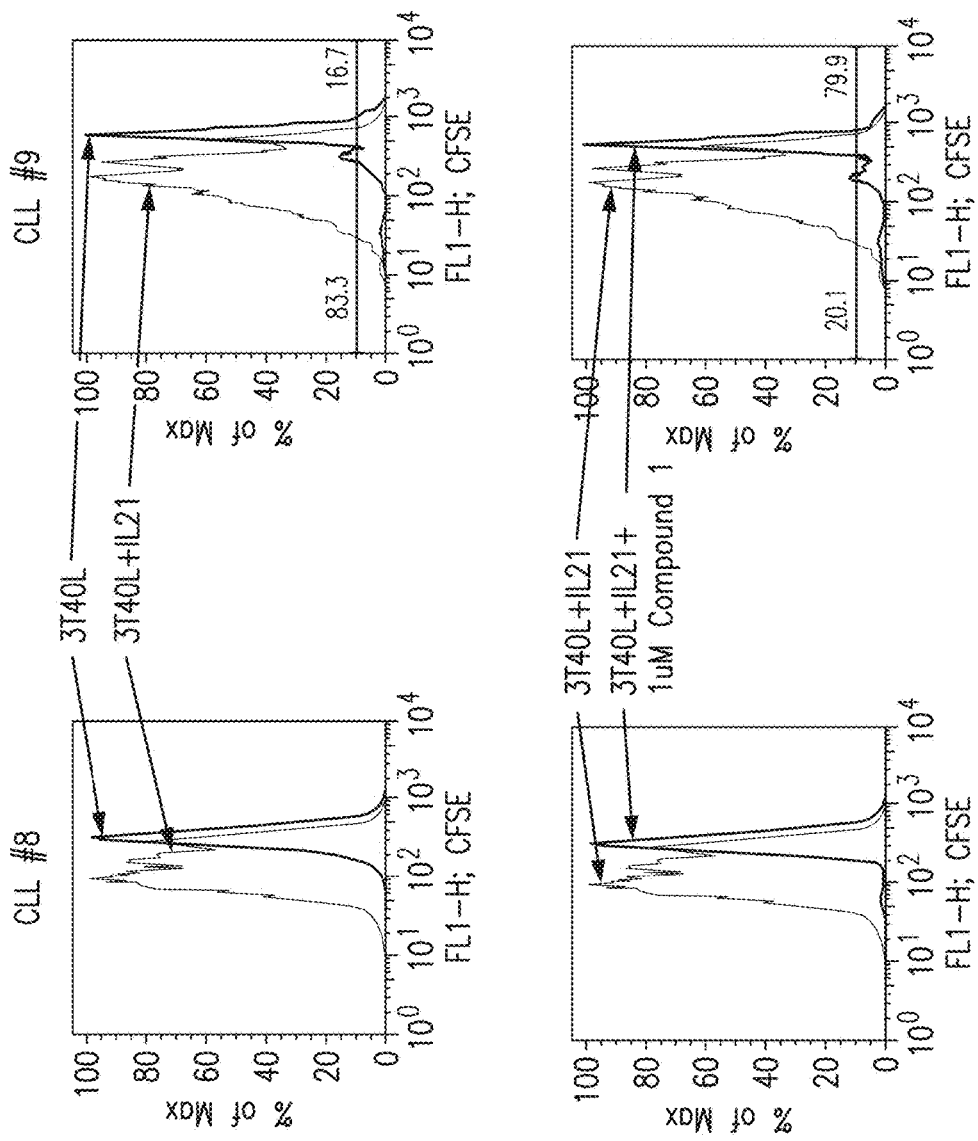
Figure 8B:
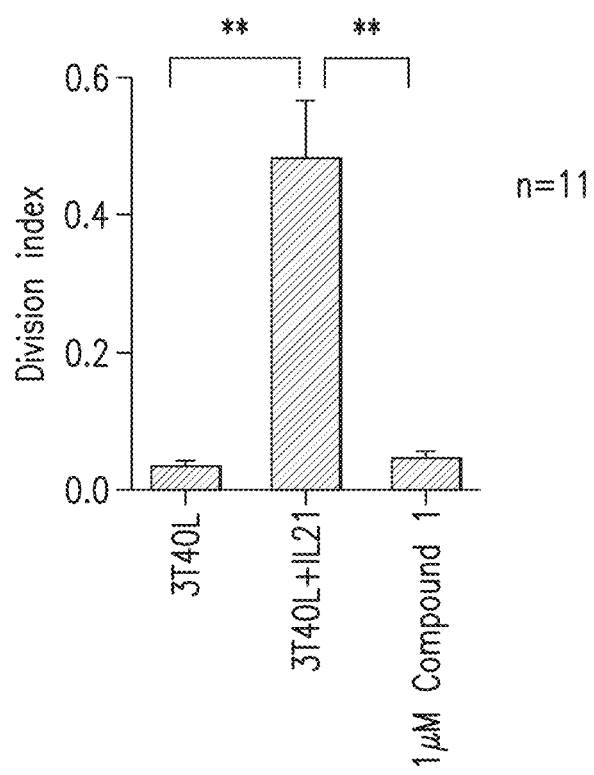

FIGS. 8A and 8B: Compound 1 completely blocks proliferation of CLL cells. FIG. 8A) CFSE labelled CLL cells were cultured on fibroblast expressing CD40L with (Blue line) or without (Red line) IL-21 and co-treated with 1 μM Compound 1 (Green line). After 4 days, CFSE was measured by FACS. Results are shown as representative histograms for 2 patients. FIG. 8B) Division index was calculated with FlowJo program. Results are shown as mean±SEM (n=11). *$0.01 \leq P<0.05$; **$0.001 \leq P<0.01$ (paired T test).

4.3 Dihydropyrazino-Pyrazine Compounds

The compounds provided herein are TOR kinase inhibitors, generally referred to as "Dihydropyrazino-Pyrazines" or "Dihydropyrazino-Pyrazine Compounds." In one aspect, the TOR kinase inhibitors do not include rapamycin or rapamycin analogs (rapalogs).

In one embodiment, the Dihydropyrazino-Pyrazine Compounds include compounds having the following formula (I):

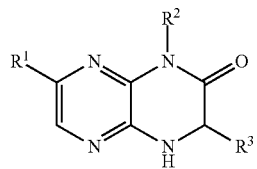

(I)

and pharmaceutically acceptable salts, clathrates, solvates, stereoisomers, tautomers, prodrugs, metabolites and isotopologues thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl, wherein in certain embodiments, the Dihydropyrazino-Pyrazine Compounds do not include 7-(4-hydroxyphenyl)-1-(3-methoxybenzyl)-3,4-dihydropyrazino[2,3-b]pyrazin-2(1H)-one, depicted below:

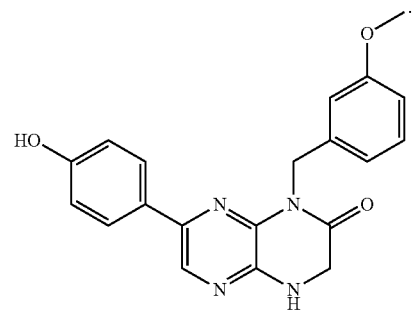 [SMILES: COc1cccc(CN2C(=O)CNc3ncc(-c4ccc(O)cc4)nc32)c1]

In some embodiments of compounds of formula (I), $R^1$ is substituted or unsubstituted aryl or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl or pyrazolyl), aminocarbonyl, halogen (for example, fluorine), cyano, hydroxyalkyl and hydroxy. In other embodiments, $R^1$ is pyridyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl), halogen, aminocarbonyl, cyano, hydroxyalkyl (for example, hydroxypropyl), —OR, and —$NR_2$, wherein each R is independently H, or a substituted or unsubstituted $C_{1-4}$ alkyl. In some embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In some embodiments, $R^1$ is

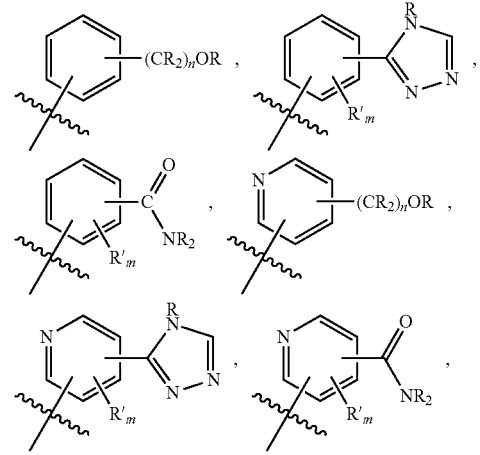

-continued

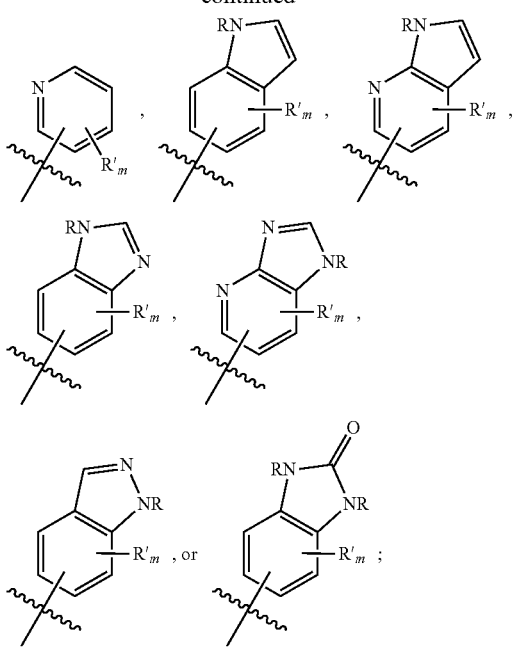

wherein R is at each occurrence independently H, or a substituted or unsubstituted $C_{1-4}$ alkyl (for example, methyl); R' is at each occurrence independently a substituted or unsubstituted $C_{1-4}$ alkyl (for example, methyl), halogen (for example, fluoro), cyano, —OR, or —NR$_2$; m is 0-3; and n is 0-3. It will be understood by those skilled in the art that any of the substituents R' may be attached to any suitable atom of any of the rings in the fused ring systems.

In some embodiments of compounds of formula (I), $R^1$ is

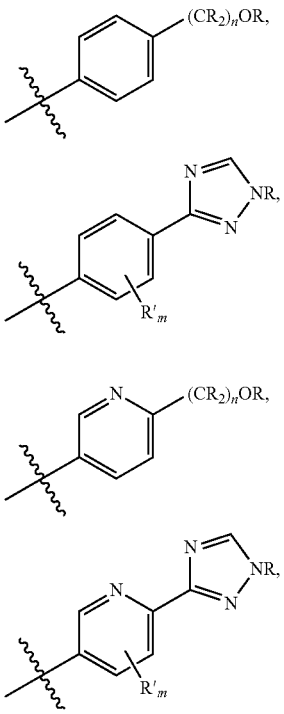

-continued

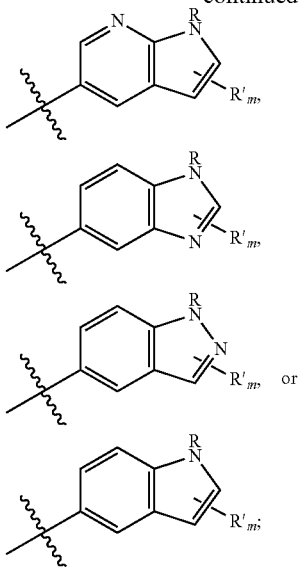

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR or —NR$_2$; m is 0-3; and n is 0-3.

In some embodiments of compounds of formula (I), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl) (OR),

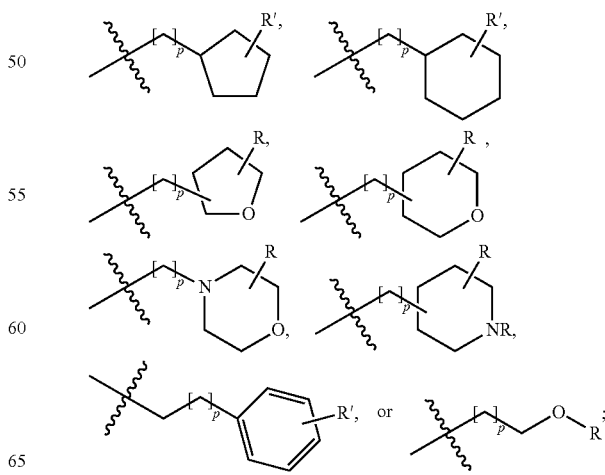

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In other embodiments of compounds of formula (I), $R^2$ is H, $C_{1-4}$ alkyl, $(C_{1-4}$alkyl)(OR),

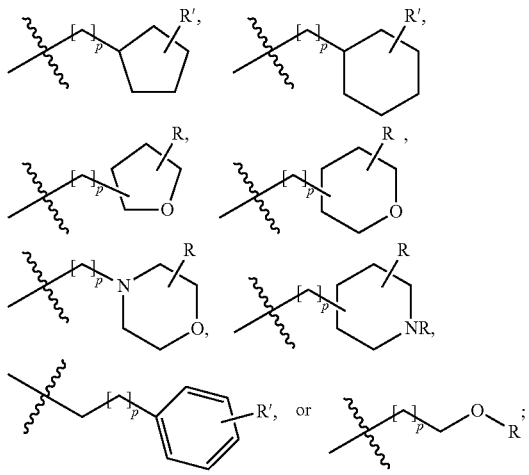

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In other embodiments of compounds of formula (I), $R^3$ is H.

In some such embodiments described herein, $R^1$ is substituted or unsubstituted aryl, or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridine, pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, aminocarbonyl, halogen, cyano, hydroxyalkyl and hydroxy. In others, $R^1$ is pyridyl substituted with one or more substituents independently selected from the group consisting of $C_{1-8}$ alkyl, substituted or unsubstituted heterocyclyl, halogen, aminocarbonyl, cyano, hydroxyalkyl, —OR, and —$NR_2$, wherein each R is independently H, or a substituted or unsubstituted $C_{1-4}$ alkyl. In still others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In one embodiment of compounds of formula (I), $R^1$ is phenyl, pyridyl, pyrimidyl, benzimidazolyl, 1H-pyrrolo[2,3-b]pyridyl, indazolyl, or indolyl, each optionally substituted. In some such embodiments, $R^1$ is phenyl substituted with one or more substituents independently selected from the group consisting of substituted or unsubstituted $C_{1-8}$ alkyl, substituted or unsubstituted heterocyclyl (for example, substituted or unsubstituted triazolyl), or halogen. In some other such embodiments, $R^1$ is pyridyl substituted with one or more substituents independently selected from the group consisting of substituted or unsubstituted $C_{1-8}$ alkyl, substituted or unsubstituted heterocyclyl (for example, substituted or unsubstituted triazolyl), halogen, aminocarbonyl, hydroxyalkyl, —OR, and —$NR_2$, wherein each R is independently H, or a substituted or unsubstituted $C_{1-4}$ alkyl. In some other such embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In some embodiments of compounds of formula (I), $R^2$ is H, substituted or unsubstituted $C_{1-8}$ alkyl, substituted or unsubstituted cycloalkyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. In some such embodiments, $R^2$ is H, methyl, ethyl, isopropyl, cyclohexyl, $(C_{1-4}$ alkyl)-phenyl, $(C_{1-4}$ alkyl)-cyclohexyl, (or $(C_{1-4}$ alkyl)-tetrahydropyranyl, each optionally substituted.

In some such embodiments of $R^2$, $R^1$ is phenyl, pyridyl, pyrimidyl, benzimidazolyl, 1H-pyrrolo[2,3-b]pyridyl, indazolyl, or indolyl, each optionally substituted. For example, $R^1$ is phenyl, substituted with one or more substituents independently selected from the group consisting of substituted or unsubstituted $C_{1-8}$ alkyl, substituted or unsubstituted heterocyclyl (for example, substituted or unsubstituted triazolyl), or halogen. In some other such embodiments, $R^1$ is pyridyl substituted with one or more substituents independently selected from the group consisting of substituted or unsubstituted $C_{1-8}$ alkyl, substituted or unsubstituted heterocyclyl (for example, substituted or unsubstituted triazolyl), halogen, aminocarbonyl, hydroxyalkyl, —OR, and —$NR_2$, wherein each R is independently H, or a substituted or unsubstituted $C_{1-4}$ alkyl.

In certain embodiments, the compounds of formula (I) have an $R^1$ group set forth herein and an $R^2$ group set forth herein.

In some embodiments of compounds of formula (I), the compound inhibits TOR kinase. In other embodiments of compounds of formula (I), the compound inhibits DNA-PK. In certain embodiments of compounds of formula (I), the compound inhibits both TOR kinase and DNA-PK.

In some embodiments of compounds of formula (I), the compound at a concentration of 10 μM inhibits TOR kinase, DNA-PK, PI3K, or a combination thereof by at least about 50%. Compounds of formula (I) may be shown to be inhibitors of the kinases above in any suitable assay system.

Representative Dihydropyrazino-Pyrazine Compounds of formula (I) include:

7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-methoxycyclohexyl)-3,4-dihydropyrazino[2,3-b]pyrazin-2(1H)-one;

7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;

1-ethyl-7-(1H-pyrrolo[3,2-b]pyridin-5-yl)-3,4-dihydropyrazino[2,3-b]pyrazin-2(1H)-one;

7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;

7-(1H-benzo[d]imidazol-4-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;

7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;

7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;

7-(6-(1H-1,2,4-triazol-3-yl)pyridin-3-yl)-1-(2-methoxyethyl)-3,4-dihydropyrazino[2,3-b]pyrazin-2(1H)-one;

7-(6-(1H-1,2,4-triazol-3-yl)pyridin-3-yl)-1-ethyl-3,4-dihydropyrazino[2,3-b]pyrazin-2(1H)-one;

7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;

7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;

7-(1H-indol-4-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(trans-4-hydroxycyclohexyl)-3,4-dihydropyrazino[2,3-b]pyrazin-2(1H)-one;

7-(6-(1H-1,2,4-triazol-3-yl)pyridin-3-yl)-1-(trans-4-methoxycyclohexyl)-3,4-dihydropyrazino[2,3-b]pyrazin-2(1H)-one;

7-(6-(1H-1,2,4-triazol-3-yl)pyridin-3-yl)-1-isopropyl-3,4-dihydropyrazino[2,3-b]pyrazin-2(1H)-one;

7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;

7-(5-fluoro-2-methyl-4-(1H-1,2,4-triazol-3-yl)phenyl)-1-isopropyl-3,4-dihydropyrazino[2,3-b]pyrazin-2(1H)-one;

1-ethyl-7-(5-fluoro-2-methyl-4-(1H-1,2,4-triazol-3-yl)phenyl)-3,4-dihydropyrazino[2,3-b]pyrazin-2(1H)-one;

7-(2-hydroxypyridin-4-yl)-1-(2-(tetrahydro-2H-pyran-4-yl)ethyl)-3,4-dihydropyrazino[2,3-b]pyrazin-2(1H)-one;

1-isopropyl-7-(4-methyl-6-(1H-1,2,4-triazol-3-yl)pyridin-3-yl)-3,4-dihydropyrazino[2,3-b]pyrazin-2(1H)-one;

5-(8-isopropyl-7-oxo-5,6,7,8-tetrahydropyrazino[2,3-b]pyrazin-2-yl)-4-methylpicolinamide;

7-(1H-indazol-4-yl)-1-(2-(tetrahydro-2H-pyran-4-yl)ethyl)-3,4-dihydropyrazino[2,3-b]pyrazin-2(1H)-one;

7-(2-aminopyrimidin-5-yl)-1-(2-(tetrahydro-2H-pyran-4-yl)ethyl)-3,4-dihydropyrazino[2,3-b]pyrazin-2(1H)-one;

7-(2-aminopyridin-4-yl)-1-(2-(tetrahydro-2H-pyran-4-yl)ethyl)-3,4-dihydropyrazino[2,3-b]pyrazin-2(1H)-one;

7-(6-(methylamino)pyridin-3-yl)-1-(2-(tetrahydro-2H-pyran-4-yl)ethyl)-3,4-dihydropyrazino[2,3-b]pyrazin-2(1H)-one;

7-(6-hydroxypyridin-3-yl)-1-(2-(tetrahydro-2H-pyran-4-yl)ethyl)-3,4-dihydropyrazino[2,3-b]pyrazin-2(1H)-one;

7-(4-(1H-pyrazol-3-yl)phenyl)-1-(2-methoxyethyl)-3,4-dihydropyrazino[2,3-b]pyrazin-2(1H)-one;

7-(pyridin-3-yl)-1-(2-(tetrahydro-2H-pyran-4-yl)ethyl)-3,4-dihydropyrazino[2,3-b]pyrazin-2(1H)-one;

7-(1H-indazol-4-yl)-1-(2-methoxyethyl)-3,4-dihydropyrazino[2,3-b]pyrazin-2(1H)-one;

7-(1H-indazol-6-yl)-1-(2-methoxyethyl)-3,4-dihydropyrazino[2,3-b]pyrazin-2(1H)-one;

7-(pyrimidin-5-yl)-1-(2-(tetrahydro-2H-pyran-4-yl)ethyl)-3,4-dihydropyrazino[2,3-b]pyrazin-2(1H)-one;

7-(6-methoxypyridin-3-yl)-1-(2-(tetrahydro-2H-pyran-4-yl)ethyl)-3,4-dihydropyrazino[2,3-b]pyrazin-2(1H)-one;

1-(2-methoxyethyl)-7-(1H-pyrrolo[2,3-b]pyridin-5-yl)-3,4-dihydropyrazino[2,3-b]pyrazin-2(1H)-one;

1-ethyl-7-(1H-pyrrolo[2,3-b]pyridin-5-yl)-3,4-dihydropyrazino[2,3-b]pyrazin-2(1H)-one;

1-ethyl-7-(1H-indazol-4-yl)-3,4-dihydropyrazino[2,3-b]pyrazin-2(1H)-one;

7-(pyridin-4-yl)-1-(2-(tetrahydro-2H-pyran-4-yl)ethyl)-3,4-dihydropyrazino[2,3-b]pyrazin-2(1H)-one;

7-(6-aminopyridin-3-yl)-1-(2-(tetrahydro-2H-pyran-4-yl)ethyl)-3,4-dihydropyrazino[2,3-b]pyrazin-2(1H)-one;

1-methyl-7-(2-methyl-6-(4H-1,2,4-triazol-3-yl)pyridin-3-yl)-3,4-dihydropyrazino[2,3-b]pyrazin-2(1H)-one;

2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;

4-methyl-5-(7-oxo-8-((tetrahydro-2H-pyran-4-yl)methyl)-5,6,7,8-tetrahydropyrazino[2,3-b]pyrazin-2-yl)picolinamide;

5-(8-((cis-4-methoxycyclohexyl)methyl)-7-oxo-5,6,7,8-tetrahydropyrazino[2,3-b]pyrazin-2-yl)-4-methylpicolinamide;

7-(1H-pyrazol-4-yl)-1-(2-(tetrahydro-2H-pyran-4-yl)ethyl)-3,4-dihydropyrazino[2,3-b]pyrazin-2(1H)-one;

1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;

3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;

1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;

3-(7-oxo-8-(2-(tetrahydro-2H-pyran-4-yl)ethyl)-5,6,7,8-tetrahydropyrazino[2,3-b]pyrazin-2-yl)benzamide;

5-(8-((trans-4-methoxycyclohexyl)methyl)-7-oxo-5,6,7,8-tetrahydropyrazino[2,3-b]pyrazin-2-yl)-4-methylpicolinamide;

3-((7-(6-(2-hydroxypropan-2-yl)pyridin-3-yl)-2-oxo-3,4-dihydropyrazino[2,3-b]pyrazin-1(2H)-yl)methyl)benzonitrile;

7-(6-(2-hydroxypropan-2-yl)pyridin-3-yl)-1-((1R,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3S)-3-methoxycyclopentyl)-3,4-dihydropyrazino[2,3-b]pyrazin-2(1H)-one;

7-(6-(2-hydroxypropan-2-yl)pyridin-3-yl)-1-((1R,3S)-3-methoxycyclopentyl)-3,4-dihydropyrazino[2,3-b]pyrazin-2(1H)-one;

7-(1H-indazol-6-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(2-morpholinoethyl)-3,4-dihydropyrazino[2,3-b]pyrazin-2(1H)-one;

1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(2-morpholinoethyl)-3,4-dihydropyrazino[2,3-b]pyrazin-2(1H)-one;

1-isopropyl-7-(2-methyl-6-(4H-1,2,4-triazol-3-yl)pyridin-3-yl)-3,4-dihydropyrazino[2,3-b]pyrazin-2(1H)-one;

7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;

1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;

1-(trans-4-hydroxycyclohexyl)-7-(6-(2-hydroxypropan-2-yl)pyridin-3-yl)-3,4-dihydropyrazino[2,3-b]pyrazin-2(1H)-one;

1-(cis-4-hydroxycyclohexyl)-7-(6-(2-hydroxypropan-2-yl)pyridin-3-yl)-3,4-dihydropyrazino[2,3-b]pyrazin-2(1H)-one;

4-(7-oxo-8-(2-(tetrahydro-2H-pyran-4-yl)ethyl)-5,6,7,8-tetrahydropyrazino[2,3-b]pyrazin-2-yl)benzamide;

7-(1H-indazol-5-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;

1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

7-(1H-indol-5-yl)-1-(2-(tetrahydro-2H-pyran-4-yl)ethyl)-3,4-dihydropyrazino[2,3-b]pyrazin-2(1H)-one;

1-ethyl-7-(2-methyl-6-(4H-1,2,4-triazol-3-yl)pyridin-3-yl)-3,4-dihydropyrazino[2,3-b]pyrazin-2(1H)-one;

7-(1H-indol-6-yl)-1-(2-(tetrahydro-2H-pyran-4-yl)ethyl)-3,4-dihydropyrazino[2,3-b]pyrazin-2(1H)-one;

7-(4-(2-hydroxypropan-2-yl)phenyl)-1-(trans-4-methoxycyclohexyl)-3,4-dihydropyrazino[2,3-b]pyrazin-2(1H)-one;

7-(6-(2-hydroxypropan-2-yl)pyridin-3-yl)-1-(tetrahydro-2H-pyran-4-yl)-3,4-dihydropyrazino[2,3-b]pyrazin-2(1H)-one;

1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((cis-4-methoxycyclohexyl)methyl)-3,4-dihydropyrazino[2,3-b]pyrazin-2(1H)-one;

1-(2-methoxyethyl)-7-(4-methyl-2-(methylamino)-1H-benzo[d]imidazol-6-yl)-3,4-dihydropyrazino[2,3-b]pyrazin-2(1H)-one;

7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;

7-(2-methyl-4-(4H-1,2,4-triazol-3-yl)phenyl)-3,4-dihydropyrazino[2,3-b]pyrazin-2(1H)-one;

1-(2-methoxyethyl)-7-(4-methyl-6-(1H-1,2,4-triazol-3-yl)pyridin-3-yl)-3,4-dihydropyrazino[2,3-b]pyrazin-2(1H)-one;

1-benzyl-7-(2-methyl-4-(4H-1,2,4-triazol-3-yl)phenyl)-3,4-dihydropyrazino[2,3-b]pyrazin-2(1H)-one;

7-(3-fluoro-4-(4H-1,2,4-triazol-3-yl)phenyl)-1-(2-methoxyethyl)-3,4-dihydropyrazino[2,3-b]pyrazin-2(1H)-one;

7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;

1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(trans-4-methoxycyclohexyl)-3,4-dihydropyrazino[2,3-b]pyrazin-2(1H)-one;

7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

1-(2-methoxyethyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((trans-4-methoxycyclohexyl)methyl)-3,4-dihydropyrazino[2,3-b]pyrazin-2(1H)-one;

1-(cyclopentylmethyl)-7-(6-(2-hydroxypropan-2-yl)pyridin-3-yl)-3,4-dihydropyrazino[2,3-b]pyrazin-2(1H)-one;

7-(4-(2-hydroxypropan-2-yl)phenyl)-1-(2-methoxyethyl)-3,4-dihydropyrazino[2,3-b]pyrazin-2(1H)-one;

(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;

7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(4-(trifluoromethyl)benzyl)-3,4-dihydropyrazino[2,3-b]pyrazin-2(1H)-one;

7-(6-(2-hydroxypropan-2-yl)pyridin-3-yl)-1-(3-(trifluoromethyl)benzyl)-3,4-dihydropyrazino[2,3-b]pyrazin-2(1H)-one;

7-(6-(2-hydroxypropan-2-yl)pyridin-3-yl)-1-(3-methoxypropyl)-3,4-dihydropyrazino[2,3-b]pyrazin-2(1H)-one;

7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-methoxyethyl)-3,4-dihydropyrazino[2,3-b]pyrazin-2(1H)-one;

7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;

7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;

7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;

7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one;

7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;

7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one;

1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one; and 1-(2-hydroxyethyl)-7-(2-methyl-6-(1H-1,2,4-triazol-3-yl)pyridin-3-yl)-3,4-dihydropyrazino[2,3-b]pyrazin-2(1H)-one, and pharmaceutically acceptable salts, clathrates, solvates, stereoisomers, tautomers, prodrugs, metabolites and isotopologues, thereof.

4.4 Methods for Making Dihydropyrazino-Pyrazine Compounds

The Dihydropyrazino-Pyrazine Compounds can be obtained via standard, well-known synthetic methodology, see e.g., March, J. Advanced Organic Chemistry; Reactions Mechanisms, and Structure, 4th ed., 1992. Starting materials useful for preparing compounds of formula (I) and intermediates therefore, are commercially available or can be prepared from commercially available materials using known synthetic methods and reagents.

Particular methods for preparing compounds of formula (I) are disclosed in U.S. Pat. No. 8,110,578, issued Feb. 7, 2012, and U.S. Pat. No. 8,569,494, issued Oct. 29, 2013, each incorporated by reference herein in their entirety.

4.5 Methods of Use

In certain embodiments, provided herein are methods for the treatment or management of CLL. In other embodiments, provided herein are methods for the treatment or management of T-PLL.

In one embodiment, the CLL is chemotherapy-resistant. In another embodiment, the CLL is etoposide-resistant. In other embodiments, the CLL is characterized as the small lymphocytic lymphoma (SLL) variant of CLL.

In one embodiment, the T-PLL is chemotherapy-resistant. In another embodiment, the T-PLL is etoposide-resistant.

In one embodiment, the CLL is IgVH-mutated CLL. In one embodiment, the CLL is IgVH-unmutated CLL. In one embodiment, the CLL is p53/ATM wild type CLL. In one embodiment, the CLL is p53 mutated CLL. In one embodiment, the CLL is p53 dysfunctional CLL.

In one embodiment, the T-PLL is IgVH-mutated T-PLL. In one embodiment, the T-PLL is IgVH-unmutated T-PLL. In one embodiment, the T-PLL is p53/ATM wild type T-PLL. In one embodiment, the T-PLL is p53 mutated T-PLL. In one embodiment, the T-PLL is p53 dysfunctional T-PLL.

In certain embodiments, the CLL is characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity. In one embodiment, the CLL is characterized by Zap-70 positivity.

In certain embodiments, the T-PLL is characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity. In one embodiment, the T-PLL is characterized by Zap-70 positivity.

In one embodiment, the CLL is characterized by deletion of all or part of chromosome 11q. In other embodiments, the CLL is characterized by deletion of chromosome 11q22. In others, the CLL is characterized by loss or mutation of the gene encoding ATM. In some such embodiments, the mutation is biallelic. In yet others, the CLL is characterized by loss of ATM expression or function. In one embodiment, the CLL is characterized by deletion of all or part of chromosome 11q, measured by fluorescence in situ hybridization (FISH) or gene sequencing. In another embodiment, the CLL is characterized by loss of the gene encoding ATM measured by FISH. In another embodiment, the CLL is characterized by mutation of the gene encoding ATM measured by gene sequencing. In another embodiment, the CLL is characterized by loss of ATM expression measured by immunohistochemistry (IHC) or Western Blot. In another embodiment, the CLL is characterized by ATM function loss due to mutation, measured by gene sequencing.

In one embodiment, the T-PLL is characterized by deletion of all or part of chromosome 11q. In other embodiments, the T-PLL is characterized by deletion of chromosome 11q22. In others, the T-PLL is characterized by loss or mutation of the gene encoding ATM. In some such embodiments, the mutation is biallelic. In yet others, the T-PLL is characterized by loss of ATM expression or function. In one embodiment, the T-PLL is characterized by deletion of all or part of chromosome 11q, measured by fluorescence in situ hybridization (FISH) or gene sequencing. In another embodiment, the T-PLL is characterized by loss of the gene encoding ATM measured by FISH. In another embodiment, the T-PLL is characterized by mutation of the gene encoding ATM measured by gene sequencing. In another embodiment, the T-PLL is characterized by loss of ATM expression measured by immunohistochemistry (IHC) or Western Blot. In another embodiment, the T-PLL is characterized by ATM function loss due to mutation, measured by gene sequencing.

In certain embodiments, a Dihydropyrazino-Pyrazine Compound is administered to a patient who has locally advanced, recurrent or metastatic, relapsed or refractory CLL or T-PLL. In another embodiment, a Dihydropyrazino-Pyrazine Compound is administered to a patient having CLL or T-PLL who has received at least one prior line of therapy.

In certain embodiments, a Dihydropyrazino-Pyrazine Compound is administered to a patient who has locally advanced, recurrent or metastatic CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity and not amenable to curative surgical resection. In some embodiments, a Dihydropyrazino-Pyrazine Compound is administered to a patient who has CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity and who has received at least one prior line of platinum based chemotherapy. In some embodiments, a Dihydropyrazino-Pyrazine Compound is administered to a patient who has a CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity and showing DNA-PK overexpression.

In certain embodiments, a Dihydropyrazino-Pyrazine Compound is administered to a patient who has locally advanced, recurrent or metastatic T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity and not amenable to curative surgical resection. In some embodiments, a Dihydropyrazino-Pyrazine Compound is administered to a patient who has T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity and who has received at least one prior line of platinum based chemotherapy. In some embodiments, a Dihydropyrazino-Pyrazine Compound is administered to a patient who has a T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity and showing DNA-PK overexpression.

In certain embodiments, provided herein are methods for achieving an International Workshop on Chronic Lymphocytic Leukemia (IWCLL) response definition of a complete response, partial response or stable disease in a patient having CLL, comprising administering an effective amount of a Dihydropyrazino-Pyrazine Compound to said patient. In certain embodiments, provided herein are methods for achieving an International Workshop on Chronic Lymphocytic Leukemia (IWCLL) response definition of a complete response, partial response or stable disease in a patient having T-PLL, comprising administering an effective amount of a Dihydropyrazino-Pyrazine Compound to said patient.

In some embodiments, provided herein are methods for achieving an International Workshop on Chronic Lymphocytic Leukemia (IWCLL) response definition of a complete response, partial response or stable disease in a patient having CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient. In some embodiments, provided herein are methods for achieving an International Workshop on Chronic Lymphocytic Leukemia (IWCLL) response definition of a complete response, partial response or stable disease in a patient having T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient.

In certain embodiments, provided herein are methods for achieving a National Cancer Institute-sponsored Working Group on Chronic Lymphocytic Leukemia (NCI-WG CLL) response definition of a complete response, partial response or stable disease in a patient having CLL, comprising administering an effective amount of a Dihydropyrazino-Pyrazine Compound to said patient. In certain embodiments, provided herein are methods for achieving a National Cancer Institute-sponsored Working Group on Chronic Lymphocytic Leukemia (NCI-WG CLL) response definition of a complete response, partial response or stable disease in a patient having T-PLL, comprising administering an effective amount of a Dihydropyrazino-Pyrazine Compound to said patient.

In some embodiments, provided herein are methods for achieving a National Cancer Institute-sponsored Working Group on Chronic Lymphocytic Leukemia (NCI-WG CLL) response definition of a complete response, partial response or stable disease in a patient having CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient.

In some embodiments, provided herein are methods for achieving a National Cancer Institute-sponsored Working Group on Chronic Lymphocytic Leukemia (NCI-WG CLL) response definition of a complete response, partial response or stable disease in a patient having T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient.

In certain embodiments, provided herein are methods for treating CLL, comprising administering an effective amount of a Dihydropyrazino-Pyrazine Compound to a patient having CLL, wherein the treatment results in one or more of inhibition of disease progression, increased Time To Progression (TTP), increased Overall Survival (OS), increased Progression-free Survival (PFS), increased Event-free Survival, increased Disease-free Survival, increased Response Duration, increased Lymphoma-specific survival, and/or increased Time To Next Treatment.

In certain embodiments, provided herein are methods for treating T-PLL, comprising administering an effective amount of a Dihydropyrazino-Pyrazine Compound to a patient having T-PLL, wherein the treatment results in one or more of inhibition of disease progression, increased Time To Progression (TTP), increased Overall Survival (OS), increased Progression-free Survival (PFS), increased Event-free Survival, increased Disease-free Survival, increased Response Duration, increased Lymphoma-specific survival, and/or increased Time To Next Treatment.

In some embodiments, provided herein are methods for treating CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to a patient having said CLL, wherein the treatment results in one or more of inhibition of disease progression, increased Time To Progression (TTP), increased Overall Survival (OS), increased Progression-free Survival (PFS), increased Event-free Survival, increased Disease-free Survival, increased Response Duration, increased Lymphoma-specific survival, and/or increased Time To Next Treatment.

In some embodiments, provided herein are methods for treating T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to a patient having said T-PLL, wherein the treatment results in one or more of inhibition of disease progression, increased Time To Progression (TTP), increased Overall Survival (OS), increased Progression-free Survival (PFS), increased Event-free Survival, increased Disease-free Survival, increased Response Duration, increased Lymphoma-specific survival, and/or increased Time To Next Treatment.

In certain embodiments, provided herein are methods for achieving an International Workshop Criteria (IWC) response definition for advanced lymphoma of a complete response, partial response or stable disease in a patient having CLL, comprising administering an effective amount of a Dihydropyrazino-Pyrazine Compound to said patient.

In certain embodiments, provided herein are methods for achieving an International Workshop Criteria (IWC) response definition for advanced lymphoma of a complete response, partial response or stable disease in a patient having T-PLL, comprising administering an effective amount of a Dihydropyrazino-Pyrazine Compound to said patient.

In some embodiments, provided herein are methods for achieve an International Workshop Criteria (IWC) response definition for advanced lymphoma of a complete response, partial response or stable disease in a patient having CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient.

In some embodiments, provided herein are methods for achieve an International Workshop Criteria (IWC) response definition for advanced lymphoma of a complete response, partial response or stable disease in a patient having T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient.

In certain embodiments, provided herein are methods for inhibiting phosphorylation of S6RP, 4E-BP1 and/or AKT in a patient having CLL, comprising administering an effective amount of a Dihydropyrazino-Pyrazine Compound to said patient.

In certain embodiments, provided herein are methods for inhibiting phosphorylation of S6RP, 4E-BP1 and/or AKT in a patient having T-PLL, comprising administering an effective amount of a Dihydropyrazino-Pyrazine Compound to said patient.

In some embodiments, provided herein are methods for inhibiting phosphorylation of S6RP, 4E-BP1 and/or AKT in a patient having CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient.

In some embodiments, provided herein are methods for inhibiting phosphorylation of S6RP, 4E-BP1 and/or AKT in a patient having T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient.

In some such embodiments, the inhibition of phosphorylation is assessed in a biological sample of the patient, such as in circulating blood cells, skin biopsies. In such embodiments, the amount of inhibition of phosphorylation is assessed by comparison of the amount of phospho-S6RP, 4E-BP1 and/or AKT before and after administration of the Dihydropyrazino-Pyrazine Compound.

In certain embodiments, provided herein are methods for measuring inhibition of phosphorylation of S6RP, 4E-BP1 or AKT in a patient having CLL, comprising administering an effective amount of a Dihydropyrazino-Pyrazine Compound to said patient, measuring the amount of phosphorylated S6RP, 4E BP1 and/or AKT in said patient, and comparing said amount of phosphorylated S6RP, 4E BP1 and/or AKT to that of said patient prior to administration of an effective amount of a Dihydropyrazino-Pyrazine Compound.

In certain embodiments, provided herein are methods for measuring inhibition of phosphorylation of S6RP, 4E-BP1 or AKT in a patient having T-PLL, comprising administering an effective amount of a Dihydropyrazino-Pyrazine Compound to said patient, measuring the amount of phosphorylated S6RP, 4E BP1 and/or AKT in said patient, and comparing said amount of phosphorylated S6RP, 4E BP1 and/or AKT to that of said patient prior to administration of an effective amount of a Dihydropyrazino-Pyrazine Compound.

In some embodiments, provided herein are methods for measuring inhibition of phosphorylation of S6RP, 4E-BP1 or AKT in a patient having CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient, measuring the amount of phosphorylated S6RP, 4E BP1 and/or AKT in said patient, and comparing said amount of phosphorylated S6RP, 4E BP1 and/or AKT to that of said patient prior to administration of an effective amount of a Dihydropyrazino-Pyrazine Compound.

In some embodiments, provided herein are methods for measuring inhibition of phosphorylation of S6RP, 4E-BP1 or AKT in a patient having T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient, measuring the amount of phosphorylated S6RP, 4E BP1 and/or AKT in said patient, and comparing said amount of phosphorylated S6RP, 4E BP1 and/or AKT to that of said patient prior to administration of an effective amount of a Dihydropyrazino-Pyrazine Compound.

In certain embodiments, provided herein are methods for inhibiting phosphorylation of S6RP, 4E-BP1 and/or AKT in a biological sample of a patient having CLL, comprising administering an effective amount of a Dihydropyrazino-Pyrazine Compound to said patient and comparing the amount of phosphorylated S6RP, 4E-BP1 and/or AKT in a biological sample of a patient obtained prior to and after administration of said Dihydropyrazino-Pyrazine Compound, wherein less phosphorylated S6RP, 4E-BP1 and/or AKT in said biological sample obtained after administration of said Dihydropyrazino-Pyrazine Compound relative to the amount of phosphorylated S6RP, 4E-BP1 and/or AKT in said biological sample obtained prior to administration of said Dihydropyrazino-Pyrazine Compound indicates inhibition.

In certain embodiments, provided herein are methods for inhibiting phosphorylation of S6RP, 4E-BP1 and/or AKT in a biological sample of a patient having T-PLL, comprising administering an effective amount of a Dihydropyrazino-Pyrazine Compound to said patient and comparing the amount of phosphorylated S6RP, 4E-BP1 and/or AKT in a biological sample of a patient obtained prior to and after administration of said Dihydropyrazino-Pyrazine Compound, wherein less phosphorylated S6RP, 4E-BP1 and/or AKT in said biological sample obtained after administration of said Dihydropyrazino-Pyrazine Compound relative to the amount of phosphorylated S6RP, 4E-BP1 and/or AKT in said biological sample obtained prior to administration of said Dihydropyrazino-Pyrazine Compound indicates inhibition.

In some embodiments, provided herein are methods for inhibiting phosphorylation of S6RP, 4E-BP1 and/or AKT in a biological sample of a patient having CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient and comparing the amount of phosphorylated S6RP, 4E-BP1 and/or AKT in a biological sample of a patient obtained prior to and after administration of said Dihydropyrazino-Pyrazine Compound, wherein less phosphorylated S6RP, 4E-BP1 and/or AKT in said biological sample obtained after administration of said Dihydropyrazino-Pyrazine Compound relative to the amount of phosphorylated S6RP, 4E-BP1 and/or AKT in said biological sample obtained prior to administration of said Dihydropyrazino-Pyrazine Compound indicates inhibition.

In some embodiments, provided herein are methods for inhibiting phosphorylation of S6RP, 4E-BP1 and/or AKT in a biological sample of a patient having T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient and comparing the amount of phosphorylated S6RP, 4E-BP1 and/or AKT in a biological sample of a patient obtained prior to and after administration of said Dihydropyrazino-Pyrazine Compound, wherein less phosphorylated S6RP, 4E-BP1 and/or AKT in said biological sample obtained after administration of said Dihydropyrazino-Pyrazine Compound relative to the amount of phosphorylated S6RP, 4E-BP1 and/or AKT in said biological sample obtained prior to administration of said Dihydropyrazino-Pyrazine Compound indicates inhibition.

In certain embodiments, provided herein are methods for inhibiting DNA-PK activity in a patient having CLL, comprising administering an effective amount of a Dihydropyrazino-Pyrazine Compound to said patient.

In certain embodiments, provided herein are methods for inhibiting DNA-PK activity in a patient having T-PLL, comprising administering an effective amount of a Dihydropyrazino-Pyrazine Compound to said patient.

In some embodiments, provided herein are methods for inhibiting DNA-PK activity in a patient having CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient.

In some embodiments, provided herein are methods for inhibiting DNA-PK activity in a patient having T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient.

In certain embodiments, DNA-PK inhibition is assessed in the skin of the patient, in one example in a UV light-irradiated skin sample of said patient. In one embodiment, inhibition is assessed by measuring the amount of phosphorylated DNA-PK S2056 (also known as pDNA-PK S2056) before and after administration of the Dihydropyrazino-Pyrazine Compound. In certain embodiments, provided herein are methods for measuring inhibition of phosphorylation of DNA-PK S2056 in a skin sample of a patient, comprising administering an effective amount of a Dihydropyrazino-Pyrazine Compound to said patient, measuring the amount of phosphorylated DNA-PK S2056 present in the skin sample and comparing said amount of phosphorylated DNA-PK S2056 to that in a skin sample from said patient prior to administration of an effective amount of a Dihydropyrazino-Pyrazine Compound. In one embodiment, the skin sample is irradiated with UV light.

In certain embodiments, provided herein are methods for inhibiting DNA-PK activity in a skin sample of a patient having CLL, comprising administering an effective amount of a Dihydropyrazino-Pyrazine Compound to said patient and comparing the amount of phosphorylated DNA-PK in a biological sample of a patient obtained prior to and after administration of said Dihydropyrazino-Pyrazine Compound, wherein less phosphorylated DNA-PK in said biological sample obtained after administration of said Dihydropyrazino-Pyrazine Compound relative to the amount of phosphorylated DNA-PK in said biological sample obtained prior to administration of said Dihydropyrazino-Pyrazine Compound indicates inhibition.

In certain embodiments, provided herein are methods for inhibiting DNA-PK activity in a skin sample of a patient having T-PLL, comprising administering an effective amount of a Dihydropyrazino-Pyrazine Compound to said patient and comparing the amount of phosphorylated DNA-PK in a biological sample of a patient obtained prior to and after administration of said Dihydropyrazino-Pyrazine Compound, wherein less phosphorylated DNA-PK in said biological sample obtained after administration of said Dihydropyrazino-Pyrazine Compound relative to the amount of phosphorylated DNA-PK in said biological sample obtained prior to administration of said Dihydropyrazino-Pyrazine Compound indicates inhibition In some embodiments, provided herein are methods for inhibiting DNA-PK activity in a skin sample of a patient having CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient and comparing the amount of phosphorylated DNA-PK in a biological sample of a patient obtained prior to and after administration of said Dihydropyrazino-Pyrazine Compound, wherein less phosphorylated DNA-PK in said biological sample obtained after administration of said Dihydropyrazino-Pyrazine Compound relative to the amount of phosphorylated DNA-PK in said biological sample obtained prior to administration of said Dihydropyrazino-Pyrazine Compound indicates inhibition.

In some embodiments, provided herein are methods for inhibiting DNA-PK activity in a skin sample of a patient having T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising administering an effective amount of a Dihydropyrazino-Pyrazine Compound to said patient and comparing the amount of phosphorylated DNA-PK in a biological sample of a patient obtained prior to and after administration of said Dihydropyrazino-Pyrazine Compound, wherein less phosphorylated DNA-PK in said biological sample obtained after administration of said Dihydropyrazino-Pyrazine Compound relative to the amount of phosphorylated DNA-PK in said biological sample obtained prior to administration of said Dihydropyrazino-Pyrazine Compound indicates inhibition.

In some embodiments, the Dihydropyrazino-Pyrazine Compound is a compound as described herein. In one embodiment, the Dihydropyrazino-Pyrazine Compound is Compound 1 (a Dihydropyrazino-Pyrazine Compound set forth herein having molecular formula $C_{16}H_{16}N_8O$). In one embodiment, the Dihydropyrazino-Pyrazine Compound is Compound 2 (a Dihydropyrazino-Pyrazine Compound set forth herein having molecular formula $C_{21}H_{27}N_5O_3$). In one embodiment, the Dihydropyrazino-Pyrazine Compound is Compound 3 (a Dihydropyrazino-Pyrazine Compound set forth herein having molecular formula $C_{20}H_{25}N_5O_3$). In one embodiment, Compound 1 is 1-ethyl-7-(2-methyl-6-(1H-1,2,4-triazol-3-yl)pyridin-3-yl)-3,4-dihydropyrazino[2,3-b]pyrazin-2(1H)-one, or a tautomer thereof, for example, 1-ethyl-7-(2-methyl-6-(4H-1,2,4-triazol-3-yl)pyridin-3-yl)-3,4-dihydropyrazino[2,3-b]pyrazin-2(1H)-one, or 1-ethyl-7-(2-methyl-6-(1H-1,2,4-triazol-5-yl)pyridin-3-yl)-3,4-dihydropyrazino[2,3-b]pyrazin-2(1H)-one. In one embodiment, Compound 2 is 7-(6-(2-hydroxypropan-2-yl)pyridin-3-yl)-1-((1r,4r)-4-methoxycyclohexyl)-3,4-dihydropyrazino-[2,3-b]pyrazin-2(1H)-one, alternatively named 7-(6-(2-hydroxypropan-2-yl)pyridin-3-yl)-1-((trans)-4-methoxycyclohexyl)-3,4-dihydropyrazino[2,3-b]pyrazin-2(1H)-one, or 7-(6-(2-hydroxypropan-2-yl)pyridin-3-yl)-1-((1R*,4R*)-4-methoxycyclohexyl)-3,4-dihydropyrazino[2,3-b]pyrazin-2(1H)-one. In another embodiment, Compound 3 is 1-((trans)-4-hydroxycyclohexyl)-7-(6-(2-hydroxypropan-2-yl)pyridin-3-yl)-3,4-dihydropyrazino[2,3-b]pyrazin-2(1H)-one, alternatively named 1-((1r,4r)-4-hydroxycyclohexyl)-7-(6-(2-hydroxypropan-2-yl)pyridin-3-yl)-3,4-dihydropyrazino[2,3-b]pyrazin-2(1H)-one. In one embodiment, Compound 3 is a metabolite of Compound 2.

Further provided herein are methods for treating patients who have been previously treated for CLL, but are non-responsive to standard therapies, as well as those who have not previously been treated. Further provided herein are methods for treating patients who have been previously treated for T-PLL, but are non-responsive to standard therapies, as well as those who have not previously been treated.

Further provided herein are methods for treating patients who have been previously treated for CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, but are non-responsive to standard therapies, as well as those who have not previously been treated. Further provided herein are methods for treating patients who have been previously treated for T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, but are non-responsive to standard therapies, as well as those who have not previously been treated.

Further provided herein are methods for treating patients who have undergone surgery in an attempt to treat the condition at issue, as well as those who have not. Because patients with CLL or T-PLL may have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with CLL or T-PLL.

In one embodiment, the CLL is that in which the PI3K/mTOR pathway is activated. In certain embodiments, the T-PLL is that in which the PI3K/mTOR pathway is activated.

In one embodiment, the CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity is that in which the PI3K/mTOR pathway is activated. In certain embodiments, the T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity is that in which the PI3K/mTOR pathway is activated.

In one embodiment, the methods provided herein further comprise the administration of an effective amount of fludarabine.

4.6 Pharmaceutical Compositions and Routes of Administration

Provided herein are compositions, comprising an effective amount of a Dihydropyrazino-Pyrazine Compound, and compositions comprising an effective amount of a Dihydropyrazino-Pyrazine Compound and a pharmaceutically acceptable carrier or vehicle. In some embodiments, the pharmaceutical compositions described herein are suitable for oral, parenteral, mucosal, transdermal or topical administration.

The Dihydropyrazino-Pyrazine Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Dihydropyrazino-Pyrazine Compound in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a Dihydropyrazino-Pyrazine Compound to be administered to a patient is rather widely variable and can be subject to the judgment of a health-care practitioner. In general, the Dihydropyrazino-Pyrazine Compounds can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight, about 0.25 mg/kg of a patient's body weight to about 0.5 mg/kg of a patient's body weight, or about 0.007 mg/kg of a patient's body weight to about 1.7 mg/kg of patient's body weight. In one embodiment, one dose is given per day. In another embodiment, two doses are given per day. In any given case, the amount of the Dihydropyrazino-Pyrazine Compound administered will depend on such factors as the solubility of the active component, the formulation used and the route of administration.

In one embodiment, provided herein are methods for the treatment or prevention of CLL or T-PLL, comprising the administration of about 0.375 mg/day to about 750 mg/day, about 0.75 mg/day to about 375 mg/day, about 3.75 mg/day to about 75 mg/day, about 7.5 mg/day to about 55 mg/day, about 18 mg/day to about 37 mg/day, about 0.5 mg/day to about 60 mg/day, or about 0.5 mg/day to about 128 mg/day of a Dihydropyrazino-Pyrazine Compound to a patient in need thereof. In another embodiment, provided herein are methods for the treatment or prevention of CLL or T-PLL, comprising the administration of about 0.5 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Dihydropyrazino-Pyrazine Compound to a patient in need thereof. In a particular embodiment, the methods disclosed herein comprise the administration of 0.5 mg/day, 1 mg/day, 2 mg/day, 2.5 mg/day, 4 mg/day, 8 mg/day, 10 mg/day, 15 mg/day, 16 mg/day, 20 mg/day, 25 mg/day, 30 mg/day, 45 mg/day, 60 mg/day, 90 mg/day, 120 mg/day or 128 mg/day of a Dihydropyrazino-Pyrazine Compound to a patient in need thereof. In a particular embodiment, the methods disclosed herein comprise the administration of 20 mg/day of a Dihydropyrazino-Pyrazine Compound to a patient in need thereof, wherein the Dihydropyrazino-Pyrazine Compound is administered in a unit dose of 10 mg twice daily (BID).

In another embodiment, provided herein are unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg of a Dihydropyrazino-Pyrazine Compound.

In a particular embodiment, provided herein are unit dosage formulation comprising about 0.1 mg, 0.25 mg, 0.5 mg, 1 mg, 2.5 mg, 5 mg, 7.5 mg, 10 mg, 15 mg, 20 mg, 30 mg, 35 mg, 45 mg, 50 mg, 60 mg, 70 mg, 75 mg, 100 mg, 125 mg, 140 mg, 150 mg, 175 mg, 200 mg, 250 mg, 280 mg, 300 mg, 350 mg, 400 mg, 500 mg, 560 mg, 600 mg, 700 mg, 750 mg, 800 mg, 1000 mg or 1400 mg of a Dihydropyrazino-Pyrazine Compound. In a particular embodiment, provided herein are unit dosage formulations that comprise 2.5 mg, 5 mg, 7.5 mg, 8 mg, 10 mg, 15 mg, 20 mg, 30 mg, 45 mg, 50 mg, 60 mg or 100 mg of Dihydropyrazino-Pyrazine Compound. In a particular embodiment, provided herein are unit dosage formulations that comprise 5 mg, 7.5 mg or 10 mg of Dihydropyrazino-Pyrazine Compound.

In another embodiment, provided herein are methods for the treatment or prevention of CLL or T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising the administration of about 0.375 mg/day to about 750 mg/day, about 0.75 mg/day to about 375 mg/day, about 3.75 mg/day to about 75 mg/day, about 7.5 mg/day to about 55 mg/day, about 18 mg/day to about 37 mg/day, about 0.5 mg/day to about 60 mg/day, or about 0.5 mg/day to about 128 mg/day of a Dihydropyrazino-Pyrazine Compound to a patient in need thereof. In another embodiment, provided herein are methods for the treatment or prevention of CLL or T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising the administration of about 0.5 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Dihydropyrazino-Pyrazine Compound to a patient in need thereof. In a particular embodiment, the methods disclosed herein comprise the administration of 0.5 mg/day, 1 mg/day, 2 mg/day, 4 mg/day, 8 mg/day, 10 mg/day, 15 mg/day, 16 mg/day, 20 mg/day, 25 mg/day, 30 mg/day, 45 mg/day, 60 mg/day, 90 mg/day, 120 mg/day or 128 mg/day of a Dihydropyrazino-Pyrazine Compound to a patient in need thereof.

In one embodiment, provided herein are methods for the treatment or prevention of CLL or T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity, comprising the administration of about 2.5 mg to about 50 mg/day (such as about 2.5 mg, about 10 mg, about 15 mg, about 20 mg, about 30 mg or about 45 mg per day) of a Dihydropyrazino-Pyrazine Compound to a patient in need thereof.

A Dihydropyrazino-Pyrazine Compound can be administered once, twice, three, four or more times daily.

In certain embodiments, a Dihydropyrazino-Pyrazine Compound is administered to a patient in cycles. Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a Dihydropyrazino-Pyrazine Compound is administered daily in single or divided doses for about 3 days, about 5 days, about one week, about two weeks, about three weeks, about four weeks (e.g., 28 days), about five weeks, about six weeks, about seven weeks, about eight weeks, about ten weeks, about fifteen weeks, or about twenty weeks, followed by a rest period of about 1 day to about ten weeks. In one embodiment, the methods provided herein contemplate cycling treatments of about one week, about two weeks, about three weeks, about four weeks, about five weeks, about six weeks, about eight weeks, about ten weeks, about fifteen weeks, or about twenty weeks. In some embodiments, a Dihydropyrazino-Pyrazine Compound is administered in single or divided doses for about 3 days, about 5 days, about one week, about two weeks, about three weeks, about four weeks (e.g., 28 days), about five weeks, or about six weeks with a rest period of about 1, 2, 3, 4, 5, 6, 7, 8, 9, 10, 12, 14, 16, 18, 20, 22, 24, 26, 28, 29, or 30 days. In some embodiments, the rest period is 1 day. In some embodiments, the rest period is 3 days. In some embodiments, the rest period is 7 days. In some embodiments, the rest period is 14 days. In some embodiments, the rest period is 28 days. The frequency, number and length of dosing cycles can be increased or decreased.

A Dihydropyrazino-Pyrazine Compound can be administered orally for reasons of convenience. In one embodiment, when administered orally, a Dihydropyrazino-Pyrazine Compound is administered with a meal and water. In another embodiment, the Dihydropyrazino-Pyrazine Compound is dispersed in water or juice (e.g., apple juice or orange juice) and administered orally as a suspension. In another embodiment, when administered orally, a Dihydropyrazino-Pyrazine Compound is administered in a fasted state.

The Dihydropyrazino-Pyrazine Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Dihydropyrazino-Pyrazine Compound without an additional carrier, excipient or vehicle.

In another embodiment, provided herein are compositions, comprising an effective amount of a Dihydropyrazino-Pyrazine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Dihydropyrazino-Pyrazine Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Dihydropyrazino-Pyrazine Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Dihydropyrazino-Pyrazine Compound can be delayed or prolonged by proper formulation. For example, a slowly soluble pellet of the Dihydropyrazino-Pyrazine Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Dihydropyrazino-Pyrazine Compound in oily or emulsified vehicles that allow it to disperse slowly in the serum.

In certain embodiments, the Dihydropyrazino-Pyrazine Compound is administered in a formulation set forth in U.S. Patent Application Publication No. 2013-0142873, published Jun. 6, 2013, which is incorporated herein in its entirety (see particularly paragraph [0323] to paragraph [0424], and paragraph [0636] to paragraph [0655]). In other embodiments, the Dihydropyrazino-Pyrazine Compound is administered in a formulation set forth in U.S. Provisional Patent Application No. 61/828,506, filed May 29, 2013, which is incorporated herein in its entirety (see particularly paragraph [0246] to paragraph [0403], and paragraph [0571] to paragraph [0586]).

In certain embodiments, the Dihydropyrazino-Pyrazine Compound is administered in a formulation set forth in U.S. Provisional Application No. 61/813,064, filed Apr. 17, 2013, which is incorporated herein in its entirety (see particularly paragraph [0168] to paragraph [0189] and paragraph [0262] to paragraph [0294]). In other embodiments, the Dihydropyrazino-Pyrazine Compound is administered in a formulation set forth in U.S. Provisional Patent Application No. 61/911,201, filed Dec. 3, 2013, which is incorporated herein in its entirety (see particularly paragraph [0170] to paragraph [0190], and paragraph to paragraph [0296])

4.7 Kits

In certain embodiments, provided herein are kits comprising a Dihydropyrazino-Pyrazine Compound.

In other embodiments, provide herein are kits comprising a Dihydropyrazino-Pyrazine Compound and means for monitoring patient response to administration of said Dihydropyrazino-Pyrazine Compound. In certain embodiments, the patient has CLL or T-PLL. In certain embodiments, the patient has CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity. In certain embodiments, the patient has T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity. In particular embodiments, the patient response measured is inhibition of disease progression, inhibition of tumor growth, reduction of primary and/or secondary tumor(s), relief of tumor-related symptoms, improvement in quality of life, delayed appearance of primary and/or secondary tumors, slowed development of primary and/or secondary tumors, decreased occurrence of primary and/or secondary tumors, slowed or decreased severity of secondary effects of disease, arrested tumor growth or regression of tumor.

In other embodiments, provided herein are kits comprising a Dihydropyrazino-Pyrazine Compound and means for measuring the amount of inhibition of phosphorylation of S6RP, 4E-BP1 and/or AKT in a patient. In certain embodiments, the kits comprise means for measuring inhibition of phosphorylation of S6RP, 4E-BP1 and/or AKT in circulating blood or tumor cells and/or skin biopsies or tumor biopsies/aspirates of a patient. In certain embodiments, provided herein are kits comprising a Dihydropyrazino-Pyrazine Compound and means for measuring the amount of inhibition of phosphorylation as assessed by comparison of the amount of phospho-S6RP, 4E-BP1 and/or AKT before, during and/or after administration of the Dihydropyrazino-Pyrazine Compound. In certain embodiments, the patient has CLL or T-PLL. In some embodiments, the CLL is SLL. In certain embodiments, the patient has CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity. In certain embodiments, the patient has T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity In other embodiments, provided herein are kits comprising a Dihydropyrazino-Pyrazine Compound and means for measuring the amount of inhibition of DNA-PK activity in a patient. In certain embodiments, the kits comprise means for measuring the amount of inhibition of DNA-PK activity in a skin sample and/or a tumor biopsy/aspirate of a patient. In one embodiment, the kits comprise a means for measuring the amount of pDNA-PK S2056 in a skin sample and/or a tumor biopsy/aspirate of a patient. In one embodiment, the skin sample is irradiated by UV light. In certain embodiments, provided herein are kits comprising a Dihydropyrazino-Pyrazine Compound and means for measuring the amount of inhibition of DNA-PK activity before, during and/or after administration of the Dihydropyrazino-Pyrazine Compound. In certain embodiments, provided herein are kits comprising a Dihydropyrazino-Pyrazine Compound and means for measuring the amount of phosphorylated DNA- PK S2056 before, during and/or after administration of the Dihydropyrazino-Pyrazine Compound. In certain embodiments, the patient has CLL or T-PLL. In certain embodiments, the patient has CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity. In certain embodiments, the patient has T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity In one embodiment, the kits provided herein comprise an amount of a Dihydropyrazino-Pyrazine Compound effective for treating or preventing CLL or T-PLL. In certain embodiments, the kits provided herein comprise an amount of a Dihydropyrazino-Pyrazine Compound effective for treating or preventing CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity. In certain embodiments, the kits provided herein comprise an amount of a Dihydropyrazino-Pyrazine Compound effective for treating or preventing T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity. In certain embodiments, the kits provided herein comprise an effective amount of Compound 1, Compound 2 or Compound 3.

In certain embodiments, the kits provided herein further comprise instructions for use, such as for administering a Dihydropyrazino-Pyrazine Compound and/or monitoring patient response to administration of a Dihydropyrazino-Pyrazine Compound.

5. EXAMPLES

5.1 Compound Formulations

Illustrative formulations of Compound 1 useful in the methods provided herein are set forth in Table 1, below.

TABLE 1

| | Exemplary Tablet Formulations | | | |
|---|---|---|---|---|
| | % w/w (mg) Batch # | | | |
| Ingredients | 1 | 2 | 3 | 4 |
| Compound 1 (active ingredient) | 10 | 10 | 10 | 10 |
| Mannitol (Mannogem EZ) | qs | qs | qs | qs |
| Microcrystalline Cellulose (PH 112) | 25 | 25 | 25 | 25 |
| Sodium Starch Glycolate | 3 | 3 | 3 | 3 |
| Silicon dioxide | 1 | 1 | 1 | 1 |
| Stearic acid | 0.5 | 0.5 | 0.5 | 0.5 |
| Disodium EDTA | | | 0.5 | 0.5 |
| BHT | | 0.4 | | 0.4 |
| Magnesium Stearate | 0.65 | 0.65 | 0.65 | 0.65 |
| Total | 100 | 100 | 100 | 100 |
| Color | Yellow | Yellow | Yellow | Yellow |

Illustrative formulations of Compound 2 useful in the methods provided herein are set forth in Tables 2-5, below.

TABLE 2

| | Amounts | |
|---|---|---|
| Ingredients | mg | % w/w |
| Compound 2 | 20.0 | 15.38 |
| Lactose monohydrate, NF (Fast Flo 316) | 63.98 | 49.22 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry yellow 03K12429 | 5.2 | 4.0 |

TABLE 3

| | Amounts | |
|---|---|---|
| Ingredients | mg | % w/w |
| Compound 2 | 5.0 | 3.80 |
| Lactose monohydrate, NF (Fast Flo 316) | 78.98 | 60.70 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry II pink 85F94211 | 5.2 | 4% weight gain |

TABLE 4

| | Amounts | | | |
|---|---|---|---|---|
| Ingredients | mg | | | % w/w |
| Compound 2 | 15.0 | 20.0 | 30.0 | 15.38 |
| Lactose monohydrate, NF (Fast Flo 316) | 48.37 | 64.50 | 96.75 | 49.62 |
| Microcrystalline cellulose, NF (Avicel pH 112) | 30.23 | 40.30 | 60.45 | 31.00 |
| Croscarmellose sodium, NF (Ac-Di-Sol) | 2.925 | 3.90 | 5.85 | 3.00 |
| Magnesium Stearate, NF | 0.975 | 1.30 | 1.95 | 1.00 |
| Total | 97.50 | 130.0 | 195.00 | 100 |
| Opadry yellow 03K12429 | 3.9 | | | 4.0 |
| Opadry II Pink 85F94211 | | 5.2 | | 4.0 |
| Opadry Pink 03K140004 | | | 7.8 | 4.0 |

TABLE 5

| | Amounts | |
|---|---|---|
| Ingredients | mg | % w/w |
| Compound 2 | 45.00 | 15.38 |
| Lactose monohydrate, NF (Fast Flo 316) | 143.955 | 49.22 |
| Microcrystalline cellulose, NF (Avicel pH 102) | 90.675 | 31.00 |
| Croscarmellose sodium, NF (Ac-Di-Sol) | 8.775 | 3.00 |
| Stearic acid, NF | 1.170 | 0.40 |
| Magnesium Stearate, NF | 2.925 | 1.00 |
| Total | 292.50 | 100 |
| Opadry pink 03K140004 | 11.70 | 4.0 |

5.2 Biological Examples

5.2.1 Biochemical Assays mTOR HTR-FRET Assay.

The following is an example of an assay that can be used to determine the TOR kinase inhibitory activity of a test compound. TOR kinase inhibitors were dissolved in DMSO and prepared as 10 mM stocks and diluted appropriately for the experiments. Reagents were prepared as follows:

"Simple TOR buffer" (used to dilute high glycerol TOR fraction): 10 mM Tris pH 7.4, 100 mM NaCl, 0.1% Tween-20, 1 mM DTT. Invitrogen mTOR (cat#PV4753) was diluted in this buffer to an assay concentration of 0.200 μg/mL.

ATP/Substrate solution: 0.075 mM ATP, 12.5 mM $MnCl_2$, 50 mM Hepes, pH 7.4, 50 mM 13-GOP, 250 nM Microcystin LR, 0.25 mM EDTA, 5 mM DTT, and 3.5 μg/mL GST-p70S6.

Detection reagent solution: 50 mM HEPES, pH 7.4, 0.01% Triton X-100, 0.01% BSA, 0.1 mM EDTA, 12.7 μg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 μL of the Simple TOR buffer is added 0.5 μL of test compound in DMSO. To initiate the reaction 5 μL of ATP/Substrate solution was added to 20 μL of the Simple TOR buffer solution (control) and to the compound solution prepared above. The assay was stopped after 60 min by adding 5 μL of a 60 mM EDTA solution; 10 μL of detection reagent solution was then added and the mixture was allowed to sit for at least 2 hours before reading on a Perkin-Elmer Envision Microplate Reader set to detect LANCE Eu TR-FRET (excitation at 320 nm and emission at 495/520 nm).

Dihydropyrazino-Pyrazine Compounds were tested in the mTOR HTR-FRET assay and were found to have activity therein, with certain compounds having an $IC_{50}$ below 10 μM in the assay, with some compounds having an $IC_{50}$ between and 0.005 nM and 250 nM, others having an $IC_{50}$ between and 250 nM and 500 nM, others having an $IC_{50}$ between 500 nM and 1 μM, and others having an $IC_{50}$ between 1 μM and 10 μM.

DNA-PK Assay.

DNA-PK assay is performed using the procedures supplied in the Promega DNA-PK assay kit (catalog # V7870). DNA-PK enzyme can be purchased from Promega (Promega cat#V5811).

Selected Dihydropyrazino-Pyrazine Compounds as described herein have, or are expected to have, an $IC_{50}$ below 10 μM in this assay, with some Dihydropyrazino-Pyrazine Compounds as described herein having an $IC_{50}$ below 1 μM, and others having an $IC_{50}$ below 0.10 μM.

5.2.2 Cell Based Assays

Growth inhibition assay for CLL patient cells. A compound can be tested as follows: A test compound (a DHPP set forth herein) is dissolved in dimethyl sulfoxide (DMSO) to prepare a 10 mM stock solution. A serial titration is performed to produce a working concentration range of 1.5 μM to 10 mM. Aliquots to produce final concentrations of 1.5 nM to 10 μM are spotted via an acoustic dispenser (EDC ATS-100) into an empty 384-well plate. The test compound is spotted in a 10-point serial dilution fashion (3-fold dilution) in duplicate within the plate. The DMSO concentration is kept constant for a final assay concentration of 0.1% DMSO. Plates are replicated for use with different cell lines and testing periods. After compound plate replication, all plates are sealed (Agilent ThermoLoc) and stored at −20° C. for up to 1 month. When ready for testing, plates are removed from the freezer, thawed, and unsealed just prior to the addition of the test cells. Cells are then diluted to the appropriate densities and added directly to the test-compound-spotted 384-well plates. Cells are allowed to grow for 72 hours at 37° C./5% $CO_2$. At the time when test compounds are added ($t_0$), initial cell numbers are assessed via a viability assay (Cell Titer-Glo) by quantifying the level of luminescence generated by ATP present in viable cells. After 72 hours, cell viability of test-compound-treated cells is assessed via Cell Titer-Glo and luminescence measurement. Cells are assayed for increased cell death by the test compound in at least 3 independent tests. A control cell line is included in each of the assays. The test compound response against this control cell line is monitored closely to enable comparison of the data generated through the assay period. All data are normalized and presented as a percentage of the DMSO-treated cells. Results are then expressed as a $IC_{50}$ value. The $0IC_{50}$ value corrects for the cell count at time zero.

Apoptosis Assay for CLL Cells.

Cells are diluted to their desired densities and added directly to test-compound-spotted 384-well plates. Cells are incubated for 24 hours in 5% $CO_2$ at 37° C. The apoptotic response is assessed by quantifying the activities of caspase 3 and caspase 7 (Caspase 3/7-Glo) in treated cells and control cells at the 24-hour time point. All data is normalized and represented as a value relative to the DMSO-treated cells. Results are then expressed as CalX, which is the minimum test compound concentration required to double the levels of caspase 3/7 relative to those of the DMSO-treated cells during their treatment period.

CLL-Coculture Assay.

Materials and Methods.

Cells and culture media: There are two types of cell in the co-culture system: the feeder cells which are L929 mouse fibroblasts stably transfected with CD40 Ligand (CD40L) (supplied by Laura Corral-Celgene-San Diego); and primary PBMC from CLL patients (CLL-PBMC) obtained from commercial sources (AllCells; Conversant Bio). The feeder cells are routinely maintained in DMEM containing 20% fetal bovine serum at 37° C. with 5% $CO_2$. Before co-culture, feeder cells are treated with mitomycin to prevent their proliferation and plated overnight in 24-well plates. The primary CLL-PBMC cells are stored frozen in liquid nitrogen vapor-phase until needed; thawed and labeled with CFSE dye (Invitrogen) to a homogeneous fluorescence immediately prior to co-culture with feeder cells. Co-culture medium consists of RPMI 1640 supplemented with 10% fetal bovine serum and the cytokines IL-4 (5 ng/ml) and IL-10 (15 ng/ml).

Measurement of Anti-Proliferative Effects of Compounds on Primary CLL-PBMC.

The CLL-PBMC co-culture assay is performed to determine the effect of the compounds in the proliferation of CLL-PBMC. The assay consists of culturing CFSE-labeled CLL-PBMC on the surface of the mitomycin-treated feeder cells previously plated. Compounds (in DMSO stock solutions) are added to the culture in duplicate at different concentrations to a final DMSO concentration of 0.01%. Plates are incubated at 37° C. with 5% $CO_2$ for up to 12 days. At intervals of 3 to 6 days, CLL-PBMC are gently collected by repeated pipetting and transferred to 96 well plates. Cells are acquired by a flow cytometer and the data is imported into FlowJo software (Tree Star Inc.). The CFSE fluorescence intensity is analyzed as it corresponds to the number of cell divisions the cells have undergone in culture during the incubation period. In this way, the percentage of cells that have divided can be calculated. The numbers of cells affected by compound treatment is normalized to DMSO control and the data is imported into Excel or GraphPrism. $IC_{50}$ is the compound dose at which a 50% inhibition of proliferation is achieved normalized to DMSO control.

Compound Toxicity Assay for CLL Patient Cells.

Primary CLL patient cells, stratified as being wildtype or del(11q) by clinical-grade FISH analysis, were seeded onto a feeder layer of CD40 ligand-expressing NIH 3T3 cells prior to treatment with Compound 1, etoposide or a combination of both compounds. Wildtype CLL cells were highly sensitive to etoposide, but resistant to Compound 1. Addition of Compound 1 to the etoposide regimen did not significantly enhance the response of the ATM-proficient CLL cells (FIG. 1A). In contrast, del(11q) CLL cells were exclusively sensitive to Compound 1, but largely resistant to etoposide (FIG. 1B). These data suggest that DNA-PK inhibition might be a useful strategy to treat chemotherapy-resistant, ATM-defective CLL.

CLL Patient Cells Apoptosis Assay.

Patient material (pheripheral blood) was obtained from CLL patients (diagnosed according to the NCI-WG guidelines) after routine follow-up or diagnostic procedures at the department of hematology of the Academic Medical Center Amsterdam. Peripheral blood mononuclear cells (PBMCs) were isolated by Ficoll density gradient centrifugation and stored in liquid nitrogen, as cell suspension in heat-inactivated fetal calf serum containing 10% DMSO. During all in vitro experiments, cells were maintained in culture medium: Iscove's modified Dulbecco medium supplemented with 10% heat-inactivated FCS, 100 U/mL penicillin, 100 m/mL gentamycin and 0.00036% β-mercaptoethanol. All samples contained at least 90% CD5+/CD19+ cells as assessed via flow cytometry. B-CLL cells were thawed and diluted to a concentration of $1.10^6$ cells/mL in IMDM plus supplements as described above. 100 μL of CLL cells were placed in a 96-well plate and treated with increasing levels of Compound 1 for 48 hours. Apoptosis was analyzed by evaluation of mitochondrial membrane potential with DioC6 (Molecular probes). Cells were incubated with 10 nM DioC6 for 30 minutes at 37° C. and 20 μg/mL propidium iodide was added to measure cell death. Expression of DioC6 was determined using the FACSCalibur flow cytometer and CellQuest software was used for data acquisition. Data were analyzed with FlowJo software (TreeStar, San Carlos, Calif., USA). Specific apoptosis is defined as % cell death in Compound 1 treated cells–% cell death in medium control using the Graphpad Prism software (Graphpad Prism 5.0, La Jolla, USA). The results are set forth in FIGS. 2A-2H.

Induction of Apoptosis by Compound 1 in CLL Cells.

Reverse transcriptase multiplex ligation-dependent probe amplification assay (RT-MLPA) was performed to determine the impact of Compound 1 on the mRNA expression levels of pro- and anti-apoptotic regulators.

Cell Culture and Detection of Apoptosis.

PBMC from CLL patients were thawed and incubated with different concentrations of Compound 1 for 48 hours. Where indicated, CLL cells were co-cultured in the presence/absence of 20 μM of the pancaspase inhibitor QvD or 5 mM N-acetyl-L-cysteine (NAC). CLL cell viability was measured by analysis of mitochondrial transmembrane potential by 3,3-dihexyloxocarbocyanine iodine (DiOC6; Invitrogen/Molecular Probes) and cell membrane permeability to propidium iodide (PI; Sigma Aldrich) using the FACS Calibur flow cytometer. Specific apoptosis is defined as [% cell death in drug treated cells]–[% cell death in medium control]/[% viable cells medium control]×100 using the Graphpad Prism software (Graphpad Prism 5.0, La Jolla, USA).

Reverse Transcription-Multiplex Ligation-Dependent Probe Amplification Assay.

CLL Cells were harvested per stimulation, washed with PBS, resuspended in RNA lysis buffer (Qiagen, Venlo, the Netherlands) and stored at –80° C. RNA was isolated using the GenElute Mammalian Total RNA Miniprep kit (Sigma-aldrich). The concentration and purity of the RNA were determined with a NanoDrop spectrophotometer ND-1000 (NanoDrop Technologies, Willington, USA). Reverse transcription-multiplex ligation-dependent probe amplification assay (RT-MLPA) procedure was performed as described previously by Eldering et al. *Nucleic Acids Res.* 2003; 31:e153. In brief, 40-60 ng of total RNA of samples were first reverse transcribed using a gene-specific probe mix (R016-X2). The resulting cDNA was annealed overnight at 60° C. to the MLPA probes. The annealed oligonucleotides were covalently linked by Ligase-65 (MRC, Amsterdam, the Netherlands) at 54° C. Ligation products were amplified by polymerase chain reaction (PCR; 33 cycles, 30 sec at 95° C., 30 sec at 60° C. and 1 min at 72° C.) using one unlabeled and on 6-carboxy-fluoroscin-labelled primer (10 pM). PCR products were mixed with 1 pM ROX 500 size standard and separated on an ABI 3100 capillary sequencer (Applied Biosystems, Warrington, United Kingdom) in Genescan mode. Results were analyzed using the programs Genescan analysis and Genotypes (Applied Biosystems). Data was further analyzed with Microsoft Excel Spreadsheet software. Normalization was performed by setting the sum of all data per sample at 100% and individual peaks were calculated relative to the 100% value.

Results.

Wildtype CLL cells were highly sensitive to etoposide, but resistant to Compound 1. Addition of Compound 1 to the etoposide regimen did not significantly enhance the response of the ATM-proficient CLL cells (FIG. 1A). In contrast, del(11q) CLL cells were exclusively sensitive to Compound 1, but largely resistant to etoposide (FIG. 1B). These data suggest that DNA-PK inhibition might be a useful strategy to treat chemotherapy-resistant, ATM-defective CLL.

Compound 1 induced apoptosis in cells from patients belonging to 4 distinct prognostic groups. Compound 1 induced apoptosis in IGVH mutated CLL cells (FIGS. 2A, E), IGVH unmutated CLL cells (FIGS. 2B, F), ATM mutated CLL cells (FIGS. 2D, G) and P53 mutated CLL cells (FIGS. 2C, H).

Compound 1-induced apoptosis was p53 independent (FIGS. 3A and 3B). Levels of the pro- and apoptotic regulators on RNA level, including above mentioned p53-target genes were not altered upon treatment with Compound 1. In order to study whether induction of cell death by Compound 1 was caspase dependent, cells were preincubated with the pan-caspase inhibitor QvD. As shown in FIGS. 3A and 3B, QvD could completely block cytotoxicity of the kinase inhibitors. A variety of chemotherapeutic drugs induce apoptosis in CLL cells by the generation of reactive oxygen species (ROS). To learn whether the observed cytotoxicity dependent on ROS formation, CLL cells were co-treated with NAC which did not result in inhibition of kinase-induced cell death (FIGS. 3A and 3B).

Adhesion of CLL Cells to Fibronection is Inhibited by Compound 1.

BCR-mediated adhesion of primary CLL cells (FIG. 4) was tested. Only IgVH unmutated samples were used as most mutated samples are anergic for in vitro BCR-activation. CLL cells pretreated with 1 μM Compound 1 were stimulated with αIgM or PMA and allowed to adhere to fibronectin-coated surfaces (n=5). Compound 1 strongly inhibited the anti-IgM-stimulated integrin-mediated adhesion to fibronectin.

Compound 1 Blocks CD40-Mediated Activation of CLL Cells.

Western blot analysis was performed using standard techniques [Hallaert et al. Blood 2008(112):5141-5149]. Samples (50 μg protein) were separated by 13% SDS-PAGE gel electrophoresis. Membranes were probed with anti-p-S6, p-4EBP1, p-Akt (Thr308), p-Akt (Ser473) (Cell Signaling), Bim (Stressgen Bioreagents Canada) and antiserum to β-actin (Santa Cruz Biotechnology) as loading control. Blots were subsequently incubated with IRDye 680 or 800 labelled secondary antibodies for 1 hour. Odyssey Imager (Li-Cor Biosciences) was used as a detection method according to the manufacturer's protocol. For the p-DNA-PK western blot, cells were lysed in RIPA sample buffer and sonificated. Samples (50 μg protein) were separated by mini protean TGX gels (Biorad). Transfer onto Immobilon-FL transfer membrane (Millipore) in 1× transfer buffer, 20% MeOH at 30 volts at 4° C. overnight. The following antibodies were used: p-DNA-PK (Ser2056) (Abcam), KAP (TIF1β), phosphorylated-KAP (phospho-TIF1β-ser824; Cell Signalling) and β-actin (Santa Cruz).

Expression of Cell Surface Markers.

Cells were washed and resuspended in staining media (phosphate-buffered saline (PBS) containing 0.5% (wt/vol) bovine serum albumin (BSA)). For analysis of expression of cell surface markers, different combinations of antibodies were used. CD54-PE and CD95-FITC purchased from Pharmingen. CD44-Alexa Fluor 700 was obtained from eBiosciences and CD58 from Immunotech. After incubation for 30 minutes at 4° C. protected from light, cells were washed twice in PBS/0.5% BSA and expression of cell surface markers was analyzed using FACSCalibur flow cytometry. Specific upregulation is defined as [MFI 3T40 control–MFI drug treated cells]/[MFI 3T40 control–MFI 3T3 control]×100 using the Graphpad Prism software.

Results.

In unstimulated CLL cells, phosphorylation of S6, the downstream effector of mTORC1 (raptor), could be completely blocked by Compound 1 (FIGS. 5A and 5B). In the lymph node microenvironment CLL cells receive pro-survival signals of surrounding cells and we previously showed that prolonged in vitro stimulation with CD40L resembles the lymph node microenvironment with respect to induction of NF-κB mediated pro-survival signaling (Tromp J M, et al. Ongone 2010; 29(36): 5071-82). The downstream effectors of mTORC1, p-S6 and p-4EBP1, and the downstream effector of mTORC2, p-Akt (Ser473) are upregulated in activated CLL cells and could be completely blocked by Compound 1 (FIGS. 6A, 6B and 6C). To further investigate the impact of Compound 1 on CD40-mediated activation of CLL cells, levels of blast cell formation was assessed. CLL cells co-cultured with CD40L showed increased blast-like appearance which was completely blocked by Compound 1 (FIGS. 6A, 6B and 6C). Furthermore, CD40 triggering increases the expression of a variety of immune accessory molecules such as death receptors (CD95) and adhesion receptors (CD54, CD58, CD44). Compound 1 showed significant inhibition of 3T40L-induced upregulation of immune accessory molecules (FIGS. 6A, 6B and 6C).

Compound 1 Reverts CD40-Induced Chemoresistance.

CD40 stimulation inhibits spontaneous cell death as previously reported [Burger et al. Blood 2009(114):2560-2561]. Lymphocytes of CLL patients were stimulated by coculture with NIH3T3 fibroblasts stably transfected with human CD40L or negative control plasmid (3T3) as described before [Pascutti et al Blood 2013 2013; 122(17):3010-9]. CLL cells were cocultured in the presence/absence of Compound 1 at the indicated concentrations. After 72 hours of culture, CLL cells were detached and either used for flow-cytometric analyses or subsequently incubated with or without Fludarabine (Sigma) for an additional 48 hours. CLL cell viability was measured as by DiOC6/PI staining as described above. Compound 1 inhibited the CD40L-induced survival (FIGS. 7A, 7B, 7C and 7D). CD40L stimulation induces resistance to cytotoxic agents, including fludarabine [Kater et al. Brit J Haematology 2004; 127:404-415]. Compound 1 partly reversed fludarabine sensitivity. Co-treatment with Compound 1 completely abolished CD40-induced fludarabine resistance (FIGS. 7A, 7B, 7C and 7D).

Results.

CLL cells originating from lymph nodes show an altered expression of apoptotic genes including increased expression of Bcl-XL, Bfl-1 and Bid and decreased expression of Bim. Together, these alterations result in resistance to various drugs. To analyze if Compound 1 changed the CD40-mediated alterations in expression levels of anti- and pro apoptotic genes, expression levels of pro and anti-apoptotic molecules by RT-MLPA in CD40L triggered CLL cells was studied. Compound 1 blocked CD40-mediated inhibition of BIM and decreased the upregulation of BID (FIGS. 7A, 7B, 7C and 7D). We next measured whether induced changes in RNA expression levels of BIM also resulted in altered BIM protein levels. CD40-mediated decreased expression of Bim was blocked by coculture with Compound 1 (FIGS. 7A, 7B, 7C and 7D).

Compound 1 Completely Blocks Proliferation of CLL Cells.

Activated T cells and follicular helper T cells present in the LN express membrane-bound CD40L and can secrete cytokines such as IL-21 that induces BCR-independent proliferation.

PBMC ($1.0 \times 10^7$/mL) were labelled with 0.5 μM carboxy-fluorescein diacetate succinimidyl ester (CFSE, Molecular Probes) as described before [Pascutti et al Blood 2013 2013; 122(17):3010-9]. Cells were cultured on 3T40L cells, in absence or presence of recombinant human IL-21 (25 ng/ml, Gibco, Invitrogen), with or without 1 μM of Compound 1. After 4 days, proliferation was assessed in a FACS Canto (BD Biosciences) and analyzed with FlowJosoftware (TreeStar, Ashland, Oreg.).

Results.

As can be seen in FIGS. 8A and 8B, proliferation is indeed strongly induced by the combination of CD40 activation and IL-21 stimulation. Proliferation of CLL cells is fully blocked by Compound 1.

5.2.3 Clinical Study A

Phase 1B, Multi-Center, Open-Label, Dose Finding Study to Assess the Safety, Tolerability, Pharmacokinetics and Preliminary Efficacy of Compound 1 Administered Orally to Subjects with CLL Characterized by Deletion of all or Part of Chromosome 11q or Loss or Mutation of the Gene Encoding ATM, or Loss of ATM Expression or Function.

Study Objectives.

The primary objectives of the study are to determine: (1) the safety and tolerability of Compound 1; (2) the non-tolerated dose (NTD) of Compound 1; (3) the maximum tolerated dose (MTD) of Compound 1; and (4) the pharmacokinetics (PK) of Compound 1, when Compound 1 is administered orally to patients having CLL characterized by deletion of all or part of chromosome 11q or loss or mutation of the gene encoding ATM, or loss of ATM expression or function.

The secondary objectives of the study are to: (1) evaluate the extent of inhibition of phosphorylation of S6RP and/or 4E-BP1 for mTORC1 activity and AKT and/or other relevant biomarkers for mTORC2 activity in blood, skin and/or tumor biopsies/aspirates, when available before and during treatment with Compound 1; (2) evaluate the inhibition of DNA-dependent protein kinase (DNA-PK) activity in skin samples irradiated by UV light, circulating CLL cells, and/or tumor biopsies/aspirates using pDNA-PK 52056 and/or other relevant biomarkers for DNA damage pathways before and during Compound 1 treatment; and (3) evaluate the efficacy of Compound 1.

Study Design.

In this study, Compound 1 is administered orally to patients having CLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity.

Adult subjects will start Compound 1 at 10 mg BID. Subjects will be evaluated for safety and antitumor activity periodically.

Study Population.

Men and women, 18 years or older, with CLL, and including subjects who have progressed on (or not been able to tolerate) standard anticancer therapy, or for whom no other approved therapy exists.

Inclusion Criteria.

Inclusion criteria are: (1) understand and voluntarily sign an informed consent document before any study-related assessments/procedures are conducted; (2) men and women, 18 years or older, with histological or cytological confirmation of CLL, including those who have progressed on (or not been able to tolerate) standard anticancer therapy or for whom no other conventional therapy exists; (3) consent to screening tumor biopsy; (4) ECOG PS of 0 or 1; (5) the following laboratory values: (i) absolute neutrophil count (ANC)≥1.0×109/L; (ii) hemoglobin (Hgb)≥9 g/dl; (iii) platelets (plt)≥30×109/L; (ii) hemoglobin (Hgb)≥9 g/dL; (iii) platelets (plt)≥100×109/L; (iv) potassium within normal range, or correctable with supplements; (v) AST/SGOT and ALT/SGPT≤2.5× Upper Limit of Normal (ULN) or ≤5.0× ULN if liver tumor is present; (vi) serum total bilirubin ≤1.5×ULN; (vii) serum creatinine ≤1.5×ULN, or 24-hr clearance ≥50 mL/min; and (viii) negative serum or urine pregnancy test within 72 hrs before starting study treatment in females of childbearing potential; (6) able to adhere to the study visit schedule and other protocol requirements; (7) subject consent to retrieve blood samples; (8) histologically-confirmed CLL (relapsed or refractory CLL, including the small lymphocytic lymphoma (SLL) variant, following failure of at least one prior line of systemic therapy); (9) laboratory confirmation of deletion of chromosome 11q22 (ATM) in CLL cells approved by the Sponsor; (10) symptomatic progression or other indication for treatment; (11) at least 3 months following hematopoietic stem cell transplant; (12) consent to undergo collection of paired CLL samples (screening and on study) for biomarker analysis including CLL cells in blood, lymph node or bone marrow; (9) laboratory confirmation of deletion of chromosome 11q22 (ATM) in CLL cells approved by the Sponsor; (10) symptomatic progression or other indication for treatment; (11) at least 3 months following hematopoietic stem cell transplant; (12) consent to undergo collection of paired CLL samples (screening and on study) for biomarker analysis including CLL cells in blood, lymph node or bone marrow.

Cohort may be expanded to enroll a minimum of 5 subjects with tumors with DNA-PK overexpression.

Length of Study.

Subjects start Compound 1 with 10 mg BID, receiving daily treatment in 28-day cycles. Compound 1 may be discontinued when there is evidence of tumor progression, but subjects can continue to receive study drug as long as the investigator considers they are deriving benefit. Therapy is discontinued when there is unacceptable toxicity or the subject decides to withdraw from the study.

Enrollment is expected to take about 30 months to complete. Extended treatment for responding subjects and follow-up may last another 3-6 months.

Study Treatments.

Compound 1 will be provided as capsules for oral administration. Most subjects will start Compound 1 at 10 mg BID.

Overview of Efficacy Assessments.

All treated subjects will be included for the efficacy analysis. The primary efficacy variable is tumor response, based on investigator assessment using the updated criteria of the National Cancer Institute-Sponsored Working Group on Chronic Lymphocytic Leukemia (NCI-WG CLL) for CLL which is the criteria of the International Workshop on Chronic Lymphocytic Leukemia (IWCLL). Supplementary efficacy variables (e.g., CTC quantification) will also be examined.

Overview of Safety Assessments.

Primary and exploratory safety variables for this study include AEs, comprehensive panels of clinical laboratory variables (including hematology, chemistry, immunology and thyroid function, and analytes assessing glucose homeostasis), 12-lead triplicate electrocardiograms (ECGs) centrally analyzed, left ventricle ejection fraction (LVEF) assessments, physical examinations, ECOG performance status (ECOG PS) and vital signs.

The Safety Review Committee (SRC) will determine the appropriate dose, doses, or schedule. The SRC will continue to review safety data regularly and make recommendations about the study continuation, as appropriate.

Overview of Pharmacokinetic Assessments.

The PK profiles of Compound 1, and any major metabolites detected, will be determined from serial blood and urine collections, including tumor tissue when available, and correlated with PD outcomes, where possible.

Overview of Pharmacodynamic Assessments.

Exploratory endpoints include mTOR and DNA-PK biomarker inhibition in circulating blood cells, and other tumor cells and/or tissue and aspirates, as available, UV-stimulated DNA-PK activity in skin, histopathologic response and correlations with pharmacogenomic findings. Paired (pre- and during-treatment) tumor biopsies are performed in most subjects with tumor lesions determined by the Investigator to be amenable to biopsy. Analysis will also include apoptosis and proliferation biomarkers in blood, skin, and/or tumor samples when available. The inhibition of mTOR and DNA-PK will be explored in circulating CLL cells, when possible.

Assessment Overview.

In certain embodiments, patients undergoing the clinical protocol provide herein show an achievement of the International Workshop on CLL (IWCLL) response definition of complete response, partial response or stable disease.

In certain embodiments, patients undergoing the clinical protocol provide herein show an achievement of the National Cancer Institute-Sponsored Working Group on CLL (NCI-WG CLL) response definition of complete response, partial response or stable disease.

In certain embodiments, patients undergoing the clinical protocol provide herein show an achievement of the International Workshop Criteria (IWC) response definition for maglignant lymphoma of complete response, partial response or stable disease.

5.2.4 Clinical Study B

Phase 1a/1b, Multi-Center, Open-Label, Dose Finding Study to Assess the Safety, Tolerability, Pharmacokinetics and Preliminary Efficacy of Compound 1 Administered Orally to Subjects with CLL or T-PLL Characterized by Deletion of all or Part of Chromosome 11q or Loss or Mutation of the Gene Encoding ATM, or Loss of ATM Expression or Function.

Study Objectives.

The primary objectives of the study are to: (1) determine the safety and tolerability of Compound 1 when administered orally; (2) define the non-tolerated dose (NTD) of Compound 1; (3) define the maximum tolerated dose (MTD) of Compound 1; and (4) determine the pharmacokinetics (PK) of Compound 1, when Compound 1 is administered to patients having CLL characterized by deletion of all or part of chromosome 11q or loss or mutation of the gene encoding ATM, or loss of ATM expression or function.

The secondary objectives of the study are to: (1) evaluate the extent of inhibition of phosphorylation of S6RP and/or 4E-BP1 for mTORC1 activity and AKT and/or other relevant biomarkers for mTORC2 activity in blood, skin and/or tumor biopsies/aspirates, when available before and during treatment with Compound 1; (2) evaluate the inhibition of DNA-dependent protein kinase (DNA-PK) activity in skin samples irradiated by UV light, circulating leukemia or other tumor cells, and/or tumor biopsies/aspirates using pDNA-PK S2056 and/or other relevant biomarkers for DNA damage pathways before and during Compound 1 treatment; and (3) evaluate the efficacy of Compound 1.

Study Design.

In this study, Compound 1 is administered orally to patients having CLL or T-PLL characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity.

This Phase 1a/1b study has two parts, dose escalation (Part A) and dose expansion (Part B).

In Part A, cohorts of subjects will initially receive once-daily (QD) ascending doses of Compound 1 to measure PK and identify the MTD. A modified accelerated titration design (Simon, R. et al, *J Nat Canc Institute* 1997; 89(15): 1138-1147) will be used to identify initial toxicity. During the accelerated phase, initial cohorts of one subject will be given Compound 1 in dose increments of 100% until the first instance of first-Cycle grade 2 or higher toxicity suspected to be drug-related, at which point the accelerated phase will stop and that particular cohort will be expanded to a total of 6 subjects. Subsequently, a standard escalation schedule with approximately 50% dose increments and 6-subject cohorts will be initiated in order to establish the NTD and MTD. Smaller increments within a dose cohort may be evaluated, if necessary. Cohorts may also be expanded for reasons other than toxicity based on review of PK and pharmacodynamic (PD) data, as well as on findings from tumor biopsies.

Based on interim PK and PD results from initial dose cohorts, a twice-daily (BID) dosing regimen will also be evaluated in Part A. This will be initiated in cohorts of 6 subjects at or below a total daily dose level already shown to be tolerable, but divided into two equal doses administered approximately 12 hours apart. Thereafter, dose escalation for QD and BID dosing cohorts may occur independently. Intermittent dosing schedules of comparable or lower dose intensity than continuous daily dosing may also be considered for evaluation.

A dose will be considered the NTD when 2 or more out of 6 evaluable subjects in a cohort experience drug-related dose-limiting toxicity (DLT) during Cycle 1. Once the NTD is established, dose escalation will stop. The MTD is defined as the last dose level below the NTD with 0 or 1 out of 6 evaluable subjects experiencing DLT during Cycle 1. An intermediate dose (ie, one between the NTD and the last dose level before the NTD) or additional subjects within any dose cohort may be required to more precisely determine the MTD, as may alternate regimens if emerging PK-PD results suggest these may be appropriate.

In Part B, adult subjects will start Compound 1 at 10 mg BID. A total of approximately 100 subjects will be evaluated for safety and antitumor activity periodically. Cohorts with up to 20 subjects/cohort, will be included.

A clinical pharmacology substudy will be performed in 12 evaluable subjects in the US. This is designed specifically to provide intrasubject PK comparisons for the current capsule and a recently formulated tablet, and to assess the effect of food on Compound 1 bioavailability to determine whether fasting restrictions around Compound 1 dosing could be lifted.

Study Population.

Men and women, 18 years or older, with CLL, and including subjects who have progressed on (or not been able to tolerate) standard anticancer therapy, or for whom no other approved therapy exists.

Inclusion Criteria.

Inclusion criteria are: (1) understand and voluntarily sign an informed consent document before any study-related assessments/procedures are conducted; (2) men and women, 18 years or older, with histological or cytological confirmation of CLL, including those who have progressed on (or not been able to tolerate) standard anticancer therapy or for whom no other conventional therapy exists; (3) consent to screening tumor biopsy; (4) ECOG PS of 0 or 1; (5) the following laboratory values: (i) absolute neutrophil count (ANC)$\geq 1.0 \times 10^9$/L; (ii) hemoglobin (Hgb)$\geq 9$ g/dl; (iii) platelets (plt)$\geq 30 \times 10^9$/L; (ii) hemoglobin (Hgb)$\geq 9$ g/dL; (iii) platelets (plt)$\geq 100 \times 10^9$/L; (iv) potassium within normal range, or correctable with supplements; (v) AST/SGOT and ALT/SGPT$\leq 2.5\times$ Upper Limit of Normal (ULN) or $\leq 5.0\times$ ULN if liver tumor is present; (vi) serum total bilirubin $\leq 1.5 \times$ULN; (vii) serum creatinine $\leq 1.5\times$ULN, or 24-hr clearance $\geq 50$ mL/min; and (viii) negative serum or urine pregnancy test within 72 hrs before starting study treatment in females of childbearing potential; (6) able to adhere to the study visit schedule and other protocol requirements; (7) subject consent to retrieve blood samples; (8) histologically-confirmed CLL (relapsed or refractory CLL, including the small lymphocytic lymphoma (SLL) variant, and T-cell prolymphocytic leukemia (T-PLL), following failure of at least one prior line of systemic therapy); (9) Confirmation of deletion of chromosome 11q22 (ATM) in CLL/SLL/T-PLL cells, or biallelic ATM mutations, in a laboratory approved by the Sponsor; (10) symptomatic progression or other indication for treatment; (11) at least 3 months following hematopoietic stem cell transplant; (12) consent to undergo collection of paired CLL samples (screening and on study) for biomarker analysis including CLL cells in blood, lymph node or bone marrow; (9) laboratory confirmation of deletion of chromosome 11q22 (ATM) in CLL cells approved by the Sponsor; (10) symptomatic progression or other indication for treatment; (11) at least 3 months following hematopoietic stem cell transplant; (12) consent to undergo collection of paired CLL/SLL/T-PLL samples (screening and on study) for biomarker analysis including CLL cells in blood, lymph node or bone marrow.

Cohort may be expanded to enroll a minimum of 5 subjects with tumors with DNA-PK overexpression.

Exclusion Criteria.

Exclusion criteria are: (1) symptomatic central nervous system metastases, (2) known acute or chronic pancreatitis; (3) any peripheral neuropathy ≥NCI CTCAE grade 2; (3) persistent diarrhea or malabsorption ≥NCI CTCAE grade 2, despite medical management. Impaired ability to swallow; (4) impaired cardiac function or clinically significant cardiac diseases, including any of the following: LVEF<45% as determined by MUGA scan or ECHO; complete left bundle branch, or bifascicular, block; congenital long QT syndrome; persistent or history of clinically meaningful ventricular arrhythmias or atrial fibrillation; QTcF>460 msec on screening ECG (mean of triplicate recordings); unstable angina pectoris or myocardial infarction ≤3 months prior to starting Compound 1; or other clinically significant heart disease such as congestive heart failure requiring treatment or uncontrolled hypertension (blood pressure ≥160/95 mmHg); (6) diabetes mellitus on active treatment, or subjects with either of the following: fasting blood glucose (FBG)≥126 mg/dL (7.0 mmol/L), or HbA1c≥6.5%; (7) other concurrent severe and/or uncontrolled concomitant medical conditions (eg, active or uncontrolled infection) that could cause unacceptable safety risks or compromise compliance with the protocol; (8) prior systemic cancer-directed treatments or investigational modalities ≤5 half lives or 4 weeks, whichever is shorter, prior to starting study drug or who have not recovered from side effects of such therapy; (9) major surgery ≤2 weeks prior to starting study drug or who have not recovered from side effects of such therapy. Subjects must have recovered from any effects of recent radiotherapy that might confound the safety evaluation of study drug. Hematopoietic stem cell transplant ≤3 months prior to starting study drug; (10) pregnancy or breastfeeding; (11) adults of reproductive potential not employing two forms of birth control: females of childbearing potential must agree to use two adequate forms of contraception methods simultaneously (one must be non-hormonal) from the time of giving informed consent until 28 days after the last dose of Compound 1. Females of child-bearing potential, defined as sexually mature women who have not undergone a hysterectomy or bilateral oophorectomy, or who have not been naturally postmenopausal (ie, who have not menstruated at all) for >24 consecutive months; males having partners who are female with child-bearing potential must agree that they and/or their partners will use at least two effective contraceptive methods (including one barrier method) when engaging in reproductive sexual activity throughout the study from the time of informed consent, and will avoid conceiving for 28 days after the last dose of Compound 1; (12) known human immunodeficiency virus (HIV) infection; (13) known chronic hepatitis B or C virus (HBV/HCV) infection, unless this is comorbidity in subjects with HCC; (14) any significant medical condition, laboratory abnormality, or psychiatric illness that would prevent subjects from participating in the study, including the inability to swallow capsules in the absence of a gastric/jejunal feeding tube; (15) any condition including the presence of laboratory abnormalities, which places subjects at unacceptable risk if they were to participate in the study; (16) any condition that confounds the ability to interpret study data; (17) concurrent active second malignancy for which the subject is receiving therapy, excluding non-melanomatous skin cancer or carcinoma in situ of the cervix; (18) Part B only: Prior treatment with agents targeting both mTOR complexes (dual TORC1+TORC2 inhibitors). However, prior treatment with isolated TORC1 inhibitors (eg, rapalogs) and other related pathway inhibitors (e.g., PI3K/AKT) is allowed in both parts of this study Length of Study.

Subjects start Compound 1 QD or BID dosing on Cycle 1 Day 1 in Part A, and adult subjects with 10 mg BID in Part B, all subjects receiving treatment in 28-day cycles. Compound 1 may be discontinued when there is evidence of tumor progression, but subjects can continue to receive study drug as long as the investigator considers they are deriving benefit. Therapy will be discontinued when there is unacceptable toxicity or the subject decides to withdraw from the study.

The End of Trial is defined as either the date of the last visit of the last subject to complete the study, or the date of receipt of the last data point from the last subject that is required for primary, secondary and/or exploratory analysis, as pre-specified in the protocol and/or the Statistical Analysis Plan, whichever is the later date.

Enrollment is expected to take about 30 months to complete. Extended treatment for responding subjects and follow-up may last another 3-6 months.

Study Treatments.

In Part A, the dose level will start at 0.5 mg QD. After the first dose is administered in any cohort, subjects are observed for at least 28 days before the next higher, protocol-specified dose cohort can begin. The total number of subjects in Part A depends on the number of dose cohorts needed to establish the MTD, and it is estimated that approximately 30-50 subjects will be enrolled in Part A.

Both QD and BID dosing will be evaluated in Part A. Twice-daily dosing will be initiated in cohorts of 6 subjects at or below a total daily dose level already shown to be tolerable, divided into two equal doses. Thereafter, dose escalation for QD and BID dosing cohorts may occur independently. Intermittent dosing schedules of comparable or lower dose intensity than continuous daily dosing, and intermediate doses between two dose levels already evaluated in Part A, may be investigated in Part B. In Part B, adult subjects will start Compound 1 at 10 mg BID. Approximately 100 subjects will be evaluated for safety and antitumor effects.

Compound 1 will be provided as capsules for oral administration. Most subjects will start Compound 1 at 10 mg BID.

Overview of Efficacy Assessments.

All treated subjects will be included for the efficacy analysis. The primary efficacy variable is tumor response, based on investigator assessment using the updated criteria of the National Cancer Institute-Sponsored Working Group on Chronic Lymphocytic Leukemia (NCI-WG CLL, 2008). Supplementary efficacy variables (e.g., CTC quantification) will also be examined.

Overview of Safety Assessments.

Primary and exploratory safety variables for this study include AEs, comprehensive panels of clinical laboratory variables (including hematology, chemistry, immunology and thyroid function, and analytes assessing glucose homeostasis), 12-lead triplicate electrocardiograms (ECGs) centrally analyzed, left ventricle ejection fraction (LVEF) assessments, physical examinations, ECOG performance status (ECOG PS) and vital signs.

In Part A, the decision to either evaluate a higher dose level or declare a MTD will be determined by the Safety Review Committee (SRC) each time clinical and laboratory safety data for a given cohort are available for review. The Safety Review Committee (SRC) will also determine the dose, doses, or schedule appropriate for Part B. During Part B, the SRC will continue to review safety data regularly and make recommendations about the study continuation, as appropriate.

Overview of Pharmacokinetic Assessments.

The PK profiles of Compound 1, and any major metabolites detected, will be determined from serial blood and urine collections, including tumor tissue when available, and correlated with PD outcomes, where possible.

Overview of Pharmacodynamic Assessments.

Exploratory endpoints include mTOR and DNA-PK biomarker inhibition in circulating blood cells, CTC, other tumor cells and/or tissue and aspirates, as available, UV-stimulated DNA-PK activity in skin, histopathologic response and correlations with pharmacogenomic findings. Paired (pre- and during-treatment) tumor biopsies will be performed in most subjects with tumor lesions determined by the Investigator to be amenable to biopsy. Analysis will also include apoptosis and proliferation biomarkers in blood, skin, and/or tumor samples when available. In Part B, the inhibition of mTOR and DNA-PK will be explored in circulating leukemia cells, when possible.

Assessment Overview.

In certain embodiments, patients undergoing the clinical protocol provide herein show an achievement of the International Workshop on CLL (IWCLL) response definition of complete response, partial response or stable disease.

In certain embodiments, patients undergoing the clinical protocol provide herein show an achievement of the National Cancer Institute-Sponsored Working Group on CLL (NCI-WG CLL) response definition of complete response, partial response or stable disease. In certain embodiments, patients undergoing the clinical protocol provide herein show an achievement of the International Workshop Criteria (IWC) response definition for maglignant lymphoma of complete response, partial response or stable disease.

A number of references have been cited, the disclosures of which are incorporated herein by reference in their entirety. The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein in addition to those shown and described herein will become apparent to those skilled in the art and are intended to fall within the scope of the appended claims.

What is claimed is:

1. A method for treating CLL or T-PLL, comprising administering an effective amount of 1-ethyl-7-(2-methyl-6-(4H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof to a patient having CLL or T-PLL, wherein said patient is administered about 0.5 mg once per day or about 4 mg, about 8 mg or about 10 mg twice per day of 1-ethyl-7-(2-methyl-6-(1H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof.

2. The method of claim 1, wherein said patient is administered about 0.5 mg once per day of 1-ethyl-7-(2-methyl-6-(1H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof.

3. The method of claim 1, wherein said patient is administered about 4 mg, about 8 mg or about 10 mg twice per day of 1-ethyl-7-(2-methyl-6-(1H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof.

4. The method of claim 1, wherein said patient is administered about 10 mg twice per day of 1-ethyl-7-(2-methyl-6-(1H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof.

5. The method of claim 1, wherein said patient is administered a unit dosage form comprising 0.25 mg, 1.0 mg, 5.0 mg, 7.5 mg, or 10 mg of 1-ethyl-7-(2-methyl-6-(1H-1,2,4-triazol-3-yl)pyridin-3-yl)-3,4-dihydropyrazino[2,3]pyrazin-2(1H)-one or a pharmaceutically acceptable salt, stereoisomer or tautomer thereof.

6. A method for achieving an International Workshop on Chronic Lymphocytic Leukemia (IWCLL) response definition of complete response, complete response with incomplete marrow recovery, partial response or stable disease in a patient having CLL or T-PLL, comprising administering an effective amount of 1-ethyl-7-(2-methyl-6-(4H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof to said patient, wherein said patient is administered about 0.5 mg once per day or about 4 mg, about 8 mg or about 10 mg twice per day of 1-ethyl-7-(2-methyl-6-(1H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof.

7. A method for achieving a National Cancer Institute-sponsored Working Group on Chronic Lymphocytic Leukemia (NCI-WG CLL) response definition of complete response, complete response with incomplete marrow recovery, partial response or stable disease in a patient having CLL or T-PLL, comprising administering an effective amount of 1-ethyl-7-(2-methyl-6-(4H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof to said patient, wherein said patient is administered about 0.5 mg once per day or about 4 mg, about 8 mg or about 10 mg twice per day of 1-ethyl-7-(2-methyl-6-(1H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof.

8. A method for treating CLL or T-PLL, comprising administering an effective amount of 1-ethyl-7-(2-methyl-6-(4H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof to a patient having CLL or T-PLL, wherein the treatment results in one or more of inhibition of disease progression, increased Time To Progression (TTP), increased Overall Survival (OS), increased Progression-free Survival (PFS), increased Event-free Survival, increased Disease-free Survival, increased Response Duration, increased Lymphoma-specific survival, and/or increased Time To Next Treatment, wherein said patient is administered about 0.5 mg once per day or about 4 mg, about 8 mg or about 10 mg twice per day of 1-ethyl-7-(2-methyl-6-(1H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof.

9. The method of claim 1, 6, 7 or 8, wherein the CLL or T-PLL is characterized by deletion of all or part of chromosome 11q, loss or mutation of the gene encoding ATM, loss of ATM expression or function, mutation of IgVH, wild type IgVH, wild type p53/ATM, mutation of p53, dysfunctional p53 or Zap-70 positivity.

10. The method of claim 1, 6, 7 or 8, wherein the CLL or T-PLL is characterized by deletion of all or part of chromosome 11q or loss or mutation of the gene encoding ATM.

11. A method for treating CLL or T-PLL, comprising administering an effective amount of 1-ethyl-7-(2-methyl-6-(4H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof in combination with etoposide to a patient having CLL or T-PLL.

* * * * *